US008853204B2

(12) United States Patent
Powell et al.

(10) Patent No.: US 8,853,204 B2
(45) Date of Patent: Oct. 7, 2014

(54) PHARMACEUTICAL COMPOSITION COMPRISING A BENZODIAZEPINE DERIVATIVE AND AN INHIBITOR OF THE RSV FUSION PROTEIN

(75) Inventors: Kenneth Powell, London (GB); Richard Kelsey, London (GB); Malcolm Carter, London (GB); Dagmar Alber, London (GB); Lara Wilson, London (GB); Elisa Henderson, London (GB); Phil Chambers, London (GB); Debra Taylor, London (GB); Stan Tyms, London (GB); Verity Dowdell, London (GB)

(73) Assignee: Arrow Therapeutics Limited (GB)

( * ) Notice: Subject to any disclaimer, the term of this patent is extended or adjusted under 35 U.S.C. 154(b) by 1482 days.

(21) Appl. No.: 10/593,666

(22) PCT Filed: Mar. 18, 2005

(86) PCT No.: PCT/GB2005/001018
§ 371 (c)(1),
(2), (4) Date: Mar. 12, 2007

(87) PCT Pub. No.: WO2005/089769
PCT Pub. Date: Sep. 29, 2005

(65) Prior Publication Data
US 2007/0142403 A1 Jun. 21, 2007

(30) Foreign Application Priority Data
Mar. 19, 2004 (GB) .................................. 0406282.4

(51) Int. Cl.
A01N 43/62 (2006.01)
A61K 31/55 (2006.01)
A01N 43/52 (2006.01)
A61K 31/415 (2006.01)
C07D 243/24 (2006.01)
C07D 235/04 (2006.01)
A61K 45/06 (2006.01)
A61K 31/5513 (2006.01)

(52) U.S. Cl.
CPC ............. A61K 45/06 (2013.01); A61K 31/5513 (2013.01)
USPC .......... 514/221; 514/394; 540/509; 548/305.1

(58) Field of Classification Search
USPC ................. 514/221, 394; 540/509; 548/305.1
See application file for complete search history.

(56) References Cited

U.S. PATENT DOCUMENTS 4,324,794 A * 4/1982 Tidwell et al. ................ 514/387

FOREIGN PATENT DOCUMENTS

| WO | WO 9845275 A1 | * | 10/1998 |
| WO | WO 01/95910 | * | 12/2001 |
| WO | WO02/26228 A1 | * | 4/2002 |
| WO | WO 2004/026943 | * | 4/2004 |

OTHER PUBLICATIONS

Bell et. al., Journal of Medicinal Chemistry, 1968, American Chemical Society, 11, 457-461.*
Broughton et. al., Expert Opin. Pharmacother., 2003, Ashley Publications, vol. 4, No. 10, pp. 1801-1808.*

* cited by examiner

Primary Examiner — Sarah Pihonak
(74) Attorney, Agent, or Firm — McCarter & English LLP; Elizabeth A. Hanley, Esq.; Michael J. DeGrazia

(57) ABSTRACT

A pharmaceutical composition which comprises a pharmaceutically acceptable carrier or diluent and: (a) an inhibitor of the RSV fusion protein; and (b) a benzodiazepine derivative capable of inhibiting RSV replication is found to be highly active against RSV.

28 Claims, No Drawings

PHARMACEUTICAL COMPOSITION COMPRISING A BENZODIAZEPINE DERIVATIVE AND AN INHIBITOR OF THE RSV FUSION PROTEIN

RELATED APPLICATIONS

This application is a 35 U.S.C. 371 national stage filing of International Application No. PCT/GB2005/001018, filed 18 Mar. 2005, which claims priority to British Patent Application No. 0406282.4 filed on 19 Mar. 2004 in Great Britain. The contents of the aforementioned applications are hereby incorporated by reference.

The present invention relates to a series of anti-viral benzodiazepine derivatives. In particular, it relates to a series of benzodiazepine derivatives which interact with an inhibitor of the RSV fusion protein to provide an additive or synergistic therapeutic effect in treating or preventing an RSV infection.

Respiratory Syncytial Virus (RSV) is a major cause of respiratory illness in patients of all ages. In adults, it tends to cause mild cold symptoms. In school-aged children, it can cause a cold and bronchial cough. In infants and toddlers it can cause bronchiolitis (inflammation of the smaller airways of the lungs) or pneumonia. It has also been found to be a frequent cause of middle ear infections (otitis media) in pre-school children. RSV infection in the first year of life has been implicated in the development of asthma during childhood.

Current anti-RSV therapy involves the use of a monoclonal antibody to RSV, called palivizumab. Such use of palivizumab is a prophylactic, rather than therapeutic, treatment of RSV. However, although this antibody is often effective, it is expensive. Indeed, its expense means that it is unavailable for many people in need of anti-RSV therapy. There is therefore an urgent need for effective alternatives to existing anti-RSV therapy.

Small compounds which inhibit RSV replication by inhibiting the fusion (F) protein of RSV block the entry of the virus into the host cell and the exit from the host cell via syncytia formation. While these compounds have been shown to have high potency, RSV rapidly develops resistance to these compounds through mutations in the F protein (Morton, C. J. et al, 2003.Virology 311, 275-288).

PCT/GB03/04050 filed on 20 Sep. 2003 discloses a series of benzodiazepine derivatives which inhibit RSV replication. Serial passaging experiments have indicated that resistance to these inhibitors is slow to develop and sequencing of resistant mutants did not reveal any significant changes in the F protein. It can therefore be assumed that these benzodiazepines have a common and novel mode of action, which does not involve inhibition of the F-protein.

It has now surprisingly been shown that a combination of (a) an RSV fusion protein inhibitor and (b) an anti-RSV benzodiazepine is highly active against RSV. Components (a) and (b) are found to have at least an additive effect. Further, it is also a finding of the invention that the two components interact synergistically, to provide a combined effect that is greater than the sum of the effects of the individual components.

The present invention therefore provides, in a first embodiment, a pharmaceutical composition which comprises a pharmaceutically acceptable carrier or diluent and
(a) an inhibitor of the RSV fusion protein; and:
(b) a benzodiazepine derivative capable of inhibiting RSV replication.

It is a finding of the present invention that components (a) and (b) have at least an additive effect. The concepts of synergism and additivity are, of course, well known in the field of pharmacology. It is thus well established that a therapeutically useful additive combination is one in which the effect of the combination is greater than the larger of the effects produced by each of the components at the same concentrations as in the mixture. Thus, in the present case, a given formulation containing x wt % of component (a) and y wt % of component (b) has an activity which is at least as great as the activity of a formulation containing, as sole active ingredient, either x wt % component (a) or y wt % component (b).

In such additive combinations, the active ingredients are typically operating via different physiological pathways. In the present case, for example, component (a) and component (b) are believed to be inhibiting separate RSV proteins. An additive combination is therapeutically useful because it can achieve a therapeutically useful effect using lower concentrations of each active component. This enables the side-effects of the medication to be minimised. Thus, the additive combination can be formulated so that each active ingredient is present at a concentration which is subclinical in cells other than the target disease cells. The additive combination is nevertheless therapeutically effective in target cells which respond to both ingredients.

As regards component (a), an inhibitor of the RSV fusion protein can be identified by an assay comprising:
(a) labelling RSV with octadecyl rhodamine dye (R18);
(b) pre-incubating the labelled virus with Hep-2 cells seeded in a 6-well plate at 1 hour for 4° C.;
(c) removing unattached virus;
(d) adding the candidate fusion protein inhibitor;
(e) incubating the 6-well plates at 37° C. for 1 hour; and
(f) determining any increase in fluorescence, typically using a fluorescence microscope.

In the above assay, any increase in fluorescence signifies a fusion event. Thus, if no increase in fluorescence is detected, 100% inhibition is achieved. If the increase in fluorescence is equal to that observed with a corresponding assay in which a control of growth medium and solvent (e.g., growth medium with 10% fetal bovine serum and DMSO) is used in step (d) in place of the candidate fusion protein inhibitor, 0% inhibition is achieved. Accordingly the % inhibition achieved with the candidate fusion protein inhibitor can be determined by quantitative assessment of the fluorescence in step (f).

As used herein, component (a) is typically a compound which achieves at least 10%, more typically at least 30%, preferably at least 50% and most preferably at least 75%, inhibition of the RSV fusion protein as determined by the above assay.

Typically, component (a) is a compound of formula (1), or a pharmaceutically acceptable salt thereof,

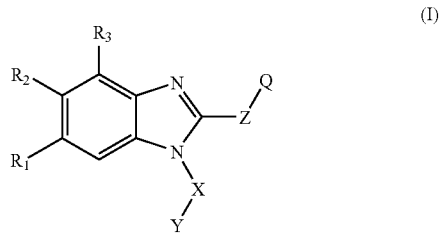

wherein:
X is a direct link or $C_{1-6}$ alkyl; said $C_{1-6}$ alkyl being optionally substituted with halogen, oxo, cyano, hydroxyl, $OCOR_4$ or $S(O)n$-$C_{1-6}$ alkyl;

Y is $R_4$, $NR_4R_5$, $NCOR_4$, =N—$O_4$, —$CONHR_4$, $COOR_4$, —$OR_4$, aryl, heteroaryl, cyclyl or heterocyclyl, where $R_4$ and $R_5$ are H or $C_{1-6}$ alkyl;

Z is $CR_6R_7$, where $R_6$ and $R_7$ are independently H, or straight, branched or cyclic $C_{1-6}$ alkyl;

n is 1-2;

$R_1$ is $CONR_4R_5$, $CO_2R_4$ or $C_{1-6}$ alkyl, said $C_{1-6}$ alkyl can be optionally substituted with $OR_4$ or $NR_8R_9$;

$R_8$ and $R_9$ are each independently H, $C_{1-6}$ alkyl, $SO_2R_5$, $CO_2R_4$ or $COR_4$;

$R_2$ is selected from the group consisting of $NH_2$, $CONR_6R_7$, heteroaryl, $C_{2-6}$ alkenyl, $CO_2R_4$, N=$CPh_2$, C(=NH)$NH_2$ and $C_{1-6}$ alkyl; said alkyl optionally substituted with a member selected from the group consisting of halogen, CN, $NR_{10}R_{11}$, $OSO2R_4$ and $OR_4$;

$R_{10}$ and $R_{11}$ are each independently selected from the group consisting of H, $C_{1-6}$ alkyl, $C_{3-6}$ cycloalkyl, $CO_2R_4$, $COR_4$ and $SO_2R_4$;

$R_3$ is selected from the group consisting of (1) $CO_2R_9$; (2) $C_{1-6}$ alkyl optionally substituted with CN, $OR_4$ or $NR_6R_7$; and (3) $C_{2-6}$ alkenyl substituted with CN;

Q is a member selected from the group consisting of

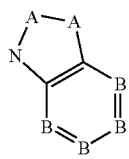

A is C or N, optionally substituted with H, halogen, $C_{1-6}$ alkyl, $C_{2-6}$ alkenyl, cyano-$C_{1-6}$ alkyl, $CO_2R_4$, aryl, benzoaminocarbonyl, hydroxybenzyl, $SO_2NR_4R_5$ or $C_{3-6}$ cycloalkyl. Where A is carbon, it may also be optionally substituted by O or S via a double bond;

B is C or N; where B is C it may be optionally substituted by H, $C_{1-6}$ alkyl, $NO_2$, CN, halogen, $COR_4$, $COOR_4$, $CONHR_4C$(=NH)$NH_2$ or C(=NOH)$NH_2$.

Typically, at least two of $R_1$, $R_2$ and $R_3$ are hydrogen, and the other is hydrogen or —C(NH)—$NH_2$. Preferably, all of $R_1$, $R_2$ and $R_3$ are hydrogen.

Typically, either —X—Y is H, or X is a $C_1$-$C_6$ alkylene group which is unsubstituted or substituted by a hydroxy group and Y is H, OH, CN, —NR'R'', —COR', —$SO_2R'$ or phenyl, wherein R' and R'' are the same or different and represent a $C_1$-$C_4$ alkyl group.

Typically, Z is —$CH_2$—.

Typically, Q is a moiety

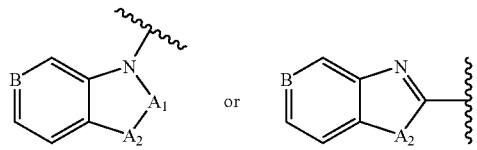

wherein B is —CH— or —N—, $A_1$ is —C(O)— or —NH— and $A_2$ is —$CH_2$—, —CHR'— or —NR''—, wherein R' is a halogen atom and R'' represents a hydrogen atom or a $C_1$-$C_4$ alkyl, $C_2$-$C_4$ alkenyl, $C_3$-$C_6$ cycloalkyl, $SO_2$—($C_1$-$C_6$ alkyl), —$SO_2$—N($C_1$-$C_6$ alkyl)$_2$ or —(CO—NH)$_a$—($C_1$-$C_4$ alkyl)-phenyl group, wherein a is 0 or 1, which group is unsubstituted or is substituted with a hydroxy or cyano substituent.

Particularly preferred compounds of the invention are compounds of formula (Ia) and pharmaceutically acceptable salts thereof

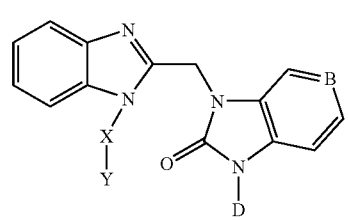

wherein

B, X and Y are as described in formula (I) above

D is cyclopropyl, ethyl, 4-cyanobutyl, isopropenyl, methylsulfonyl, dimethylsulfamoyl, benzylaminocarbamoyl or para-hydroxybenzyl Component (a) can also be a compound of formula (II), or a pharmaceutically acceptable salt thereof,

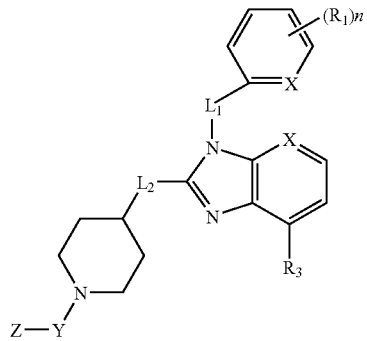

wherein:

$L_1$ is —$CH_2$— or —$CHR_2$—CO— each X is the same or different and is CH or N;

each $R_1$ is the same or different and is $C_{1-6}$ alkyl, halogen, hydroxy, phenyl or $(CH_2)_m$=$NH_2$;

n is 1 or 2;

$R_2$ is $C_{1-6}$ alkoxy or $C_{1-6}$alkoxy-phenyl;

$R_3$ is $C_{1-6}$alkyl;

$L_2$ is —$CH_2$— or —NH—;

Y is $C_{1-6}$ alkyl or $C_{1-6}$ alkenyl;

Z is H, N($R_4$)$_2$—, —C(=O)—$R_5$, —C(=$CH_2$)—$R_5$, —CH(OH)—$R_5$, —CH($CH_3$)—$R_5$, —CH(O$CH_3$)—$R_5$;

each $R_4$ is the same or different and is H, $C_{1-6}$ alkyl.

$R_5$ is $C_{1-6}$alkyl-carbonyl, amino, hydroxyl, aryl, heteroaryl, carbocyclyl, heterocyclyl; and m=1-6

For the avoidance of doubt, when $L_1$ is —$CHR_2$—CO—, the carbonyl moiety is attached to the phenyl or pyridine ring.

Typically, $L_1$ is —$CH_2$—.

Typically, $L_2$ is —NH—.

Typically, $R_1$ is methyl or hydroxy. Typically, n is 2. Typically, each $R_1$ is different.

Typically, Y is $C_1$-$C_4$ alkyl.

Typically, Z is —$NH_2$.

Other preferred compounds of formula (II) are compounds of formula

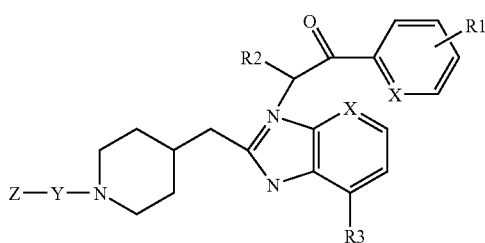

wherein:
X is C or N;
$R_1$ is $C_{1-6}$ alkyl, halogen, phenyl or $(CH_2)_m$=$NH_2$;

wherein

X is —N=C— or —CH=CH—;

$R_1$ is H, hydroxyl, alkyl, halogen, nitro or alkoxy; said alkoxy being optionally monosubstituted with carboxy, amino, monoalkylamino, dialkylamino or acetoamino;

$R_2$ is pyrazolyl, triazolyl or tetrazolyl and optionally substituted by amino or alkyl.

Component (a) can also be a compound of formula (IV), or a pharmaceutically acceptable salt thereof.

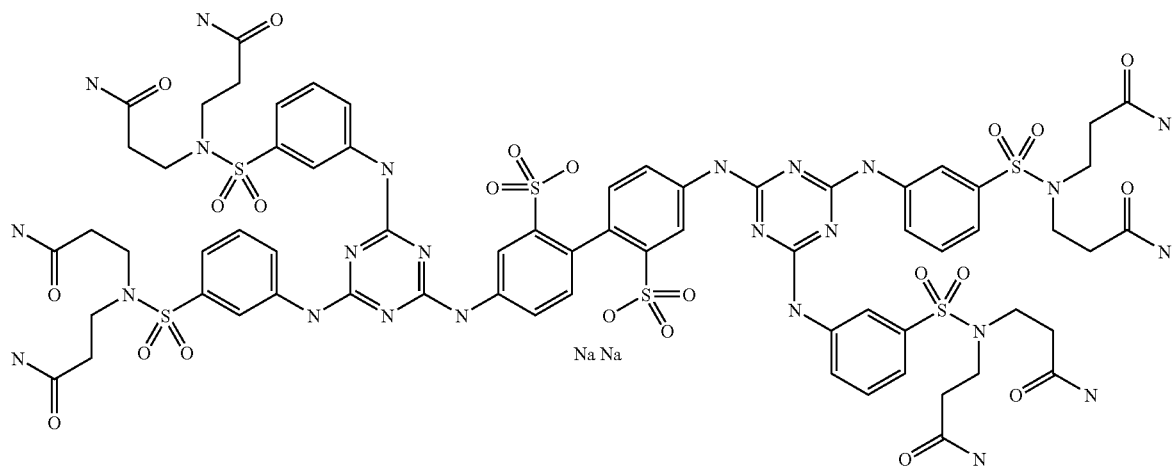

$R_2$ is $C_{1-6}$ alkoxy or $C_{1-6}$alkoxy-phenyl;
$R_3$ is $C_{1-6}$alkyl;
Y is $C_{1-6}$ alkyl or $C_{1-6}$ alkenyl;
Z is H, $NR_4$, —C(=O)—$R_5$, —C(=CH$_2$)—$R_5$, —CH(OH)—$R_5$, —CH(CH3)—$R_5$, —CH(OCH3)—$R_5$;
$R_4$ is H, $C_{1-6}$ alkyl.
$R_5$ is $C_{1-6}$ alkyl-carbonyl, amino, hydroxyl, aryl, heteroaryl, carbocyclyl, heterocyclyl
m=1-6

Component (a) can also be a compound of formula (III), or a pharmaceutically acceptable salt thereof,

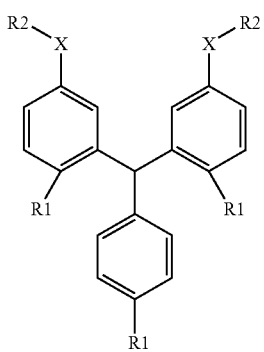

The compound of formula (IV) is 4,4'-Bis-(4,6-bis-{3-[bis-(2-carbamoyl-ethyl)-sulfamoyl]-phenylamino}-[1,3,5]triazin-2-ylamino)-biphenyl-2,2'-disulfonic acid.

Preferably, component (a) is:
1-Cyclopropyl-3-[1-(4-hydroxy-butyl)-1H-benzoimidazol-2-ylmethyl]-1,3-dihydro-imidazo[4,5-c]pyridin-2-one
{2-[2-(1,2-Dihydro-benzotriazol-1-ylmethyl)-benzoimidazol-1-yl]]ethyl}-diethyl-amine
{2-[2-(3-Iodo-2,3-dihydro-indazol-1-ylmethyl)-benzimidazol-1-yl]-ethyl}-dimethyl-amine
1-Isopropenyl-3-[1-(3-methyl-butyl)-1H-benzoimidazol-2-ylmethyl]-1,3-dihydro-benzoimidazol-2-one
1-(4-Hydroxy-benzyl)-3-[1-(3-methyl-butyl)-1H-benzoimidazol-2-ylmethyl]-1,3-dihydro-benzoimidazol-2-one
1-Isopropenyl-3-[1-(3-oxo-butyl)-1H-benzoimidazol-2-ylmethyl]-1,3-dihydro-benzoimidazol-2-one
1-Ethyl-3-[1-(2-hydroxy-2-phenyl-ethyl)-1H-benzoimidazol-2-ylmethyl]-1,3-dihydro-benzoimidazol-2-one
1-Ethyl-3-[1-(4-hydroxy-butyl)-1H-benzoimidazol-2-ylmethyl]-1,3-dihydro-benzoimidazol-2-one
7-[2-(3-Isopropenyl-2-oxo-2,3-dihydrobenzoimidazol-1-ylmethyl)-benzoimidazol-1-yl]-heptanenitril
5-{3-[1-(3-Methanesulfonyl-propyl)-1H-benzoimidazol-2-ylmethyl]-2-oxo-2,3-dihydro-benzoimidazol-1-yl}-pentanenitrile
3-[1-(3-Methyl-butyl)-1H-benzoimidazol-2-ylmethyl]-2-oxo-2,3-dihydro-benzoimidazol-1-carboxylic acid benzylamide
1-Methanesulfonyl-3-[1-(3-methyl-butyl)-1H-benzoimidazol-2-ylmethyl]-1,3-dihydro-benzoimidazol-2-one 3-[1-(3-Methyl-butyl)-1H-benzoimidazol-2-ylmethyl]-2-oxo-2,3-dihydro-benzoimidazol-1-sulfonic acid dimethylamide 1-Isopropenyl-3-(1-propyl-1H-benzoimidazol-2-ylmethyl)-1,3-dihydro-imidazo[4,5-c]pyridine-2-one Bis(5-amidino-2-benzimidazolyl)-methane 2-{2-[1-[1-(2-Amino-ethyl)-piperidin-4-ylamino]-4-methyl-benzoimidazol-1-ylmethyl}-6-methyl-pyridin-3-ol or a pharmaceutically acceptable salt thereof.

In a further embodiment, the composition contains an RSV fusion inhibitor, as described above, and a benzodiazepine identifiable as having anti-RSV activity by the method of Example 8.

Typically, component (b) is a compound of formula (V), or a pharmaceutically acceptable salt thereof,

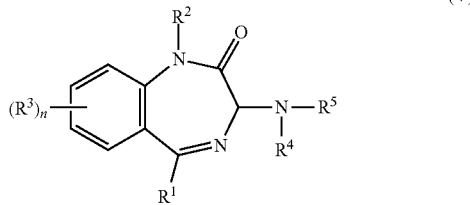

wherein:
$R^1$ represents $C_{1-6}$ alkyl, aryl or heteroaryl;
$R^2$ represents hydrogen or $C_{1-6}$ alkyl;
each $R^3$ is the same or different and represents halogen, hydroxy, $C_{1-6}$ alkyl, $C_{1-6}$ alkoxy, $C_{1-6}$ alkylthio, $C_{1-6}$ haloalkyl, $C_{1-6}$ haloalkoxy, amino, mono($C_{1-6}$ alkyl)amino, di($C_{1-6}$ alkyl)amino, nitro, cyano, —$CO_2R'$, —CONR'R", —NH—CO—R', —S(O)R', —S(O)$_2$R', —NH—S(O)$_2$R', —S(O)NR'R" or —S(O)$_2$NR'R", wherein each R' and R" is the same or different and represents hydrogen or $C_{1-6}$ alkyl;
n is from 0 to 3;
$R^4$ represents hydrogen or $C_{1-6}$ alkyl;
$R^5$ represents $C_{1-6}$ alkyl, aryl, heteroaryl, carbocyclyl, heterocyclyl, aryl-($C_{1-6}$ alkyl)-, heteroaryl-($C_{1-6}$ alkyl)-, carbocyclyl-($C_{1-6}$ alkyl)-, heterocyclyl-($C_{1-6}$ alkyl)-, aryl-C(O)—C(O)—, heteroaryl-C(O)—C(O)—, carbocyclyl-C(O)—C(O)—, heterocyclyl-C(O)—C(O)— or —XR$^6$.
X represents —CO—, —S(O)— or —S(O)$_2$—; and
$R_6$ represents $C_{1-6}$ alkyl, hydroxy, $C_{1-6}$ alkoxy, $C_{1-6}$ alkylthio, aryl, heteroaryl, carbocyclyl, heterocyclyl, aryl-($C_{1-6}$ alkyl)-, heteroaryl-($C_{1-6}$ alkyl)-, carbocyclyl-($C_{1-6}$ alkyl)-, heterocyclyl-($C_{1-6}$alkyl)-, aryl-($C_{1-6}$hydroxyalkyl)-, heteroaryl-($C_{1-6}$ hydroxyalkyl)-, carbocyclyl-($C_{1-6}$ hydroxyalkyl)-, heterocyclyl-($C_{1-6}$hydroxyalkyl)-, aryl-($C_{1-6}$ alkyl)-O—, heteroaryl-($C_{1-6}$ alkyl)-O—, carbocyclyl-($C_{1-6}$ alkyl)-O—, heterocyclyl-($C_{1-6}$ alkyl)-O— or —NR'R" wherein each R' and R" is the same or different and represents hydrogen, $C_{1-6}$ alkyl, carbocyclyl, heterocyclyl, aryl, heteroaryl, aryl-($C_{1-6}$ alkyl)-, heteroaryl-($C_{1-6}$ alkyl)-, carbocyclyl-($C_{1-6}$ alkyl)- or heterocyclyl-($C_{1-6}$ alkyl). Typically, R' and R" are not both hydrogen.

As used herein, a $C_{1-6}$ alkyl group or moiety is a linear or branched alkyl group or moiety containing from 1 to 6 carbon atoms, such as a $C_{1-4}$ alkyl group or moiety. Examples of $C_{1-4}$ alkyl groups and moieties include methyl, ethyl, n-propyl, i-propyl, n-butyl, i-butyl and t-butyl. For the avoidance of doubt, where two alkyl moieties are present in a group, the alkyl moieties may be the same or different.

As used herein, a hydroxyalkyl group is typically a said alkyl group that is substituted by one or more hydroxy groups. Typically, it is substituted by one, two or three hydroxy groups. Preferably, it is substituted by a single hydroxy group. Preferred hydroxyalkyl groups are (monohydroxy)ethyl groups.

As used herein, an acyl group is a $C_{2-7}$ acyl group, for example a group —CO—R, wherein R is a said $C_{1-6}$ alkyl group.

As used herein, an aryl group is typically a $C_{6-10}$ aryl group such as phenyl or naphthyl. Phenyl is preferred. An aryl group may be unsubstituted or substituted at any position. Typically, it carries 0, 1, 2 or 3 substituents.

Suitable substituents on an aryl group include halogen, $C_{1-6}$ alkyl, $C_{2-7}$ acyl, hydroxy, $C_{1-6}$ alkoxy, $C_{1-6}$ alkylthio, $C_{1-6}$ haloalkyl, $C_{1-6}$ haloalkoxy, nitro, cyano, carbamoyl, mono($C_{1-6}$ alkyl)carbamoyl, di($C_{1-6}$ alkyl)carbamoyl, amino, mono($C_{1-6}$ alkyl)amino, di($C_{1-6}$ alkyl)amino, —$CO_2R'$, —CONR'R", —S(O)R', —S(O)$_2$R', —S(O)NR'R", —S(O)$_2$NR'R"—NH—S(O)$_2$R' or —NH—CO—R', wherein each R' and R" is the same or different and represents hydrogen or $C_{1-6}$ alkyl. Examples of suitable substituents on an aryl group include halogen, $C_{1-6}$ alkyl, $C_{2-7}$ acyl, hydroxy, $C_{1-6}$ alkoxy, $C_{1-6}$ alkylthio, $C_{1-6}$ haloalkyl, $C_{1-6}$ haloalkoxy, nitro, cyano, carbamoyl, mono($C_{1-6}$ alkyl)carbamoyl, di($C_{1-6}$ alkyl)carbamoyl, amino, mono($C_{1-6}$ alkyl)amino, di($C_{1-6}$ alkyl)amino, —$CO_2R'$, —CONR'R", —S(O)R', —S(O)$_2$R", —S(O)NR'R", —NH—S(O)$_2$R' or —NH—CO—R', wherein each R' and R" is the same or different and represents hydrogen or $C_{1-6}$ alkyl.

Preferred substituents on an aryl group include halogen, $C_{1-6}$ alkyl, $C_{2-7}$ acyl, hydroxy, $C_{1-6}$ alkoxy, $C_{1-6}$ alkylthio, $C_{1-6}$ haloalkyl, $C_{1-6}$ haloalkoxy, amino, mono($C_{1-6}$ alkyl) amino, di($C_{1-6}$ alkyl)amino, nitro, cyano, —$CO_2R'$, —S(O)R', —S(O)$_2$R' and —S(O)$_2$NR'R", wherein each R' and R" is the same or different and represents hydrogen or $C_{1-4}$ alkyl. Examples of preferred substituents on an aryl group include halogen, $C_{1-6}$ alkyl, $C_{1-6}$ alkoxy, $C_{1-6}$ alkylthio, $C_{1-6}$ haloalkyl, $C_{1-6}$ haloalkoxy, mono($C_{1-6}$alkyl)amino, di($C_{1-6}$ alkyl)amino, nitro and cyano.

Particularly preferred substituents include fluorine, chlorine, bromine, iodine, $C_{1-4}$ alkyl, $C_{2-4}$ acyl, hydroxy, $C_{1-4}$ alkoxy, $C_{1-4}$ alkylthio, $C_{1-4}$ haloalkyl, $C_{1-4}$ haloalkoxy, amino, mono($C_{1-4}$ alkyl)amino, di($C_{1-4}$ alkyl)amino, nitro, —$CO_2R'$, —S(O)$_2$R' and —S(O)$_2$NH$_2$, wherein R' represents $C_{1-2}$ alkyl. Examples of particularly preferred substituents include fluorine, chlorine, bromine, $C_{1-4}$ alkyl, $C_{1-4}$ alkoxy, $C_{1-4}$ haloalkyl and nitro.

As used herein, references to an aryl group include fused ring systems in which an aryl group is fused to a monocyclic carbocyclyl, heterocyclyl or heteroaryl group or to a fused group which is a monocyclic carbocyclyl, heterocyclyl or heteroaryl group which is fused to a phenyl ring. Typically, said fused ring systems are systems in which an aryl group is fused to a monocyclic carbocyclyl, heterocyclyl or heteroaryl group. Preferred such ring systems are those wherein an aryl group is fused to a fused group which is a monocyclic heterocyclyl or heteroaryl group or to a monocyclic carbocyclic group fused to a phenyl ring, in particular those wherein an aryl group is fused to a heterocyclyl or heteroaryl group. Examples of such fused ring systems are groups in which a phenyl ring is fused to a thienyl group or to a tetrahydrofuranyl group to form a benzothienyl or dihydrobenzofuranyl group. Further examples of such fused rings are groups in which a phenyl ring is fused to a dioxanyl group, a pyrrolyl group or a 2,3-dihydroinden-1-one group to form a benzodioxinyl, indolyl or a 9H-fluoren-9-one group.

As used herein, a carbocyclyl group is a non-aromatic saturated or unsaturated monocyclic hydrocarbon ring, typically having from 3 to 6 carbon atoms. Preferably it is a saturated hydrocarbon ring (i.e. a cycloalkyl group) having from 3 to 6 carbon atoms. Examples include cyclopropyl, cyclobutyl, cyclopentyl and cyclohexyl. It is preferably cyclopentyl or cyclohexyl. A cycloalkyl group may be unsubstituted or substituted at any position. Typically, it carries 0, 1, 2 or 3 substituents.

Suitable substituents on a carbocyclyl group include halogen, $C_{1-6}$ alkyl, $C_{2-7}$ acyl, hydroxy, $C_{1-6}$ alkoxy, $C_{1-6}$ alkylthio, $C_{1-6}$ haloalkyl, $C_{1-6}$ haloalkoxy, nitro, cyano, carbamoyl, mono($C_{1-6}$ alkyl)carbamoyl-, di($C_{1-6}$ alkyl)carbamoyl, amino, mono($C_{1-6}$ alkyl)amino, di($C_{1-6}$ alkyl)amino, oxo, —$CO_2R'$, —$CONR'R''$, —$S(O)R'$, —$S(O)_2R'$, —$S(O)NR'R''$, —$S(O)_2NR'R''$, —NH—$S(O)_2R'$ or —NH—CO—R', wherein each R' and R'' is the same or different and represents hydrogen or $C_{1-6}$ alkyl. Examples of suitable substitutents on a carbocyclyl group include halogen, $C_{1-6}$ alkyl, $C_{2-7}$ acyl, hydroxy, $C_{1-6}$ alkoxy, $C_{1-6}$ alkylthio, $C_{1-6}$ haloalkyl, $C_{1-6}$ haloalkoxy, nitro, cyano, carbamoyl, mono($C_{1-6}$ alkyl)carbamoyl, di($C_{1-6}$ alkyl)carbamoyl, amino, mono($C_{1-6}$ alkyl)amino, di($C_{1-6}$ alkyl)amino, —$CO_2R'$, —$CONR'R''$, —$S(O)R'$, —$S(O)_2R'$, —$S(O)NR'R''$, —NH—$S(O)_2R'$ or —NH—CO—R', wherein each R' and R'' is the same or different and represents hydrogen or $C_{1-4}$ alkyl.

Preferred substituents on an carbocyclyl group include halogen, $C_{1-6}$ alkyl, $C_{1-6}$ alkoxy, $C_{1-6}$ alkylthio, $C_{1-6}$ haloalkyl, $C_{1-6}$ haloalkoxy, mono($C_{1-6}$ alkyl)amino, di($C_{1-6}$ alkyl)amino, nitro, cyano and oxo. Examples of preferred substituents on an carbocyclyl group include halogen, $C_{1-6}$ alkyl, $C_{1-6}$ alkoxy, $C_{1-6}$ alkylthio, $C_{1-6}$ haloalkyl, $C_{1-6}$ haloalkoxy, mono($C_{1-6}$ alkyl)amino, di($C_{1-6}$ alkyl)amino, nitro and cyano. Particularly preferred substituents include fluorine, chlorine, bromine, $C_{1-4}$ alkyl, $C_{1-4}$ alkoxy, $C_{1-4}$ haloalkyl, nitro and oxo. Examples of particularly preferred substituents include fluorine, chlorine, bromine, $C_{1-4}$ alkyl, $C_{1-4}$ alkoxy, $C_{1-4}$ haloalkyl and nitro. Further examples of particularly preferred substituents include fluorine, $C_{1-4}$ alkyl, $C_{1-4}$ alkoxy, $C_{1-4}$ haloalkyl and nitro.

As used herein, a heterocyclyl group is a non-aromatic saturated or unsaturated carbocyclic ring typically having from 5 to 10 carbon atoms, in which one or more, for example 1, 2 or 3, of the carbon atoms is replaced by a heteroatom selected from N, O and S. Saturated heterocyclyl groups are preferred. Examples include tetrahydrofuranyl, tetrahydrothienyl, pyrrolidinyl, imidazolidinyl, pyrazolidinyl, dioxolanyl, thiazolidinyl, tetrahydropyranyl, piperidinyl, dioxanyl, piperazinyl, morpholinyl, thiomorpholinyl and thioxanyl. Further examples include dithiolanyl, oxazolidinyl, tetrahydrothiopyranyl and dithianyl. Piperazinyl, piperidinyl and morpholinyl are preferred.

As used herein, references to a heterocyclyl group include fused ring systems in which a heterocyclyl group is fused to a phenyl group. Preferred such fused ring systems are those wherein a 5- to 6-membered heterocyclyl group is fused to a phenyl group. An example of such a fused ring system is a group wherein a 1H-imidazol-2(3H)-onyl group or a imidazolidin-2-onyl group is fused to a phenyl ring to form a 1H-benzo[d]imidazol-2(3H)-onyl group. Most preferably, however, a heterocyclyl group is monocyclic.

A heterocyclic group may be unsubstituted or substituted at any position. Typically, it carries 0, 1 or 2 substituents.

Suitable substituents on a heterocyclyl group include halogen, $C_{1-6}$ alkyl, $C_{2-7}$ acyl, hydroxy, $C_{1-6}$ alkoxy, $C_{1-6}$ alkylthio, $C_{1-6}$ haloalkyl, $C_{1-6}$ haloalkoxy, nitro, cyano, carbamoyl, mono($C_{1-6}$ alkyl)carbamoyl, di($C_{1-6}$ alkyl)carbomyl, amino, mono($C_{1-6}$ alkyl)amino, di($C_{1-6}$ alkyl)amino, oxo, —$CO_2R'$, —$CONR'R''$, —$S(O)R'$, —$S(O)_2R'$, —$S(O)NR'R''$, —$S(O)_2NR'R''$, —NH—$S(O)_2R'$ or —NH—CO—R', wherein each R' and R'' is the same or different and represents hydrogen or $C_{1-6}$ alkyl. Examples of suitable substitutents on a heterocyclyl group include halogen, $C_{1-6}$ alkyl, $C_{2-7}$ acyl, hydroxy, $C_{1-6}$ alkoxy, $C_{1-6}$ alkylthio, $C_{1-6}$ haloalkyl, $C_{1-6}$ haloalkoxy, nitro, cyano, carbamoyl, mono($C_{1-6}$ alkyl) carbamoyl, di($C_{1-6}$ alkyl)carbomyl, amino, mono($C_{1-6}$ alkyl)amino, di($C_{1-6}$ alkyl)amino, —$CO_2R'$, —$CONR'R''$, —$S(O)R'$, —$S(O)_2R'$, —$S(O)NR'R''$, —NH—$S(O)_2R'$ or —NH—CO—R', wherein each R' and R'' is the same or different and represents hydrogen or $C_{1-6}$ alkyl.

Preferred substituents on a heterocyclyl group include halogen, $C_{1-6}$ alkyl, $C_{1-6}$ alkoxy, $C_{1-6}$ alkylthio, $C_{1-6}$ haloalkyl, $C_{1-6}$ haloalkoxy, mono($C_{1-6}$ alkyl)amino, di($C_{1-6}$ alkyl)amino, nitro, cyano and oxo. Examples of preferred substituents on a heterocyclyl group include halogen, $C_{1-6}$ alkyl, $C_{1-6}$ alkoxy, $C_{1-6}$ alkylthio, $C_{1-6}$ haloalkyl, $C_{1-6}$ haloalkoxy, mono($C_{1-6}$ alkyl)amino, di($C_{1-6}$ alkyl)amino, nitro and cyano. Particularly preferred substituents include fluorine, chlorine, bromine, $C_{1-4}$ alkyl, $C_{1-4}$ alkoxy, $C_{1-4}$ haloalkyl, nitro and oxo. Examples of particularly preferred substituents include fluorine, chlorine, bromine, $C_{1-4}$ alkyl, $C_{1-4}$ alkoxy, $C_{1-4}$ haloalkyl and nitro. Further examples of particularly preferred substituents include fluorine, $C_{1-4}$ alkyl, $C_{1-4}$ alkoxy, $C_{1-4}$ haloalkyl and nitro. Most preferably, a heterocyclyl group is unsubstituted or substituted by one or two $C_{1-2}$ alkyl groups.

As used herein, a halogen is typically chlorine, fluorine, bromine or iodine. It is preferably chlorine, fluorine or bromine. It is more preferably chlorine or fluorine.

As used herein, an alkoxy group is typically a said alkyl group attached to an oxygen atom. An alkylthio group is typically a said alkyl group attached to a thio group. A haloalkyl or haloalkoxy group is typically a said alkyl or alkoxy group substituted by one or more said halogen atoms. Typically, it is substituted by 1, 2 or 3 said halogen atoms. Preferred haloalkyl and haloalkoxy groups include perhaloalkyl and perhaloalkoxy groups such as —$CX_3$ and —$OCX_3$ wherein X is a said halogen atom, for example chlorine or fluorine. Particularly preferred haloalkyl groups are —$CF_3$ and —$CCl_3$. Particularly preferred haloalkoxy groups are —$OCF_3$ and —$OCCl_3$.

As used herein, a heteroaryl group is typically a 5- to 10 membered aromatic ring, such as a 5- or 6-membered ring, containing at least one heteroatom, for example 1, 2 or 3 heteroatoms, selected from O, S and N. Examples include pyridyl, pyrazinyl, pyrimidinyl, pyridazinyl, furanyl, thienyl, pyrazolidinyl, pyrrolyl, oxadiazolyl, isoxazolyl, thiadiazolyl, thiazolyl, imidazolyl and pyrazolyl groups. Further examples include oxazolyl and isothiazolyl. Preferred heteroaryl groups are pyridyl, thienyl, oxazolyl, isoxazolyl, furanyl and pyrazolyl. Examples of preferred heteroaryl groups are pyridyl, thienyl, isoxazolyl and furanyl. As used herein, references to a heteroaryl groups include fused ring systems in which a heteroaryl group is fused to a phenyl group. Preferred such fused ring systems are those wherein a 5- to 6-membered heteroaryl group is fused to a phenyl group. Examples of such fused ring systems are benzofuranyl, benzothiophenyl, indolyl, benzimidazolyl, benzoxazolyl, quinolinyl, quinazolinyl and isoquinolinyl moieties. Most preferably, however, a heterocyclyl group is monocyclic.

A heteroaryl group may be unsubstituted or substituted at any position. Typically, it carries 0, 1, 2 or 3 substituents.

Suitable substituents on a heteroaryl group include halogen, $C_{1-6}$ alkyl, $C_{2-7}$ acyl, hydroxy, $C_{1-6}$ alkoxy, $C_{1-6}$ alkylthio, $C_{1-6}$ haloalkyl, $C_{1-6}$ haloalkoxy, nitro, cyano, carbamoyl, mono($C_{1-6}$ alkyl)carbamoyl, di($C_{1-6}$ alkyl)carbamoyl, amino, mono($C_{1-6}$ alkyl)amino, di($C_{1-6}$ alkyl)amino, —$CO_2R'$, —$CONR'R''$, —$S(O)R'$, —$S(O)_2R'$, —$S(O)NR'R''$, —$S(O)_2NR'R''$, —NH—$S(O)_2R'$ or —NH—CO—R', wherein each R' and R'' is the same or different and represents hydrogen or $C_{1-6}$ alkyl. Examples of suitable substitutents on a heteroaryl group include halogen, $C_{1-6}$ alkyl, $C_{2-7}$ acyl, hydroxy, $C_{1-6}$ alkoxy, $C_{1-4}$ alkylthio, $C_{1-6}$ haloalkyl, $C_{1-6}$ haloalkoxy, nitro, cyano, carbamoyl, mono($C_{1-6}$ alkyl)carbamoyl, di($C_{1-6}$ alkyl)carbamoyl, amino, mono($C_{1-6}$ alkyl)amino, di($C_{1-6}$ alkyl)amino, —$CO_2R'$, —$CONR'R''$, —$S(O)R'$, —$S(O)_2R'$, —$S(O)NR'R''$, —NH—$S(O)_2R'$ or —NH—CO—R', wherein each R' and R'' is the same or different and represents hydrogen or $C_{1-6}$ alkyl.

Preferred substituents on a heteroaryl group include halogen, $C_{1-6}$ alkyl, $C_{1-6}$ alkoxy, $C_{1-6}$ alkylthio, $C_{1-6}$ haloalkyl, $C_{1-6}$ haloalkoxy, mono($C_{1-6}$ alkyl)amino, di($C_{1-6}$ alkyl) amino, nitro and cyano. Particularly preferred substituents include fluorine, chlorine, bromine, $C_{1-4}$ alkyl, $C_{1-4}$ alkoxy, $C_{1-4}$ haloalkyl and nitro. Further preferred substituents include fluorine, chlorine, bromine, $C_{1-2}$ alkyl, $C_{1-2}$ haloalkyl and di($C_{1-2}$ alkyl)amino.

As used herein, references to a heteroaryl group include fused ring systems in which a heteroaryl group is fused to a monocyclic said aryl, carbocyclyl or heterocyclyl group, or to a further heteroaryl group. Preferred such ring systems are those wherein a heteroaryl group is fused to an aryl group, for example a phenyl group. An example of such a fused ring system is a group wherein a thienyl group is fused to a phenyl ring to form a benzothienyl group. A further example of such a fused ring system is a group wherein a furanyl group is fused to a phenyl ring to form a benzofuranyl group.

When $R^1$ in the formula (V) is an aryl or heteroaryl group it is typically unsubstituted or substituted by one, two or three substituents selected from halogen, $C_{1-6}$ alkyl, $C_{1-6}$ alkoxy, $C_{1-6}$ alkylthio, $C_{1-6}$ haloalkyl or $C_{1-6}$ haloalkoxy. Preferably, it is unsubstituted or substituted by one or two substituents selected from fluorine, chlorine, bromine, $C_{1-4}$ alkyl, $C_{1-4}$ alkoxy, $C_{1-4}$ alkylthio, $C_{1-4}$ haloalkyl or $C_{1-4}$ haloalkoxy. More preferably, it is unsubstituted or substituted by a single fluorine, chlorine, $C_{1-2}$ alkyl, $C_{1-2}$ alkoxy, $C_{1-2}$ alkylthio, $C_{1-2}$ haloalkyl or $C_{1-2}$ haloalkoxy substituent.

Typically, $R^1$ in the formula (V) is $C_{1-6}$ alkyl or aryl. Preferably, $R^1$ is $C_{1-2}$ alkyl or aryl. More preferably, $R^1$ is $C_{1-2}$ alkyl or phenyl. More preferably, $R^1$ is phenyl.

Typically, $R^2$ in the formula (V) is hydrogen or $C_{1-4}$ alkyl. Preferably, $R^2$ is hydrogen.

Typically, $R^3$ in the formula (V) is halogen, hydroxy, $C_{1-4}$ alkyl, $C_{1-4}$ alkoxy, $C_{1-4}$ alkylthio, $C_{1-4}$ haloalkyl, $C_{1-4}$ haloalkoxy, amino, mono($C_{1-4}$ alkyl)amino or di($C_{1-4}$ alkyl)amino. Preferably, $R^3$ is fluorine, chlorine, bromine, $C_{1-2}$ alkyl, $C_{1-2}$ alkoxy, $C_{1-2}$ alkylthio, $C_{1-2}$ haloalkyl, $C_{1-2}$ haloalkoxy, amino, mono($C_{1-2}$ alkyl)amino or di($C_{1-2}$ alkyl)amino. More preferably, $R^3$ is methyl, trifluoromethyl, fluorine, chlorine or bromine. Most preferably, $R^3$ is methyl or chlorine. An example of a most preferred group is when $R^3$ is chlorine.

Typically, n in the formula (V) is 0, 1 or 2. Preferably, n is 0 or 1.

Typically, $R^4$ in the formula (V) is hydrogen or $C_{1-4}$ alkyl. Preferably, $R^4$ is hydrogen or $C_{1-2}$ alkyl. More preferably, $R^4$ is hydrogen or methyl. Most preferably, $R^4$ is hydrogen.

When $R^5$ in the formula (V) is a heterocyclyl group, it is typically attached via a carbon atom. Typically, $R^5$ is $C_{1-6}$ alkyl, aryl, heteroaryl, carbocyclyl, heterocyclyl, aryl-($C_{1-4}$ alkyl)-, heteroaryl-($C_{1-4}$ alkyl)-, carbocyclyl-($C_{1-4}$ alkyl)-, heterocyclyl-($C_{1-4}$ alkyl)-, aryl-C(O)—C(O)—, heteroaryl-C(O)—C(O)— or —$XR^6$. Examples of typical $R^5$ groups are those wherein $R^5$ is $C_{1-6}$ alkyl, aryl, heteroaryl, carbocyclyl, heterocyclyl, aryl-($C_{1-4}$ alkyl)-, heteroaryl-($C_{1-4}$ alkyl)-, carbocyclyl-($C_{1-4}$ alkyl)-, heterocyclyl-($C_{1-4}$ alkyl)- or —$XR^6$.

Preferably, $R^5$ in the formula (V) is $C_{1-4}$ alkyl, aryl, for example phenyl and dihydrobenzofuranyl, heteroaryl, for example thienyl, furanyl, isoxazolyl, pyridyl and benzothienyl, carbocyclyl, for example cyclopentyl and cyclohexyl, heterocyclyl, for example piperidinyl, morpholinyl and piperazinyl, phenyl-($C_{1-2}$ alkyl)-, for example benzyl, heteroaryl-($C_{1-2}$ alkyl)-, phenyl-C(O)—C(O)-, heteroaryl-C(O)—C(O)— or —$XR^6$. Examples of preferred $R^5$ groups are those wherein $R^5$ is $C_{1-4}$ alkyl, aryl, for example phenyl and dihydrobenzofuranyl, heteroaryl, for example thienyl, furanyl, isoxazolyl, pyridyl and benzothienyl, carbocyclyl, for example cyclopentyl and cyclohexyl, heterocyclyl, for example piperidinyl, morpholinyl and piperazinyl, phenyl-($C_{1-2}$ alkyl)-, for example benzyl, heteroaryl-($C_{1-2}$ alkyl)- or —$XR^6$.

More preferably, $R^5$ in the formula (V) is $C_{1-4}$ alkyl, phenyl, thienyl, furanyl, isoxazolyl, pyridyl, cyclopentyl, cyclohexyl, benzothienyl, dihydrobenzofuranyl, phenyl-$CH_2$—, furanyl-$CH_2$—, phenyl-C(O)—C(O)—, thienyl-C(O)—C(O)— or —$XR^6$. Examples of more preferred $R^5$ groups are those wherein $R^5$ is $C_{1-4}$ alkyl, phenyl, thienyl, furanyl, isoxazolyl, pyridyl, cyclopentyl, cyclohexyl, benzothienyl, dihydrobenzofuranyl, phenyl-$CH_2$—, furanyl-$CH_2$— or —$XR^6$.

Most preferably, $R^5$ in the formula (V) is phenyl-$CH_2$—, furanyl-$CH_2$—, —C(O)—C(O)-thienyl or —$XR^6$. Examples of most preferred $R^5$ groups are those wherein $R^5$ is phenyl-$CH_2$—, furanyl-$CH_2$— or —XR'.

Typically, X in the formula (V) is —CO—, —S(O)— or —$S(O)_2$—. Preferably, X is —CO— or —$S(O)_2$—.

When $R^6$ in the formula (V) is a group —NR'R'' and either R' or R'' includes an aryl, heteroaryl, carbocyclyl or heterocyclyl moiety it is typically unsubstituted or substituted by 1, 2 or 3 substituents selected from halogen, $C_{1-6}$ alkyl, $C_{1-6}$ alkoxy, $C_{1-6}$ alkylthio, $C_{1-6}$ haloalkyl, $C_{1-6}$ haloalkoxy, nitro and cyano. Preferably, the aryl, heteroaryl, carbocyclyl or heterocyclyl moiety is unsubstituted or substituted by 1 or 2 substituents selected from fluorine, chlorine, bromine, $C_{1-4}$ alkyl, $C_{1-4}$ alkoxy, $C_{1-4}$ alkylthio, $C_{1-4}$ haloalkyl, $C_{1-4}$ haloalkoxy and nitro. An example of preferred substitution is when the aryl, heteroaryl, carbocyclyl or heterocyclyl moiety is unsubstituted or substituted by 1 or 2 substituents selected from fluorine, chlorine, bromine, $C_{1-4}$ alkyl, $C_{1-4}$ alkoxy, $C_{1-4}$ haloalkyl and nitro. More preferably, the aryl, heteroaryl, carbocyclyl or heterocyclyl moiety is unsubstituted or substituted by one or two substituents selected from fluorine, chlorine, bromine, $C_{1-2}$ alkyl, $C_{1-2}$ alkoxy, $C_{1-2}$ alkylthio, $C_{1-2}$ haloalkyl and nitro. An example of more preferred substitution is when the aryl, heteroaryl, carbocyclyl or heterocyclyl moiety is unsubstituted or substituted by a single fluoro, chloro, methyl, methoxy or nitro substituent. When R' or R'' is a heteroaryl or heterocyclyl group, it is attached via a carbon atom.

Typically, R' and R'' in the group —NR'R'' in the formula (V) are not both hydrogen. Typically, each R' and R'' is the same or different and represents hydrogen, $C_{1-4}$ alkyl, aryl, heteroaryl, carbocyclyl, aryl-($C_{1-4}$ alkyl)- or heteroaryl-($C_{1-4}$ alkyl)-. Examples of typical R' and R'' groups are those wherein each R' and R'' is the same or different and represents hydrogen, $C_{1-4}$ alkyl, phenyl, heteroaryl, for example thienyl, carbocyclyl, for example cyclohexyl or cyclopentyl, or phenyl-($C_{1-4}$ alkyl)-. Further examples of typical R' and R" groups are those wherein each R' and R" is the same or different and represents hydrogen, $C_{1-4}$ alkyl, phenyl, thienyl, cyclohexyl, cyclopentyl or phenyl-($CH_2$)—. Preferably, each R' and R" is the same or different and represents hydrogen, $C_{1-4}$ alkyl, phenyl, phenyl-$CH_2$—, cyclohexyl or cyclopentyl. More preferably, one of R' and R" represents hydrogen. Most preferably, one of R' and R" is hydrogen and the other is $C_{1-4}$ alkyl, phenyl, phenyl-$CH_2$—, cyclohexyl or cyclopentyl. As an additional preference, one of R' and R" is hydrogen and the other is $C_{1-4}$ alkyl, phenyl, thienyl or phenyl-$CH_2$—.

Typically, $R^6$ in the formula (V) is $C_{1-6}$ alkyl, hydroxy, $C_{1-6}$ alkoxy, $C_{1-6}$ alkylthio, aryl, heteroaryl, carbocyclyl, heterocyclyl, aryl-($C_{1-4}$ alkyl)-, heteroaryl-($C_{1-4}$ alkyl)-, carbocyclyl-($C_{1-4}$ alkyl)-, heterocyclyl-($C_{1-4}$ alkyl)-, aryl-($C_{1-4}$ hydroxyalkyl)-, heteroaryl-($C_{1-4}$ hydroxyalkyl)-, carbocyclyl-($C_{1-4}$ hydroxyalkyl)-, heterocyclyl-($C_{1-4}$ hydroxyalkyl)-, aryl-($C_{1-4}$ alkyl)-O—, heteroaryl-($C_{1-4}$ alkyl)-O—, carbocyclyl-($C_{1-4}$ alkyl)-O—, heterocyclyl-($C_{1-4}$ alkyl)-O— or —NR'R" wherein R' and R" are as defined above. Examples of typical $R^6$ groups are those wherein $R^6$ is $C_{1-6}$ alkyl, hydroxy, $C_{1-6}$ alkoxy, $C_{1-6}$ alkylthio, aryl, heteroaryl, carbocyclyl, heterocyclyl, aryl-($C_{1-4}$ alkyl)-, heteroaryl-($C_{1-4}$ alkyl)-, carbocyclyl-($C_{1-4}$ alkyl)-, heterocyclyl-($C_{1-4}$ alkyl)- or —NR'R" wherein R' and R" are as defined above.

Preferably, $R^6$ in the formula (V) is $C_{1-6}$ alkyl, $C_{1-6}$ alkoxy, $C_{1-6}$ alkylthio, aryl, for example phenyl, naphthyl, dihydrobenzofuranyl, benzodioxinyl, 9H-fluoren-9-onyl and indolyl, heteroaryl, for example thienyl, furanyl, oxazolyl, isoxazolyl, pyrazolyl, pyridyl, benzothienyl and benzofuranyl, carbocyclyl, for example cyclopentyl and cyclohexyl, heterocyclyl, for example piperazinyl, piperidinyl, morpholinyl and 1H-benzo[d<imidazol-2(3H)-onyl, phenyl-($C_{1-2}$ alkyl)-, phenyl-($C_{1-2}$ alkyl)-O—, phenyl-($C_{1-2}$ hydroxyalkyl)-, heteroaryl-($C_{1-2}$ hydroxyalkyl)-, heteroaryl-($C_{1-2}$ alkyl)- or —NR'R" wherein R' and R" are as defined above. Examples of preferred $R^6$ groups are those wherein $R^6$ is $C_{1-4}$ alkyl, aryl, for example phenyl and dihydrobenzofuranyl, heteroaryl, for example thienyl, furanyl, isoxazolyl, pyridyl and benzothienyl, carbocyclyl, for example cyclopentyl and cyclohexyl, heterocyclyl, for example N-heterocyclyl, phenyl-($C_{1-2}$ alkyl)-, for example benzyl, heteroaryl-($C_{1-2}$ alkyl)- or —NR'R" wherein R' and R" are as defined above.

More preferably, $R^6$ in the formula (V) is $C_{1-4}$ alkyl, $C_{1-4}$ alkoxy, phenyl, naphthyl, dihydrobenzofuranyl, benzodioxinyl, 9H-fluoren-9-onyl, indolyl, thienyl, furanyl, oxazolyl, isoxazolyl, pyrazolyl, pyridyl, benzothienyl, benzofuranyl, cyclopentyl, cyclohexyl, piperazinyl, piperidinyl, morpholinyl, phenyl-($C_{1-2}$ alkyl)-, phenyl-$CH_2$—CH(OH)—, phenyl-CH(OH)—$CH_2$—, phenyl-($C_{1-2}$ alkyl)-O—, 1H-benzo[d]imidazol-2(3H)-onyl or —NR'R" wherein R' and R" are as defined above. Example of most preferred $R^6$ groups are those wherein $R^6$ is $C_{1-4}$ alkyl, phenyl, thienyl, furanyl, pyridyl, cyclopentyl, cyclohexyl, benzothienyl, dihydrobenzofuranyl, isoxazolyl, piperidinyl, for example N-piperidinyl, morpholinyl, for example N-morpholinyl, piperazinyl, for example N-piperazinyl, or —NR'R" wherein R' and R" are as defined above.

Preferred compounds of the formula (V) are those in which:

$R^1$ is $C_{1-6}$ alkyl or aryl;

$R^2$ is hydrogen or $C_{1-4}$ alkyl;

$R^3$ is halogen, hydroxy, $C_{1-4}$ alkyl, $C_{1-4}$ alkoxy, $C_{1-4}$ alkylthio, $C_{1-4}$ haloalkyl, $C_{1-4}$ haloalkoxy, amino, mono($C_{1-4}$ alkyl)amino or di($C_{1-4}$ alkyl)amino or, preferably, $R^3$ is fluorine, chlorine, bromine, $C_{1-2}$ alkyl, $C_{1-2}$ alkoxy, $C_{1-2}$ alkylthio, $C_{1-2}$ haloalkyl, $C_{1-2}$ haloalkoxy, amino, mono($C_{1-2}$ alkyl)amino or di($C_{1-2}$ alkyl)amino;

n is 0, 1 or 2;

$R^4$ is hydrogen or $C_{1-4}$ alkyl;

$R^5$ is $C_{1-6}$ alkyl, aryl, heteroaryl, carbocyclyl, heterocyclyl, aryl-($C_{1-4}$ alkyl)-, heteroaryl-($C_{1-4}$ alkyl)-, carbocyclyl-($C_{1-4}$ alkyl)-, heterocyclyl-($C_{1-4}$ alkyl)-, aryl-C(O)—C(O)—, heteroaryl-C(O)—C(O)— or —$XR^6$;

X is —CO—, —S(O)— or —S(O)$_2$—; and $R^6$ is $C_{1-6}$ alkyl, hydroxy, $C_{1-6}$ alkoxy, $C_{1-6}$ alkylthio, aryl, heteroaryl, carbocyclyl, heterocyclyl, aryl-($C_{1-4}$ alkyl)-, heteroaryl-($C_{1-4}$ alkyl)-, carbocyclyl-($C_{1-4}$ alkyl)-, heterocyclyl-($C_{1-4}$ alkyl)-, aryl-($C_{1-4}$ hydroxyalkyl)-, heteroaryl-($C_{1-4}$ hydroxyalkyl)-, carbocyclyl-($C_{1-4}$ hydroxyalkyl)-, heterocyclyl-($C_{1-4}$ hydroxyalkyl)-, aryl-($C_{1-4}$ alkyl)-O—, heteroaryl-($C_{1-4}$ alkyl)-O—, carbocyclyl-($C_{1-4}$ alkyl)-O—, heterocyclyl-($C_{1-4}$ alkyl)-O— or —NR'R", wherein each R' and R" is the same or different and represents hydrogen, $C_{1-4}$ alkyl, aryl, heteroaryl, carbocyclyl, aryl-($C_{1-4}$ alkyl)- or heteroaryl-($C_{1-4}$ alkyl)-, the aryl moiety in the $R^1$ group being unsubstituted or substituted by 1, 2 or 3 substituents selected from halogen, $C_{1-6}$ alkyl, $C_{1-6}$ alkoxy, $C_{1-6}$ alkylthio, $C_{1-6}$ haloalkyl or $C_{1-6}$ haloalkoxy;

the aryl and heteroaryl moieties in the groups $R^5$ and $R^6$ being unsubstituted or substituted by 1, 2 or 3 substituents selected from halogen, $C_{1-6}$ alkyl, $C_{2-7}$ acyl, hydroxy, $C_{1-6}$ alkoxy, $C_{1-6}$ alkylthio, $C_{1-6}$ haloalkyl, $C_{1-6}$ haloalkoxy, nitro, cyano, carbamoyl, mono($C_{1-6}$ alkyl)carbamoyl, di($C_{1-6}$ alkyl)carbomyl, amino, mono($C_{1-6}$ alkyl)amino, di($C_{1-6}$ alkyl)amino, —$CO_2R'$, —CONR'R", —S(O)R', —$S(O)_2R'$, —S(O)NR'R", —$S(O)_2NR'R"$, —NH—$S(O)_2R"$ or —NH—CO—R', wherein each R' and R" is the same or different and represents hydrogen or $C_{1-6}$ alkyl;

the carbocyclyl and heterocyclyl moieties in the groups $R^5$ and $R^6$ being unsubstituted or substituted by 1, 2 or 3 substituents selected from halogen, $C_{1-6}$ alkyl, $C_{2-7}$ acyl, hydroxy, $C_{1-6}$ alkoxy, $C_{1-6}$ alkylthio, $C_{1-6}$ haloalkyl, $C_{1-6}$ haloalkoxy, nitro, cyano, carbamoyl, mono($C_{1-6}$ alkyl)carbamoyl, di($C_{1-6}$ alkyl)carbomyl, amino, mono($C_{1-6}$ alkyl)amino, di($C_{1-6}$ alkyl)amino, oxo, —$CO_2R'$, —CONR'R", —S(O)R', —$S(O)_2R'$, —S(O)NR'R", —$S(O)_2NR'R"$, —NH—$S(O)_2R'$ or —NH—CO—R', wherein each R' and R" is the same or different and represents hydrogen or $C_{1-6}$ alkyl; and the alkyl moieties in the aryl-($C_{1-4}$ alkyl)-, heteroaryl-($C_{1-4}$ alkyl)-, carbocyclyl-($C_{1-4}$ alkyl)-, heterocyclyl-($C_{1-4}$ alkyl)- groups of $R^6$ being unsubstituted or substituted by one or two hydroxy substituents.

Preferably, in these preferred compounds of formula (V), the aryl, heteroaryl and carbocyclyl moieties in the groups R' and R" are unsubstituted or substituted by 1, 2 or 3 substituents selected from halogen, $C_{1-6}$ alkyl, $C_{1-6}$ alkoxy, $C_{1-6}$ alkylthio, C-6 haloalkyl, $C_{1-6}$ haloalkoxy, nitro and cyano.

Further preferred compounds of formula (V) are those wherein:

$R^1$ is $C_{1-2}$ alkyl or phenyl;

$R^2$ is hydrogen or $C_{1-4}$ alkyl;

$R^3$ is methyl, trifluoromethyl, fluorine, chlorine or bromine;

n is 0 or 1;

$R^4$ is hydrogen or $C_{1-2}$ alkyl;

$R^5$ is $C_{1-4}$ alkyl, aryl, for example phenyl and dihydrobenzofuranyl, heteroaryl, for example thienyl, furanyl, isoxazolyl, pyridyl and benzothienyl, carbocyclyl, for example cyclopentyl and cyclohexyl, heterocyclyl, for example piperidinyl, morpholinyl and piperazinyl, phenyl-($C_{1-2}$ alkyl)-, for example benzyl, heteroaryl-($C_{1-2}$ alkyl)-, phenyl-C(O)—C(O)—, heteroaryl-C(O)—C(O)— or —$XR^6$, provided that when $R^5$ is heterocyclyl it is attached via a carbon atom;

X is —CO—, —S(O)— or —S(O)$_2$—; and $R^6$ is $C_{1-6}$ alkyl, $C_{1-6}$ alkoxy, $C_{1-6}$ alkylthio, aryl, for example phenyl, naphthyl, dihydrobenzofuranyl, benzodioxinyl, 9H-fluoren-9-onyl and indolyl, heteroaryl, for example thienyl, furanyl, oxazolyl, isoxazolyl, pyrazolyl, pyridyl, benzothienyl and benzofuranyl, carbocyclyl, for example cyclopentyl and cyclohexyl, heterocyclyl, for example piperazinyl, piperidinyl, morpholinyl and 1H-benzo[d]imidazol-2(3H)-onyl, phenyl-($C_{1-2}$ alkyl)-, phenyl-($C_{1-2}$ alkyl)-O—, phenyl-($C_{1-2}$ hydroxyalkyl)-, heteroaryl-($C_{1-2}$ hydroxyalkyl)-, heteroaryl-($C_{1-2}$ alkyl)- or —NR'R" wherein each R' and R" is the same or different and represents hydrogen, $C_{1-4}$ alkyl, phenyl, heteroaryl, for example thienyl, carbocyclyl, for example cyclohexyl or cyclopentyl, or phenyl-($C_{1-4}$ alkyl)-, the phenyl moiety in the $R^1$ group being unsubstituted or substituted by one or two substituents selected from fluorine, chlorine, bromine, $C_{1-4}$ alkyl, $C_{1-4}$ alkoxy, $C_{1-4}$ alkylthio, $C_{1-4}$ haloalkyl or $C_{1-4}$ haloalkoxy;

the aryl moieties in the groups $R^5$ and $R^6$ being unsubstituted or substituted by 1, 2 or 3 substituents selected from halogen, $C_{1-6}$ alkyl, $C_{2-7}$ acyl, hydroxy, $C_{1-6}$ alkoxy, $C_{1-6}$ alkylthio, $C_{1-6}$ haloalkyl, $C_{1-6}$ haloalkoxy, amino, mono($C_{1-6}$ alkyl)amino, di($C_{1-6}$ alkyl)amino, nitro, cyano, —CO$_2$R', —S(O)R', —S(O)$_2$R' and —S(O)$_2$NR'R", wherein each R' and R" is the same or different and represents hydrogen or $C_{1-4}$ alkyl;

the heteroaryl moieties in the groups $R^5$ and $R^6$ being unsubstituted or substituted by 1, 2 or 3 substituents selected from halogen, $C_{1-6}$ alkyl, $C_{1-6}$ alkoxy, $C_{1-6}$ alkylthio, $C_{1-6}$ haloalkyl, $C_{1-6}$ haloalkoxy, mono($C_{1-6}$ alkyl)amino, di($C_{1-6}$ alkyl)amino, nitro and cyano; and the carbocyclyl and heterocyclyl moieties in the groups $R^5$ and $R^6$ being unsubstituted or substituted by 1, 2 or 3 substituents selected from halogen, $C_{1-6}$ alkyl, $C_{1-6}$ alkoxy, $C_{1-6}$ alkylthio, $C_{1-6}$ haloalkyl, $C_{1-6}$ haloalkoxy, mono($C_{1-6}$ alkyl) amino, di($C_{1-6}$ alkyl)amino, nitro, cyano and oxo; and the alkyl moiety in the phenyl-($C_{1-2}$ alkyl)- and heteroaryl-($C_{1-2}$ alkyl)- groups of $R^6$ being unsubstituted or substituted by a single hydroxy substituent.

Preferably, in these further preferred compounds of formula (V), the phenyl, heteroaryl and carbocyclyl moieties in the groups R' and R" are unsubstituted or substituted by 1 or 2 substituents selected from fluorine, chlorine, bromine, $C_{1-4}$ alkyl, $C_{1-4}$ alkoxy, $C_{1-4}$ alkylthio, $C_{1-4}$ haloalkyl, $C_{1-4}$ haloalkoxy and nitro.

Particularly preferred compounds of formula (V) are compounds of formula (Va) are pharmaceutically acceptable salts thereof

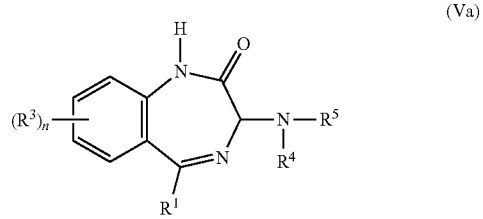

wherein:

$R^1$ is phenyl or methyl;

$R^3$ is methyl or chlorine;

n is 0 or 1;

$R^4$ is hydrogen or methyl;

$R^5$ is phenyl-CH$_2$—, furanyl-CH$_2$—, thienyl-C(O)—C(O)— or —$XR^6$;

X is —CO— or —S(O)$_2$—; and $R^6$ is $C_{1-4}$ alkyl, $C_{1-4}$ alkoxy, phenyl, naphthyl, dihydrobenzofuranyl, benzodioxinyl, 9H-fluoren-9-onyl, indolyl, thienyl, furanyl, oxazolyl, isoxazolyl, pyrazolyl, pyridyl, benzothienyl, benzofuranyl, cyclopentyl, cyclohexyl, piperazinyl, piperidinyl, morpholinyl, phenyl-($C_{1-2}$ alkyl)-, phenyl-CH$_2$—CH(OH)—, phenyl-CH(OH)—CH$_2$—, phenyl-($C_{1-2}$ alkyl)-O—, 1H-benzo[d]imidazol-2(3H)-onyl or —NR'R" wherein each R' and R" is the same or different and represents hydrogen, $C_{1-4}$ alkyl, phenyl, thienyl, cyclohexyl, cyclopentyl or phenyl-(CH$_2$)—, the phenyl moiety in the group R' being unsubstituted or substituted by a single fluorine, chlorine, $C_{1-2}$ alkyl, $C_{1-2}$ alkoxy, $C_{1-2}$ alkylthio, $C_{1-2}$ haloalkyl or $C_{1-2}$ haloalkoxy substituent;

the aryl moieties in the groups $R^5$ and $R^6$ being unsubstituted or substituted by 1,2 or 3 substituents selected from fluorine, chlorine, bromine, iodine, $C_{1-4}$ alkyl, $C_{2-4}$ acyl, hydroxy, $C_{1-4}$ alkoxy, $C_{1-4}$ alkylthio, $C_{1-4}$ haloalkyl, $C_{1-4}$ haloalkoxy, amino, mono($C_{1-4}$ alkyl)amino, di($C_{1-4}$ alkyl) amino, nitro, —CO$_2$R', —S(O)$_2$R' and —S(O)$_2$NH$_2$, wherein R' represents $C_{1-2}$ alkyl;

the heteroaryl moieties in the groups $R^5$ and $R^6$ being unsubstituted or substituted by 1 or 2 substituents selected from fluorine, chlorine, bromine, $C_{1-2}$ alkyl, $C_{1-2}$ haloalkyl and di($C_{1-2}$ alkyl)amino; and the heterocyclyl and carbocyclyl moieties in the $R^6$ group being unsubstituted or substituted by 1 or 2 substituents selected from fluorine, chlorine, bromine, $C_{1-4}$ alkyl, $C_{1-4}$ alkoxy, $C_{1-4}$ haloalkyl and nitro.

Preferably, $R^1$ in the formula (Va) is phenyl, n is 0, $R^4$ is hydrogen and $R^5$ is —CO— phenyl or —CO—NH-phenyl, wherein the phenyl group in $R^5$ is unsubstituted or substituted by 1 or 2 substituents selected from fluorine, chlorine, $C_1$-$C_2$ alkyl, $C_1$-$C_2$ alkoxy, $C_1$-$C_2$ haloalkyl, —CO$_2$R' or —S(O)$_2$R', wherein each R' is the same or different and represents $C_1$-$C_2$ alkyl.

Compounds of the formulae (I), (II), (III) or (V) containing one or more chiral centre may be used in enantiomerically or diastereoisomerically pure form, or in the form of a mixture of isomers. For the avoidance of doubt, the chemical structures depicted herein are intended to embrace all stereoisomers of the compounds shown, including racemic and non-racemic mixtures and pure enantiomers and/or diastereoisomers.

Preferred compounds of the formula (V) are optically active isomers. Thus, for example, preferred compounds of formula (V) containing only one chiral centre include an R enantiomer in substantially pure form, an S enantiomer in substantially pure form and enantiomeric mixtures which contain an excess of the R enantiomer or an excess of the S enantiomer. For the avoidance of doubt, the compounds of the formula (V) can, if desired, be used in the form of solvates.

As used herein, a pharmaceutically acceptable salt is a salt with a pharmaceutically acceptable acid or base. Pharmaceutically acceptable acids include both inorganic acids such as hydrochloric, sulphuric, phosphoric, diphosphoric, hydrobromic or nitric acid and organic acids such as citric, fumaric, maleic, malic, ascorbic, succinic, tataric, benzoic, acetic, methanesulphonic, ethanesulphonic, benzenesulphonic or p-toluenesulphonic acid. Pharmaceutical acceptable bases include alkali metal (e.g. sodium or potassium) and alkaline earth metal (e.g. calcium or magnesium) hydroxides and organic bases such as alkyl amines, aralkyl amines or heterocyclic amines.

Most preferably, component (b) is:

N-(2-Oxo-5-phenyl-2,3-dihydro-1H-benzo[e][1,4]diazepin-3-yl)-acetamide;
1,1-Diethyl-3-(2-oxo-5-phenyl-2,3-dihydro-1H-benzo[e][1,4]diazepin-3-yl)-urea;
N-(2-Oxo-5-phenyl-2,3-dihydro-1H-benzo[e][1,4]diazepin-3-yl)-propionamide;
N-(2-Oxo-5-phenyl-2,3-dihydro-1H-benzo[e][1,4]diazepin-3-yl)-butyramide;
N-(2-Oxo-5-phenyl-2,3-dihydro-1H-benzo[e][1,4]diazepin-3-yl)-isobutyramide;
2,2-Dimethyl-N-(2-Oxo-5-phenyl-2,3-dihydro-1H-benzo[e][1,4]diazepin-3-yl)-propionamide;
Cyclopentanecarboxylic acid (2-oxo-5-phenyl-2,3-dihydro-1Hbenzo[e][1,4]diazepin-3-yl)-amide;
Cyclohexanecarboxylic acid 2-oxo-5-phenyl-2,3-dihydro-1H-benzo[e][1,4]diazepin-3-yl)-amide;
3-Methoxy N-(2-oxo-5-phenyl-2,3-dihydro-1H-benzo[e][1,4]diazepin-3-yl)-benzamide;
4-Methoxy N-(2-oxo-5-phenyl-2,3-dihydro-1H-benzo[e][1,4]diazepin-3-yl)-benzamide;
2-Methoxy N-(2-oxo-5-phenyl-2,3-dihydro-1H-benzo[e][1,4]diazepin-3-yl)-benzamide;
N-(2-Oxo-5-phenyl-2,3-dihydro-1H-benzo[e][1,4]diazepin-3-yl)-3-trifluoromethyl-benzamide;
N-(2-Oxo-5-phenyl-2,3-dihydro-1H-benzo[e][1,4]diazepin-3-yl)-benzamide;
Thiophene-2-carboxylic acid (2-oxo-5-phenyl-2,3-dihydro-1H-benzo[e][1,4]diazepin-3-yl)-3-amide;
Furan-2-carboxylic acid (2-oxo-5-phenyl-2,3-dihydro-1H-benzo[e][1,4]diazepin-3-yl)-amide;
Piperidine-1-carboxylic acid (2-oxo-5-phenyl-2,3-dihydro-1H-benzo[e][1,4]diazepin-3-yl)-amide;
Morpholine-4-carboxylic acid (2-oxo-5-phenyl-2,3-dihydro-1H-benzo[e][1,4]diazepin-3-yl)-amide;
4-Nitro-N-(2-oxo-5-phenyl-2,3-dihydro-1H-benzo[e][1,4]diazepin-3-yl)-benzamide;
3-Nitro-N-(2-oxo-5-phenyl-2,3-dihydro-1H-benzo[e][1,4]diazepin-3-yl)-benzamide;
4-Methyl-piperazine-1-carboxylic acid-(2-oxo-5-phenyl-2,3-dihydro-1H-benzo[e][1,4]diazepin-3-yl)-amide;
3,4-Dichloro-N-(2-oxo-5-phenyl-2,3-dihydro-1H-benzo[e][1,4]diazepin-3-yl)-benzamide;
N-(2-oxo-5-phenyl-2,3-dihydro-1H-benzo[e][1,4]diazepin-3-yl)-2-trifluoromethyl-benzamide;
4-Bromo-N-(2-oxo-5-phenyl-2,3-dihydro-1H-benzo[e][1,4]diazepin-3-yl)-benzamide;
2-Methyl-N-(2-oxo-5-phenyl-2,3-dihydro-1H-benzo[e][1,4]diazepin-3-yl)-benzamide;
2-Chloro-N-(2-oxo-5-phenyl-2,3-dihydro-1H-benzo[e][1,4]diazepin-3-yl)-benzamide;
2-Nitro-N-(2-oxo-5-phenyl-2,3-dihydro-1H-benzo[e][1,4]diazepin-3-yl)-benzamide;
2-Methoxy-4-nitro-N-(2-oxo-5-phenyl-2,3-dihydro-1H-benzo[e][1,4]diazepin-3-yl)-benzamide;
(S)-2-Methoxy-4-nitro-N-(2-oxo-5-phenyl-2,3-dihydro-1H-benzo[e][1,4]diazepin-3-yl)-benzamide
Benzo[b]thiophene-3-carboxylic acid (2-oxo-5-phenyl-2,3-dihydro-1H-benzo[e][1,4]diazepin-3-yl)-amide;
2,3-Dihydro-benzofuran-5-carboxylic acid (2-oxo-5-phenyl-2,3-dihydro-1H-benzo[e][1,4]diazepin-3-yl)-amide;
Isoxazole-5-carboxylic acid (2-oxo-5-phenyl-2,3-dihydro-1H-benzo[e][1,4]diazepin-3-yl)-amide;
Benzo[b]thiophene-2-carboxylic acid (2-oxo-5-phenyl-2,3-dihydro-1H-benzo[e][1,4]diazepin-3-yl)-amide;
Thiophen-3-carboxylic acid (2-oxo-5-phenyl-2,3-dihydro-1H-benzo[e][1,4]diazepin-3-yl)-amide;
N-(2-Oxo-5-phenyl-2,3-dihydro-1H-benzo[e][1,4]diazepin-3-yl)-isonicotinamide;
N-(2-Oxo-5-phenyl-2,3-dihydro-1H-benzo[e][1,4]diazepin-3-yl)-nicotinamide;
N-(2-Oxo-5-phenyl-2,3-dihydro-1H-benzo[e][1,4]diazepin-3-yl)-methanesulfonamide;
Propane-1-sulfonic acid-(2-oxo-5-phenyl-2,3-dihydro-1H-benzo[e][1,4]diazepin-3-yl)-amide;
Butane-1-sulfonic acid-(2-oxo-5-phenyl-2,3-dihydro-1H-benzo[e][1,4]diazepin-3-yl)-amide;
2-Bromo-N-(2-oxo-5-phenyl-2,3-dihydro-1H-benzo[e][1,4]diazepin-3-yl)-benzenesulfonamide;
3-Bromo-N-(2-oxo-5-phenyl-2,3-dihydro-1H-benzo[e][1,4]diazepin-3-yl)-benzenesulfonamide;
4-Bromo-N-(2-oxo-5-phenyl-2,3-dihydro-1H-benzo[e][1,4]diazepin-3-yl)-benzenesulfonamide;
2-Fluoro-N-(2-oxo-5-phenyl-2,3-dihydro-1H-benzo[e][1,4]diazepin-3-yl)-benzenesulfonamide;
3-(2-Nitro-benzylamino)-5-phenyl-1,3-dihydro-benzo[e][1,4]diazepin-2-one;
3-(3-Nitro-benzylamino)-5-phenyl-1,3-dihydro-benzo[e][1,4]diazepin-2-one;
3-(4-Nitro-benzylamino)-5-phenyl-1,3-dihydro-benzo[e][1,4]diazepin-2-one;
3-(2-Methoxy-benzylamino)-5-phenyl-1,3-dihydro-benzo[e][1,4]diazepin-2-one;
3-(3-Methoxy-benzylamino)-5-phenyl-1,3-dihydro-benzo[e][1,4]diazepin-2-one;
5-Phenyl-3-(2-trifluoromethyl-benzylamino)-1,3-dihydro-benzo[e][1,4]diazepin-2-one;
5-Phenyl-3-(3-trifluoromethyl-benzylamino)-1,3-dihydro-benzo[e][1,4]diazepin-2-one;
5-Phenyl-3-(4-trifluoromethyl-benzylamino)-1,3-dihydro-benzo[e][1,4]diazepin-2-one;
3-[(Furan-2-ylmethyl)-amino]-5-phenyl-1,3-dihydro-benzo[e][1,4]diazepin-2-one;
N-(7-Chloro-2-oxo-5-phenyl-2,3-dihydro-1H-benzo[e][1,4]diazepin-3-yl)-acetamide;
N-(7-Chloro-2-oxo-5-phenyl-2,3-dihydro-1H-benzo[e][1,4]diazepin-3-yl)-isobutyramide;
N-(7-Chloro-2-oxo-5-phenyl-2,3-dihydro-1H-benzo[e][1,4]diazepin-3-yl)-methanesulfonamide;
Furan-2-carboxylic acid (7-chloro-2-oxo-5-phenyl-2,3-dihydro-1H-benzo[e][1,4]diazepin-3-yl)-amide;
Thiophene-2-carboxylic acid (7-chloro-2-oxo-5-phenyl-2,3-dihydro-1H-benzo[e][1,4]diazepin-3-yl)-amide;
Cyclohexanecarboxylic acid (7-Chloro-2-oxo-5-phenyl-2,3-dihydro-1H-benzo[e][1,4]diazepin-3-yl)-amide;
N-(7-Chloro-2-oxo-5-phenyl-2,3-dihydro-1H-benzo[e][1,4]diazepin-3-yl)-2-methoxy-benzamide;

N-(7-Chloro-2-oxo-5-phenyl-2,3-dihydro-1H-benzo[e][1,4]diazepin-3-yl)-4-methoxy-benzamide;
N-(7-Chloro-2-oxo-5-phenyl-2,3-dihydro-1H-benzo[e][1,4]diazepin-3-yl)-2-nitro-benzamide;
2-(2-Methoxy-phenyl)N-(2-oxo-5-phenyl-2,3-dihydro-1H-benzo[e][1,4]diazepin-3-yl)-acetamide;
2-(3-Methoxy-phenyl)N-(2-oxo-5-phenyl-2,3-dihydro-1H-benzo[e][1,4]diazepin-3-yl)-acetamide;
2-(4-Methoxy-phenyl)N-(2-oxo-5-phenyl-2,3-dihydro-1H-benzo[e][1,4]diazepin-3-yl)-acetamide;
2-(4-Nitro-phenyl)N-(2-oxo-5-phenyl-2,3-dihydro-1H-benzo[e][1,4]diazepin-3-yl)-acetamide;
2-(3-Nitro-phenyl)N-(2-oxo-5-phenyl-2,3-dihydro-1H-benzo[e][1,4]diazepin-3-yl)-acetamide;
N-(2-Oxo-5-phenyl-2,3-dihydro-1H-benzo[e][1,4]diazepin-3-yl)-2-(2-trifluoromethyl-phenyl)-acetamide;
N-(2-Oxo-5-phenyl-2,3-dihydro-1H-benzo[e][1,4]diazepin-3-yl)-2-(3-trifluoromethyl-phenyl)-acetamide;
N-(2-Oxo-5-phenyl-2,3-dihydro-1H-benzo[e][1,4]diazepin-3-yl)-2-(4-trifluoromethyl-phenyl)-acetamide;
1-(2-Methoxy-phenyl)-3-(2-oxo-5-phenyl-2,3-dihydro-1H-benzo[e][1,4]diazepin-3-yl)-urea;
1-(2-Nitro-phenyl)-3-(2-oxo-5-phenyl-2,3-dihydro-1H-benzo[e][1,4]diazepin-3-yl)-urea;
1-(2-Chloro-phenyl)-3-(2-oxo-5-phenyl-2,3-dihydro-1H-benzo[e][1,4]diazepin-3)-urea;
1-(4-Chloro-phenyl)-3-(2-oxo-5-phenyl-2,3-dihydro-1H-benzo[e][1,4]diazepin-3-yl)-urea;
1-(2-oxo-5-phenyl-2,3-dihydro-1H-benzo[e][1,4]diazepin-3-yl)-3-p-tolyl-urea;
1-(2-Fluoro-phenyl)-3-(2-oxo-5-phenyl-2,3-dihydro-1H-benzo[e][1,4]diazepin-3-yl)-urea;
1-(4-Fluoro-phenyl)-3-(2-oxo-5-phenyl-2,3-dihydro-1H-benzo[e][1,4]diazepin-3-yl)-urea;
(S)-1-(2-Fluoro-phenyl)-3-(2-oxo-5-phenyl-2,3-dihydro-1H-benzo[e][1,4]diazepin-3-yl)-urea;
4-Methanesulfonyl-2-methoxy-N-(2-oxo-5-phenyl-2,3-dihydro-1H-benzo[e][1,4]diazepin-3-yl)-benzamide;
(S)-4-Methanesulfonyl-2-methoxy-N-(2-oxo-5-phenyl-2,3-dihydro-1H-benzo[e][1,4]diazepin-3-yl)-benzamide;
5-Acetyl-2-ethoxy-N-(2-oxo-5-phenyl-2,3-dihydro-1H-benzo[e][1,4]diazepin-3-yl)-benzamide;
(S)-5-Acetyl-2-ethoxy-N-(2-oxo-5-phenyl-2,3-dihydro-1H-benzo[e][1,4]diazepin-3-yl)-benzamide;
6-Fluoro-4H-benzo[1,3]dioxine-8-carboxylic acid (2-oxo-5-phenyl-2,3-dihydro-1H-benzo[e][1,4]diazepin-3-yl)-amide;
(S)-6-Fluoro-4H-benzo[1,3]dioxine-8-carboxylic acid (2-oxo-5-phenyl-2,3-dihydro-1H-benzo[e][1,4]diazepin-3-yl)-amide;
(S)-2-Methoxy-N-(2-oxo-5-phenyl-2,3-dihydro-1H-benzo[e][1,4]diazepin-3-yl)-4-trifluoromethyl-benzamide;
2,4,5-Trifluoro-N-(2-oxo-5-phenyl-2,3-dihydro-1H-benzo[e][1,4]diazepin-3-yl)-benzamide;
(S)-2,4,5-Trifluoro-N-(2-oxo-5-phenyl-2,3-dihydro-1H-benzo[e][1,4]diazepin-3-yl)-benzamide;
2-Hydroxy-N-(2-oxo-5-phenyl-2,3-dihydro-1H-benzo[e][1,4]diazepin-3-yl)-benzamide;
(S)-2-Hydroxy-N-(2-oxo-5-phenyl-2,3-dihydro-1H-benzo[e][1,4]diazepin-3-yl)-benzamide;
1H-Indole-7-carboxylic acid (2-oxo-5-phenyl-2,3-dihydro-1H-benzo[e][1,4]diazepin-3-yl)-amide;
(S)-1H-Indole-7-carboxylic acid (2-oxo-5-phenyl-2,3-dihydro-1H-benzo[e][1,4]diazepin-3-yl)-amide;
3-Methoxy-naphthalene-2-carboxylic acid (2-oxo-5-phenyl-2,3-dihydro-1H-benzo[e][1,4]diazepin-3-yl)-amide;
(S)-3-Methoxy-naphthalene-2-carboxylic acid (2-oxo-5-phenyl-2,3-dihydro-1H-benzo[e][1,4]diazepin-3-yl)-amide;
N-[7-Chloro-5-(2-fluoro-phenyl)-2-oxo-2,3-dihydro-1H-benzo[e][1,4]diazepine-3-yl]-4-methoxoy-benzamide;
1-(2-Fluoro-benzyl)-3-(2-oxo-5-phenyl-2,3-dihydro-1H-benzo[e][1,4]diazepin-3-yl)-urea;
1-(4-Methoxy-benzyl)-3-(2-oxo-5-phenyl-2,3-dihydro-1H-benzo[e][1,4]diazepin-3-yl)-urea;
1-(3-Methyl-benzyl)-3-(2-oxo-5-phenyl-2,3-dihydro-1H-benzo[e][1,4]diazepin-3-yl)-urea;
1-(2-Oxo-5-phenyl-2,3-dihydro-1H-benzo[e][1,4]diazepin-3-yl)-3-(4-trifluoromethyl-phenyl)-urea;
4-Chloro-2-methoxy-N-(2-oxo-5-phenyl-2,3-dihydro-1H-benzo[e][1,4]diazepin-3-yl)-benzamide;
4-Methoxy-3-nitro-N-(2-oxo-5-phenyl-2,3dihydro-1H-benzo[e][1,4]diazepin-3-yl)benzamide;
3-Methoxy-2-nitro-N-(2-oxo-5-phenyl-2,3dihydro-1H-benzo[e][1,4]diazepin-3-yl)-benzamide;
5-Chloro-2-methoxy-N-(2-oxo-5-phenyl-2,3dihydro-1H-benzo[e][1,4]diazepin-3-yl)benzamide;
5-Fluoro-2-methoxy-N-(2-oxo-5-phenyl-2,3-dihydro-1H-benzo[e][1,4]diazepin-3-yl)-benzamide;
2-Methoxy-4-nitro-N-(2-oxo-5-phenyl-2,3-dihydro-1H-benzo[e][1,4]diazepin-3-yl)-benzamide;
5-Methoxy-2-nitro-N-(2-oxo-5-phenyl-2,3-dihydro-1H-benzo[e][1,4]diazepin-3-yl)-benzamide;
3-Methoxy-4-nitro-N-(2-oxo-5-phenyl-2,3-dihydro-1H-benzo[e][1,4]diazepin-3-yl)-benzamide;
3-(2-Methoxy-phenyl)-N-(2-oxo-5-phenyl-2,3-dihydro-1H-benzo[e][1,4]diazepin-3-yl)propionamide;
3-(3-Methoxy-phenyl)-N-(2-oxo-5-phenyl-2,3-dihydro-1H-benzo[e][1,4]diazepin-3-yl)-propionamide;
3-(4-Methoxy-phenyl)-N-(2-oxo-5-phenyl-2,3-dihydro-1H-benzo[e][1,4]diazepin-3-yl)-propionamide;
N-[5-(3-Chloro-phenyl)-2-oxo-2,3-dihydro-1H-benzo[e][1,4]diazepin-3-yl]-2-methoxy-benzamide;
N-[5-(3-Chloro-phenyl)-2-oxo-5-phenyl-2,3-dihydro-1H-benzo[e][1,4]diazepin-3-yl]-4-methoxy-benzamide;
N-[5-(3-Chloro-phenyl)-2-oxo-5-phenyl-2,3-dihydro-1H-benzo[e][1,4]diazepin-3-yl]-2-nitro-benzamide;
N-[5-(3-Chloro-phenyl)-2-oxo-5-phenyl-2,3-dihydro-1H-benzo[e][1,4]diazepin-3-yl]-4-nitro-benzamide;
4-Methoxy-N-[2-oxo-5-(4-trifluoromethyl-phenyl)-2,3-dihydro-1H-benzo[e][1,4]diazepin-3-yl]-benzamide;
2-Methoxy-N-[2-oxo-5-(3-trifluoromethyl-phenyl)-2,3-dihydro-1H-benzo[e][1,4]diazepin-3-yl]-benzamide;
4-Methoxy-N-[2-oxo-5-(3-trifluoromethyl-phenyl)-2,3-dihydro-1H-benzo[e][1,4]diazepin-3-yl]-benzamide;
2-Ethoxy-N-(2-oxo-5-phenyl-2,3-dihydro-1H-benzo[e][1,4]diazepin-3-yl)-benzamide;
2,4-Dimethoxy-N-(2-oxo-5-phenyl-2,3-dihydro-1H-benzo[e][1,4]diazepin-3-yl)-benzamide;
2-Bromo-5-methoxy-N-(2-oxo-5-phenyl-2,3-dihydro-1H-benzo[e][1,4]diazepin-3-yl)-benzamide;
2-Methoxy-N-[5-(3-mehtoxy-phenyl)-2-oxo-2,3-dihydro-1H-benzo[e][1,4]diazepin-3-yl]-benzamide
N-[5-(3-Methoxy-phenyl)-2-oxo-5-phenyl-2,3-dihydro-1H-benzo[e][1,4]diazepin-3-yl]4-nitro-benzamide;
2-Methoxy-N-(8-methyl-2-oxo-5-phenyl-2,3-dihydro-1H-benzo[e][1,4]diazepin-3-yl)-benzamide;
2-Chloro-4-methanesulfonyl-N-(2-oxo-5-phenyl-2,3-dihydro-1H-benzo[e][1,4]diazepin-3-yl)-benzamide;
2-Dimethylamino-N-(2-oxo-5-phenyl-2,3-dihydro-1H-benzo[e][1,4]diazepin-3-yl)-benzamide;
(2-Oxo-5-phenyl-2,3-dihydro-1H-benzo[e][1,4]diazepin-3-yl)-carbaric acid benzyl ester;

1-(3,5-Dimethyl-phenyl)-3-(2-oxo-5-phenyl-2,3-dihydro-1H-benzo[e][1,4]diazepin-3-yl)-urea;
1-(2-Oxo-5-phenyl-2,3-dihydro-1H-benzo[e][1,4]diazepin-3-yl)-3-(4-trifluoromethoxy-phenyl)-urea;
1-(4-Bromo-2-trifluoromethyl-phenyl)-3-(2-oxo-5-phenyl-2,3-dihydro-1H-benzo[e][1,4]diazepin-3-yl)-urea;
1-(4-Bromo-benzyl)-3-(2-oxo-5-phenyl-2,3-dihydro-1H-benzo[e][1,4]diazepin-3-yl)-urea;
1-(2,3-Dichloro-phenyl)-3-(2-oxo-5-phenyl-2,3-dihydro-1H-benzo[e][1,4]diazepin-3-yl)-urea;
1-(2,6-Dimethyl-phenyl)-3-2-oxo-5-phenyl-2,3-dihydro-1H-benzo[e][1,4]diazepin-3-yl)-urea;
1-(2-Chloro-6-methyl-phenyl)-3-(2-oxo-5-phenyl-2,3-dihydro-1H-benzo[e][1,4]diazepin-3-yl)-urea;
1-(4-Nitro-phenyl)-3-(2-oxo-5-phenyl-2,3-dihydro-1H-benzo[e][1,4]diazepin-3-yl)-urea;
1-(2-Methylsulfanyl-phenyl)-3-(2-oxo-5-phenyl-2,3-dihydro-1H-benzo[e][1,4]diazepin-3-yl)-urea;
1-(2,6-Dichloro-phenyl)-3-(2-oxo-5-phenyl-2,3-dihydro-1H-benzo[e][1,4]diazepin-3-yl)-urea;
5-tert-Butyl-2-methoxy-N-(2-oxo-5-phenyl-2,3-dihydro-1H-benzo[e][1,4]diazepin-3-yl)-benzamide;
2,5-Dimethoxy-N-(2-oxo-5-phenyl-2,3-dihydro-1H-benzo[e][1,4]diazepin-3-yl)-benzamide;
1-(2,6-Difluoro-phenyl)-3-(2-oxo-5-phenyl-2,3-dihydro-1H-benzo[e][1,4]diazepin-3-yl)-urea;
1-(3-Fluoro-phenyl)-3-(2-oxo-5-phenyl-2,3-dihydro-1H-benzo[e][1,4]diazepin-3-yl)-urea;
1-(3-Methoxy-phenyl)-3-(2-oxo-5-phenyl-2,3-dihydro-1H-benzo[e][1,4]diazepin-3-yl)-urea;
1-(2-Oxo-5-phenyl-2,3-dihydro-1H-benzo[e][1,4]diazepin-3-yl)-3-(3-trifluoromethyl-phenyl)-urea;
1-(3-Chloro-phenyl)-3-(2-oxo-5-phenyl-2,3-dihydro-1H-benzo[e][1,4]diazepin-3-yl)-urea;
2-Methoxy-4-methylsulfanyl-N-(2-oxo-5-phenyl-2,3-dihydro-1H-benzo[e][1,4]diazepin-3-yl)-benzamide;
4-Methanesulfonyl-N-(2-oxo-5-phenyl-2,3-dihydro-1H-benzo[e][1,4]diazepin-3-yl)-benzamide;
N-(2-Oxo-5-phenyl-2,3-dihydro-1H-benzo[e][1,4]diazepin-3-yl)terephthalamic acid methyl ester;
2-Fluoro-N-(2-oxo-5-phenyl-2,3-dihydro-1H-benzo[e][1,4]diazepin-3-yl)-benzamide;
2,6-Difluoro-N-(2-oxo-5-phenyl-2,3-dihydro-1H-benzo[e][1,4]diazepin-3-yl)-benzamide;
N-(2-Oxo-5-phenyl-2,3-dihydro-1H-benzo[e][1,4]diazepin-3-yl)-2-propoxy-benzamide;
2-Iodo-N-(2-oxo-5-phenyl-2,3-dihydro-1H-benzo[e][1,4]diazepin-3-yl)-benzamide;
3-Methoxy-N-(2-oxo-5-phenyl-2,3-dihydro-1H-benzo[e][1,4]diazepin-3-yl)-terephthalamic acid methyl ester;
4-Amino-5-chloro-2-methoxy-N-(2-oxo-5-phenyl-2,3-dihydro-1H-benzo[e][1,4]diazepin-3-yl)-benzamide;
1-(2-Oxo-5-phenyl-2,3-dihydro-1H-benzo[e][1,4]diazepin-3-yl)-3-m-tolyl-urea;
2-Methylsulfanyl-N-(2-oxo-5-phenyl-2,3-dihydro-1H-benzo[e][1,4]diazepin-3-yl)-benzamide;
2-Methoxy-N-(2-oxo-5-phenyl-2,3-dihydro-1H-benzo[e][1,4]diazepin-3-yl)-5-sulfamoyl-benzamide;
2-Hydroxy-N-(2-oxo-5-phenyl-2,3-dihydro-1H-benzo[e][1,4]diazepin-3-yl)-3-phenyl-propionamide
3-Hydroxy-N-(2-oxo-5-phenyl-2,3-dihydro-1H-benzo[e][1,4]diazepin-3-yl)-3-phenyl-propionamide
3-(2-Fluoro-phenyl)-1-methyl-1-(2-oxo-5-phenyl-2,3-dihydro-1H-benzo[e][1,4]diazepin-3-yl)-urea;
2-Methoxy-N-methyl-4-nitro-N-(2-oxo-5-phenyl-2,3-dihydro-1H-benzo[e][1,4]diazepin-3-yl)-benzamide;

1-tert-Butyl-3-(2-oxo-5-phenyl-2,3-dihydro-1H-benzo[e][1,4]diazepin-3-yl)-urea;
1-Cycloheyl-3-(2-oxo-5-phenyl-2,3-dihydro-1H-benzo[e][1,4]diazepin-3-yl)-urea;
1-Ethyl-3-(2-oxo-5-phenyl-2,3-dihydro-1H-benzo[e][1,4]diazepin-3-yl)-urea;
1-Butyl-3-(2-oxo-5-phenyl-2,3-dihydro-1H-benzo[e][1,4]diazepin-3-yl)-urea;
4,5-Dimethyl-furan-2-carboxylic acid (2-oxo-5-phenyl-2,3-dihydro-1H-benzo[e][1,4]diazepin-3-yl)amide;
Piperidine-1-carboxylic acid (7-chloro-2-oxo-5-phenyl-2,3-dihydro-1H-benzo[e][1,4]diazepin-3-yl)-amide;
N-[5-(3-Chloro-phenyl)-2-oxo-5-phenyl-2,3-dihydro-1H-benzo[e][1,4]diazepin-3-yl)acetamide;
N-[5-(3-Chloro-phenyl)-2-oxo-5-phenyl-2,3-dihydro-1H-benzo[e][1,4]diazepin-3-isobutyramide;
Furan-2-carboxylic acid [5-(3-chloro-phenyl)-2-oxo-5-phenyl-2,3-dihydro-1H-benzo[e][1,4]diazepin-3-yl]-amide;
Thiophene-2-carboxylic acid [5-(3-chloro-phenyl)-2-oxo-5-phenyl-2,3-dihydro-1H-benzo[e][1,4]diazepin-3-yl]-amide;
Cyclohexanecarboxylic acid [5-(3chloro-phenyl)-2-oxo-5-phenyl-2,3-dihydro-1H-benzo[e][1,4]diazepin-3-yl]-amide;
Piperidine-1-carboxylic acid [5-(3-chloro-phenyl)-2-oxo-5-phenyl-2,3-dihydro-1H-benzo[e][1,4]diazepin-3-yl]-amide;
N-[5-(3-Chloro-phenyl)-2-oxo-5-phenyl-2,3-dihydro-1H-benzo[e][1,4]diazepin-3-yl]isonicotinamide;
5-Methyl-furan-2-carboxylic acid (2-oxo-5-phenyl-2,3-dihydro-1H-benzo[e][1.4]diazepin-3-yl)-amide;
Pyrazine-2-carboxylic acid (2-oxo-5-phenyl-2,3-dihydro-1H-benzo[e][1,4]diazepin-3-yl)-amide;
N-[5-(3-Methoxy-phenyl)-2-oxo-5-phenyl-2,3-dihydro-1H-benzo[e][1,4]diazepin-3-yl]-isobutyramide;
Thiophene-2-carboxylic acid [5-(3-methoxy-phenyl)-2-oxo-5-phenyl-2,3-dihydro-1H-benzo[e][1,4]diazepin-3-yl]-amide;
Cyclohexanecarboxylic acid [5-(3-methoxy-phenyl)-2-oxo-5-phenyl-2,3-dihydro-1H-benzo[e][1,4]diazepin-3-yl]-amide;
Piperidine-1-carboxylic acid [5-(3-methoxy-phenyl)-2-oxo-5-phenyl-2,3-dihydro-1H-benzo[e][1,4]diazepin-3-yl]-amide;
Piperidine-4-carboxylic acid [5-(3-methoxy-phenyl)-2-oxo-5-phenyl-2,3-dihydro-1H-benzo[e][1,4]diazepin-3-yl]-amide;
Cyclohexanecarboxylic acid (8-chloro-2-oxo-5-phenyl-2,3-dihydro-1H-benzo[e][1,4]diazepin-3-yl)-amide;
Thiophene-2-carboxylic acid (8-methyl-2-oxo-5-phenyl-2,3-dihydro-1H-benzo[e][1,4]diazepin-3-yl)-amide;
1-(2-Oxo-5-phenyl-2,3-dihydro-1H-benzo[e][1,4]diazepin-3-yl)-3-thiophene-2-yl-urea;
1-(2-Oxo-5-phenyl-2,3-dihydro-1H-benzo[e][1,4]diazepin-3-yl)-3-thiophene-3-yl-urea;
Pyridine-2-carboxylic acid (2-oxo-5-phenyl-2,3-dihydro-1H-benzo[e][1,4]diazepin-3-yl)-amide;
1H-Pyrazole-4-carboxylic acid (2-oxo-5-phenyl-2,3-dihydro-1H-benzo[e][1,4]diazepin-3-yl)-amide;
6-Dimethylamino-N-(2-oxo-5-phenyl-2,3-dihydro-1H-benzo[e][1,4]diazepin-3-yl)-nicotinamide;
2-Ethoxy-naphthalene-1-carboxylic acid (2-oxo-5-phenyl-2,3-dihydro-1H-benzo[e][1,4]diazepin-3-yl)-amide;
9-Oxo-9H-fluorene-1-carboxylic acid (2-oxo-5-phenyl-2,3-dihydro-1H-benzo[e][1,4]diazepin-3-yl)-amide;

2-Oxo-2,3-dihydro-benzoimidazole-1-carboxylic acid (2-oxo-5-phenyl-2,3-dihydro-1H-benzo[e][1,4]diazepin-3-yl)-amide;

(2-Oxo-5-phenyl-2,3-dihydro-1H-benzo[e][1,4]diazepin-3-yl)carbamic acid tert-butyl ester;

(S)-4,5-Dibromo-furan-2-carboxylic acid (2-oxo-5-phenyl-2,3-dihydro-1H-benzo[e][1,4]diazepin-3-yl)-amide;

(S)-Benzofuran-2-carboxylic acid (2-oxo-5-phenyl-2,3-dihydro-1H-benzo[e][1,4]diazepin-3-yl)-amide;

(2-Oxo-5-phenyl-2,3-dihydro-1H-benzo[e][1,4]diazepin-3-yl)-carbamic acid methyl ester;

(2-Oxo-5-phenyl-2,3-dihydro-1H-benzo[e][1,4]diazepin-3-yl)-carbamic acid ethyl ester;

(2-Oxo-5-phenyl-2,3-dihydro-1H-benzo[e][1,4]diazepin-3-yl)-carbamic acid isobutyl ester; and 2-Oxo-N-2-oxo-5-phenyl-2,3-dihydro-1H-benzo[e][1,4]diazepin-3-yl)-2-thiophene-2-yl-acetamide, or a pharmaceutically acceptable salt thereof.

The compounds of formulae (I), (II), (III) and (IV) are known compounds. They are disclosed, for example, in WO 00/195910, WO 00/004900, WO 03/053344, U.S. Pat. No. 4,324,794 and WO 01/00612, and can be prepared by the processes set out in those documents.

WO 00/195910, WO 00/004900, WO 03/053344, U.S. Pat. No. 4,324,794 and WO 01/00612 are incorporated herein by reference. Any of the compounds disclosed as fusion protein inhibitors in those documents can be used in the present invention.

Compounds of formula (V) may be prepared by reacting glyoxylic acid (HCO—CO$_2$H), benzotriazole and an appropriate benzyl carbamate at reflux in toluene, under Dean-Stark conditions giving the key protected amino acid of formula (II')

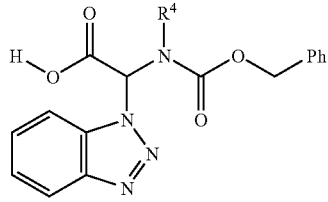

(II')

The thus obtained amino acid of formula (II') can then be reacted with a suitable chlorinating agent, such as oxalyl chloride, followed by reaction with a 2-aminobenzophenone of formula (III')

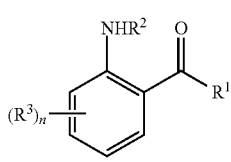

(III')

to give the intermediate amide of formula (IV')

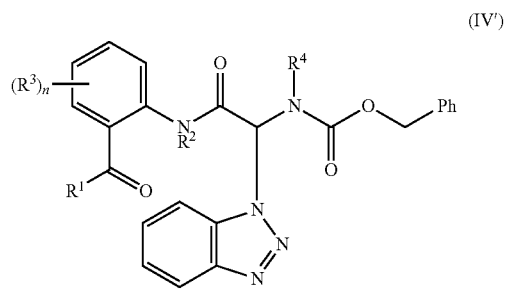

(IV')

which need not be characterized.

The compound of formula (IV') can then be subjected to ammonolysis followed by ring closure in acetic acid containing ammonium acetate to obtain the protected benzodiazepine of formula (V')

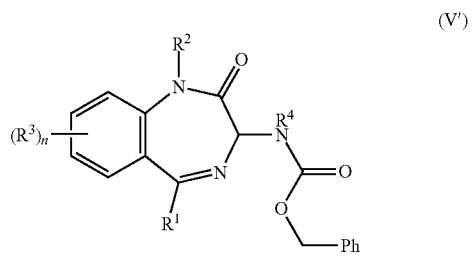

(V')

The compound of formula (V') can then be deprotected using hydrogen bromide in acetic acid to yield the deprotected amine of formula (VI').

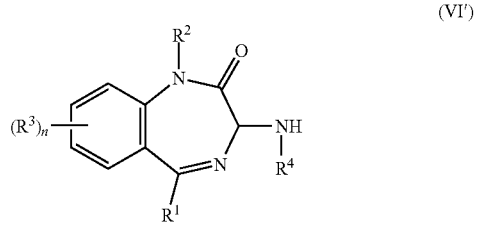

(VI')

Compounds of formula (V), in which $R^5$ is $XR^6$ and X is —CO— can be prepared by reacting a compound of formula (VI'), as defined above, with an acid anhydride in a suitable solvent, preferably pyridine at ambient temperature, or with an acid chloride in a suitable solvent in the presence of a base, preferably in THF at ambient temperature with triethylamine present. Alternatively, the compounds can be produced by reaction of a compound of formula (VI') with an acid in a suitable solvent in the presence of a base and a coupling agent, preferably in THF at ambient temperature with triethylamine and O-benzotriazol-1-yl-N,N,N',N'-tetramethyluronium hexafluorophosphate (HBTU) present.

If the acid chloride used is an amino carbonyl chloride, the compound of formula (V) is a tertiary urea. In the case where $R_6$ is NH—R', such compounds may be prepared by the reaction of a compound of formula (VI') with an isocyanate. This reaction is preferably carried out in THF at ambient temperature. Alternatively, the isocyanate may be prepared in situ from the relevant amine and phosgene, in the presence of a base, usually triethylamine, again in THF.

Compounds of formula (V), in which $R^5$ is —$XR^6$ and X is —$S(O)_2$— may be prepared by the reaction of a compound of formula (VI') with a suitable sulfonyl chloride. Similarly, compounds of formula (V), in which $R^5$ is $XR^6$ and X is —$S(O)$— may be prepared by the reaction of a compound of formula (VI') with a suitable sulfinyl chloride Compounds of formula (V) in which $R^5$ is not $XR^6$ may be prepared by known methods. For example, a compound of formula (VI') can be reacted with a compound of formula $R^5$-L, wherein L is a leaving group such as a chlorine atom, a mesylate group or a triflate group. When $R^5$ is aryl or heteroaryl, L can be —$B(OH)_2$ and the reaction may take place in the presence of copper acetate. Such boronic acid coupling reactions will, of course, be familiar to those of skill in the art. Compounds wherein $R^5$ is aryl or heteroaryl may also be prepared by way of a Buchwald reaction or by reaction of a compound of formula (VI') with an appropriate fluoroaryl or fluoroheteroaryl compound. Compounds wherein $R^5$ is a heteroaryl group may also be prepared by reaction of a compound of formula (VI') with a suitable chloroheteroaryl or bromoheteroaryl compound. Compounds wherein $R^5$ is a carbocyclyl group may also be prepared by known methods, for example a compound wherein $R^5$ is cyclohexyl may be prepared by the reaction of a compound of formula (VI') with cyclohexanone in the presence of a reducing agent.

Compounds of formula (V) in which the $R^5$ group is aryl-($C_{1-6}$ alkyl)-, heteroaryl-($C_{1-6}$ alkyl)-, carbocyclyl-($C_{1-6}$ alkyl)-, heterocyclyl-($C_{1-6}$ alkyl)- can also be prepared by the reaction of a compound of formula (VI') with an aldehyde in the presence of a reducing agent. Preferably, such reactions between compounds of formula (VI') and aldehydes are carried out in a mixture of dichloromethane and acetic acid in the presence of sodium (triacetoxy)borohydride at ambient temperature.

In the preparation of the benzodiazepine skeleton, commercially available aminobenzophenone compounds of formula (III') can be used where possible. Compounds of formula (III') which are not commercially available can be prepared by known methods, for example by reaction of a Weinreb type amide of formula (VII')

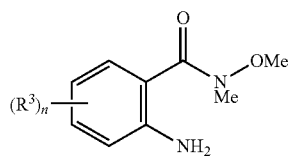

(VII')

with a group $R^1$—Li or a Grignard reagent such as $R^1$—MgBr. Preferably this reaction is carried out in THF at −100° C.

Compounds of formula (VII') are known compounds or can be prepared by analogy with known methods. For example, they can be prepared from the reaction of isatoic anhydrides of formula (VIII')

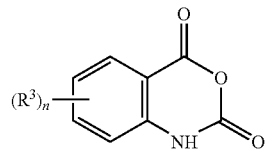

(VIII')

with N,O-dimethyl hydroxylamine under standard reaction conditions.

The starting materials of formula (II'), (III'), (VII'), and (VIII') are known compounds, or may be prepared by analogy with known methods.

Further synthetic manipulation of the thus obtained compounds of formula (V) may be carried out by conventional methods to achieve further compounds of formula (V). The benzodiazepines of formula (V) can be salified by treatment with an appropriate acid or base.

Although the described route to the claimed compounds provides an adequate synthesis for laboratory scale preparations, an alternative route was sought which has potential as a manufacturing route. The same starting material (2-aminobenzophenone) (1) is used in both, however in the alternative route, the benzodiazepine ring system is formed by reaction initially with bromoacetyl bromide (or an equivalent reagent) followed by ring closure with ammonia. These reactions are carried out in a suitable solvent, such as dichloromethane, and at a suitable temperature which may range from −20 to 150° C. In order to protect the NH functionality, at this stage the unsubstituted benzodiazepine is reacted with a base, and an alkylating agent. For instance sodium hydride in DMF followed by addition of 4-methoxy-benzyl chloride gives rise to the intermediate (2) shown below. Further reaction of this material with a base (e.g. potassium tert-butoxide) in a suitable solvent (e.g. THF or DMF) followed by quenching with isoamyl nitrite (or an alternative similar reagent) furnishes the oxime intermediate (3) which may be converted into the racemic primary amine by methods which include the use of hydrogen and a suitable catalyst. This amine then undergoes a Dynamic Kinetic Resolution (DKR) procedure by which the racemic amine in the presence of a suitable optically active acid, and a suitable aldehyde gives rise to precipitation of the salt of the desired (S)-amine (4) in good yield and exceptionally high enantiomeric excess. A suitable acid for this conversion can be e.g. Camphorsulfonic acid, Boc-phenyl alanine or the like, and a suitable aldehyde may be a benzaldehyde such as 3,5-dichloro salicylaldehyde.

The optically amine thus formed may then be transformed into a desired derivative, such as an amide or urea. The amide formations may be carried out using a suitable carboxylic acid and a coupling reagent, or a carbonyl chloride or other suitable reagent, and the ureas prepared using aeither a suitable isocyanate, or alternatively reaction with phosgene followed by a suitable amine.

These derivatives thus formed may then have the protecting group removed. This may be carried out in the presence of a Lewis Acid, such as aluminium chloride, boron trifluoride, titanium tetrachloride, or the like. These reactions are carried out in a suitable inert solvent, such as dichloromethane. Reaction temperatures may range from −20 to 150° C., but are typically carried out at room temperature or below.

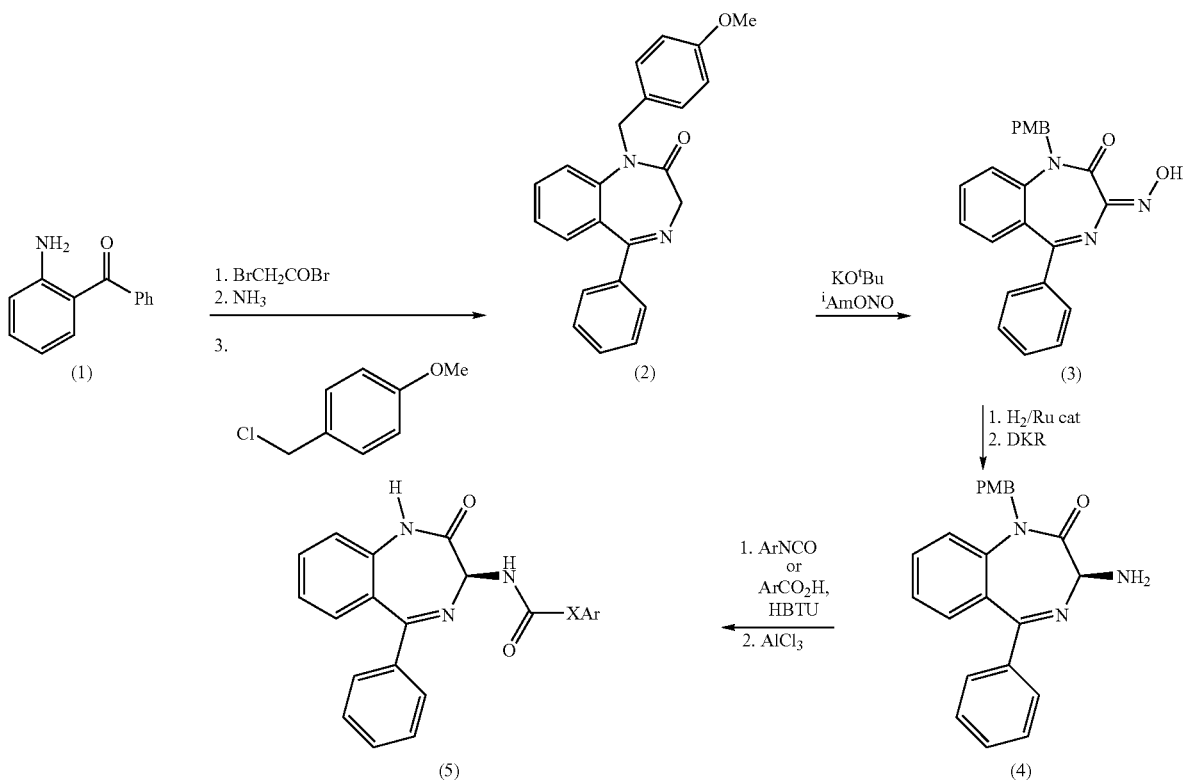

In a particularly preferred embodiment of the invention, component (a) is 1-cyclopropyl-3-[1-(4-hydroxy-butyl)-1H-benzoimidazol-2-ylmethyl]-1,3-dihydro-imidazo[4,5-c]pyridin-2-one, 2-[2-(1,2-dihydro-benzotriazol-1-ylmethyl)-benzoimidazol-1-yl]]ethyl}-diethyl-amine, {2-[2-(3-iodo-2,3-dihydro-indazol-1-ylmethyl)-benzimidazol-1-yl]-ethyl}-dimethyl-amine or a pharmaceutically acceptable salt thereof and component (b) is (S)-1-(2-fluoro-phenyl)-3-(2-oxo-5-phenyl-2,3-dihydro-1H-benzo[e][1,4]diazepin-3-yl)-urea, (S)-2-methoxy-4-nitro-N-(2-oxo-5-phenyl-2,3-dihydro-1H-benzo[e][1,4]diazepin-3-yl)-benzamide, (S)-4-methane-sulfonyl-2-methoxy-N-(2-oxo-5-phenyl-2,3-dihydro-1H-benzo[e][1,4]diazepin-3-yl)-benzamide or a pharmaceutically acceptable salt thereof.

The present invention also provides a pharmaceutical composition according to the invention, for use in the treatment of the human or animal body. Also provided is the use of (a) a said RSV fusion protein inhibitor and (b) a said benzodiazepine derivative, in the manufacture of a medicament for use in treating or preventing an RSV infection.

The present invention also provides a method of treating or preventing an RSV infection in a patient, which method comprises the administration to said patient of (a) a said RSV fusion protein inhibitor and (b) a said benzodiazepine derivative.

Typically, the amount of component (a) in the composition of the invention is from 0.025 wt % to 10 wt %, preferably from 0.25 wt % to 5 wt %, more preferably from 1 wt % to 3.5 wt %, for example about 2.5 wt %, based on the total weight of the composition.

Typically, the amount of component (b) in the composition of the invention is from 0.025 wt % to 10 wt %, preferably from 0.25 wt % to 5 wt %, more preferably from 1 wt % to 3.5 wt %, for example about 2.5 wt %, based on the total weight of the composition.

Typically, the total amount of components (a) and (b) in the composition of the invention is from 0.05 to 20 wt %, preferably from 0.5 to 10 wt %, more preferably from 2 to 7 wt %, for example about 5 wt %, based on the total weight of the composition.

RSV is prevalent among children younger than two years of age, adults suffering from asthma, chronic obstructive pulmonary disorder (COPD) or immunodeficiency and the elderly. It is a particularly serious risk amongst children who suffer from chronic lung disease. Accordingly, the said composition or medicament is typically for use in treating a patient who is a child under two years of age, patients with asthma, COPD or immunodeficiency the elderly or persons in long term care facilities. Typically, said child suffers from chronic lung disease.

Further, anti-RSV prophylaxis is recommended for infants born at 32 weeks of gestation or earlier, until they reach 6 months of age, the elderly, persons with immunedeficiency and those in long term care facilities. Accordingly, the said composition or medicament is typically for use in preventing RSV infection in an infant less than 6 years of age, who was born after 32 weeks of gestation or less, the elderly, persons with immunosufficiency and those in long term care facilities.

As described above, RSV strains upon exposure to fusion inhibitors known in the art rapidly develop resistance. In order to minimize the risk of development of resistance to fusion inhibitors it is desirable to combine them with another inhibitor of RSV replication with a different mode of action. To our knowledge, the benzodiazepine derivatives disclosed above are the first class of compounds with a novel mode of action. Accordingly, the compositions of the invention are characterized by a very low resistance profile, which makes them particularly suitable for therapeutic and prophylactic applications.

The present invention also covers situations where components (a) and (b) are administered separately. Thus, for example, component (a) can be administered up to 24 hours before component (b). Alternatively, component (b) can be administered up to 24 hours before component (a). More usually, when components (a) and (b) are administered separately, they are administered within 12 hours, preferably within 6 hours, of each other.

The present invention therefore also provides a product comprising (a) a said RSV fusion protein inhibitor and (b) a said benzodiazepine derivative for separate, simultaneous or sequential use in the treatment of the human or animal body. Typically, said product is for separate, simultaneous or sequential use in treating or preventing an RSV infection.

Also provided is the use of a said RSV fusion protein inhibitor in the manufacture of a medicament for use in treating or preventing an RSV infection by co-administration with a said benzodiazepine derivative. The present invention also provides the use of a said benzodiazepine derivative in the manufacture of a medicament for use in treating or preventing an RSV infection, by co-administration with a said RSV fusion protein inhibitor.

When components (a) and (b) are administered separately, they are typically formulated as described above. The amount of active ingredient in each separate formulation will, of course, correspond to the amount of component (a) or (b) given above for the combined formulation. Thus, when components (a) and (b) are administered separately, a first formulation is typically provided which contains from 0.025 wt % to 10 wt %, preferably from 0.25 wt % to 5 wt %, more preferably from 1 wt % to 3.5 wt %, for example about 2.5 wt %, of a said RSV fusion protein inhibitor, based on the total weight of the formulation. Similarly, a second formulation is typically provided which contains from 0.025 wt % to 10 wt %, preferably from 0.25 wt % to 5 wt %, more preferably from 1 wt % to 3.5 wt %, for example around 2.5 wt %, of a said benzodiazepine derivative, based on the total weight of the formulation. The two formulations can be administered separately in any order.

Preferably, the compositions and medicaments of the invention have an activity greater than the combined individual activities of compounds (a) and (b). Thus, components (a) and (b) typically interact synergistically. Preferably, therefore, in the formulations and the medicaments of the invention, component (a) and component (b) are each present in an amount producing a synergistic therapeutic effect in treating or preventing an RSV infection.

The anti-RSV compositions of the invention may be administered in a variety of dosage forms. Thus, they can be administered orally, for example as tablets, troches, lozenges, aqueous or oily suspensions, dispersible powders or granules. The compounds of the invention may also be administered parenterally, whether subcutaneously, intravenously, intramuscularly, intrasternally, transdermally or by infusion techniques. The compounds may also be administered as suppositories.

In a preferred embodiment, administration is by intravenous, intranasal or intrabronchial means. In particular, formulations for treating or preventing RSV can advantageously be administered intranasally. The present invention therefore also provides an inhaler or nebuliser containing a medicament which comprises (i) a composition of the invention comprising component (a) and component (b), as defined above, and (ii) a pharmaceutically acceptable carrier or diluent.

The anti-RSV compositions of the invention are typically formulated for administration with a pharmaceutically acceptable carrier or diluent. For example, solid oral forms may contain, together with the active compound(s), diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non toxic and pharmacologically inactive substances used in pharmaceutical formulations. Such pharmaceutical preparations may be manufactured in known manner, for example, by means of mixing, granulating, tableting, sugar coating, or film coating processes.

Liquid dispersions for oral administration may be syrups, emulsions and suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for injection or infusion may contain as carrier, for example, sterile water or preferably they may be in the form of sterile, aqueous, isotonic saline solutions.

Preferably, the anti-RSV compositions of the invention are solubilised in a carrier containing (a) a pharmaceutically acceptable oil selected from esterification or polyether products of glycerides with vegetable oil fatty acids of chain length $C_8$-$C_{10}$ and (b) a pharmaceutically acceptable surfactant selected from oleate and laurate esters of a polyalcohol copolymerized with ethylene oxide. Particularly preferred carriers contain Labrafil as the oil and Tween 20 or Tween 80 as the surfactant.

The anti-RSV compositions of the invention also be suspended in PEG 400 for oral administration.

A therapeutically effective amount of an anti-RSV composition of the invention is administered to a patient. A typical dose is from about 0.001 to 50 mg, typically 0.5 to 30 mg, preferably 1 to 20 mg active ingredient per kg of body weight, according to the activity of the specific composition, the age, weight and conditions of the subject to be treated, the type and severity of the disease and the frequency and route of administration. Preferably, daily dosage levels are from 5 mg to 2 g active ingredient.

The following Examples illustrate the invention. They do not however, limit the invention in any way. In this regard, it is important to understand that the particular assays used in the Examples section are designed only to provide an indication of antiviral activity. There are many assays available to determine the activity of given compounds against RSV, and a negative result in any one particular assay is therefore not determinative.

EXAMPLES

Example 1

3-[1-(3-Methyl-butyl)-1H-benzoimidazol-2-ylmethyl]-2-oxo-2,3-dihydro-benzoimidazol-1-sulfonic acid dimethylamide, 1-Methanesulfonyl-3-[1-(3-methyl-butyl)-1H-benzoimidazol-2-ylmethyl]-1,3-dihydro-benzoimidazol-2-one, 3-[1-(3-Methyl-butyl)-1H-benzoimidazol-2-ylmethyl]-2-oxo-2,3-dihydro-benzoimidazol-1-carboxylic acid benzylamide, 5-{3-[1-(3-Methanesulfonyl-propyl)-1H-benzoimidazol-2-ylmethyl]-2-oxo-2,3-dihydro-benzoimidazol-1-yl}-pentanenitrile, 7-[2-(3-Isopropenyl-2-oxo-2,3-dihydrobenzoimidazol-1-ylmethyl)-benzoimidazol-1-yl]-heptanenitril, 1-Ethyl-3-[1-(4-hydroxy-butyl)-1H-benzoimidazol-2-ylmethyl]-1,3-dihydro-benzoimidazol-2-one, 1-Ethyl-3-[1-(2-hydroxy-2-phenyl-ethyl)-1H-benzoimidazol-2-ylmethyl]-1,3-dihydro-benzoimidazol-2-one, 1-Isopropenyl-3-[1-(3-oxo-butyl)-1H-benzoimidazol-2-ylmethyl]-1,3-dihydro-benzoimidazol-2-one, 1-(4-Hydroxy-benzyl)-3-[1-(3-methyl-butyl)-1H-benzoimidazol-2-ylmethyl]-1,3-dihydro-benzoimidazol-2-one, 1-Isopropenyl-3-[1-(3-methyl-butyl)-1H-benzoimidazol-2-ylmethyl]-1,3dihydro-benzoimidazol-2-one, 1-Cyclopropyl-3-[1-(4-hydroxy-butyl)-1H-benzoimidazol-2-ylmethyl]-1,3-dihydro-imidazo[4,5-c]pyridin-2-one and 1-Isopropenyl-3-(1-propyl-1H-benzoimidazol-2-ylmethyl)-1,3-dihydro-imidazo[4,5-c]pyridine-2-one are prepared as described in WO00195910

Example 2

{2-[2-(1,2-Dihydro-benzotriazol-1-ylmethyl)-benzoimidazol-1-yl]ethyl}-diethyl-amine is prepared as described in WO00004900.

Example 3

{2-[2-(3-Iodo-2,3-dihydro-indazol-1-ylmethyl)-benzimidazol-1-yl]-ethyl}-dimethyl-amine is prepared as described in WO03053344.

Example 4

Bis(5-amidino-2-benzimidazolyl)-methane is prepared as described in U.S. Pat. No. 4,324,794.

Example 5

2-{2-[1-[1-(2-Amino-ethyl)-piperidin-4-ylamino]-4-methyl-benzoimidazol-1-ylmethyl}-6-methyl-pyridin-3-ol is prepared as described in WO01100612.

Example 6

Compounds of general formula (V) are prepared as described in PCT/GB03/04050. In particular, (S)-1-(2-fluoro-phenyl)-3-(2-oxo-5-phenyl-2,3-dihydro-1H-benzo[e][1,4]benzodiazepin-3-yl-urea and (S)-4-methanesulfonyl-2-methoxy-N-(2-oxo-5-phenyl-2,3-dihydro-1H-benzore][1,4]diazepin-3-yl)-benzamide were prepared according to the protocols described in Examples 75b and 73b of PCT/GB03/04050.

Example 7

Determination of RSV Fusion Inhibitor Activity

RSV enters the host cell via attachment to and fusion with the host cell membrane. The effect of an inhibitor on the specific virus-cell fusion event can be qualitatively determined by using a fluorescence de-quenching system.

The design of this assay takes advantage of the fact that RSV binds to cells at 4° C. and at 37° C. but that fusion may only occur at concentrations above 18° C.

RSV labelled with octadecyl rhodamine dye (R18) is pre-incubated with Hep-2 cells seeded in a 6-well plate for 1 hour at 4° C. to allow binding to occur. Unattached virus is removed by washing the cell monolayer. The inhibitor is then added to the virus-cell complexes prior to transferring the plates to 37° C. for 1 hour in order to induce fusion. Virus-cell fusion can be observed directly under a fluorescence microscope. Fluorescence emission is quenched when 2 identical fluorophores are in close proximity. Upon fusion of the labelled virus with the cell membrane, the distance between fluorophores is increased due to dye spread and there is a decrease in quenching. This is observed as an increase in fluorescence intensity of R18. It therefore follows that inhibition of fusion would lead to a decrease in fluorescence of R18 compared to untreated control. Where the fluorescent yield of R18 in the presence of inhibitor is comparable to the untreated control this would suggest the inhibitor were not exerting its effects on the fusion protein.

Example 8

Determination of RSV Reglication Inhibitor Activity

The inner 60 wells of 96 well tissue culture plates are seeded with Hep-2 cells at $4 \times 10^4$ cells/well for compound activity and toxicity studies in 100 µl of medium and incubated at 37° C. overnight or until nearing confluency.

Cells are infected with 25 µl RSV, e.g. the RSS strain, previously titrated to give 80% cell kill. To each well 25 µM of test compound are added. The final DMSO concentration is 0.5%. Some 200 µl of sterile distilled water is added to the outer wells of the plate and incubated at 37° C. for 6 days. Some 0.25 µl/ml PMS are added to stock XTT solution, final conc. 25 µM PMS. Then 25 µl warmed XTT/PMS solution is added to each well and incubated for 1 hour at 37° C.

Maximum $OD_{450nm}$ reading (uninfected, untreated control cells) corresponds to 100% inhibition. Minimum $OD_{450nm}$ readings (infected control cells) corresponds to 0% inhibition. Log10 concentration is plotted against $OD_{450nm}$ and $IC_{50}$ values are calculated from either reading 50% value from graph or using regression analysis.

Example 9

Synergistic Action Between RSV Fusion Inhibitor and Anti-RSV Benzodiazepines

ELISA experiments were carried out on the combined effect of potent benzodiazepine RSV replication inhibitor (S)-1-(2-Fluoro-phenyl)-3-(2-oxo-5-phenyl-2,3-dihydro-1H-benzo[e][1,4]diazepin-3-yl)-urea (compound A) with one RSV fusion inhibitor selected from 1-cyclopropyl-3-[1-(4-hydroxy-butyl)-1H-benzoimidazol-2-ylmethyl]-1,3-dihydro-imidazo[4,5-c]pyridin-2-one (compound B) or 1-isopropenyl-3-(1-propyl-1H-benzoimidazol-2-ylmethyl)-1,3-dihydro-imidazo[4,5-c]pyridine-2-one (compound B)

ELISA Protocol

Mouse monoclonal antibodies to the phosphoprotein (P), nucleocapsid (N) & fusion (F) proteins of RSV and a rabbit anti-mouse-horseradwash peroxidase (HRP) conjugated secondary antibody were used to demonstrate a reduction in RSV antigen via conversion of the o-phenylene diamine dihydrochloride (OPD) substrate to a coloured product. This was quantified by optical density (OD) measurement.

Method

This assay was set up using all 96 wells of flat-bottomed 96-well plates. The outer wells were not subjected to any greater amount of evaporation than the inner wells during the 3 day assay period. (ie. No "edge effect" seen).

Plates were set up one day before addition of virus and compounds. The assay then ran for 3 days with ELISA development taking place on the $4^{th}$ day.

Day 0

Set Up of Assay Plates

All 96 wells of a microtitre plate were seeded at a density of $5 \times 10^3$ Hep-2 cells/well in 100 µl/well of Growth Medium (GM) consisting of Dulbecco's MEM (DMEM) with Glutamax-1, Sodium Pyruvate, 1000 mg/l glucose and pyridoxine (Invitrogen, catalogue number 21885-025) and supplemented with 10% FBS. (See Plate 1).

In tissue culture, the cells adhere to the tissue culture flask and were grown at 37° C., 5% $CO_2$ until 90% confluent.

Monolayers were washed with 20 ml sterile PBS to remove serum and treated with 1 ml trypsin to detach cells from the flask.

Cells were suspended in a small known volume of growth media and counted using a haemocytometer. The cell suspension was made up to the desired concentration in growth medium and added to wells by multichannel pipette. Brief, gentle shaking encouraged the cells to disperse more evenly across the well.

| Plate 1 | | | | | | | | | | | |
|---|---|---|---|---|---|---|---|---|---|---|---|
| cells | cells | cells | cells | cells | cells | cells | cells | cells | cells | cells | cells |
| cells | cells | cells | cells | cells | cells | cells | cells | cells | cells | cells | cells |
| cells | cells | cells | cells | cells | cells | cells | cells | cells | cells | cells | cells |
| cells | cells | cells | cells | cells | cells | cells | cells | cells | cells | cells | cells |
| cells | cells | cells | cells | cells | cells | cells | cells | cells | cells | cells | cells |
| cells | cells | cells | cells | cells | cells | cells | cells | cells | cells | cells | cells |
| cells | cells | cells | cells | cells | cells | cells | cells | cells | cells | cells | cells |
| cells | cells | cells | cells | cells | cells | cells | cells | cells | cells | cells | cells |

Plates were kept undisturbed at 37° C. in a 5% $CO_2$ atmosphere for 24 hrs during which time the cells settle to form an even cell monolayer.

Day 1

Addition of Virus

A frozen vial of RSV (RSS strain provided by Virogen Ltd) stock solution was removed from the −80 freezer or liquid nitrogen store and diluted to a known Multiplicity of Infection (m.o.i) in Growth Medium.

The m.o.i. was calculated by prior titration of the virus stock (by the ELISA assay method) as the virus input required to achieve a window of at least 0.8 OD units between infected and uninfected control wells.

$$\text{Multiplicity of Infection} = \frac{\text{plaque forming units per well } (pfu/\text{well})}{\text{number of cells per well}}$$

25 µl (50 µl in Example 9c) of diluted virus was added to infected wells by multichannel pipette; 25 µl (50 µl in Example 9c) of Growth Medium was added to uninfected, cell control wells by multichannel pipette.

Sides of plates were marked with stripes to identify plates in the event of lids becoming separated.

Plates were incubated at 37° C. for 1 hr to allow virus adsorption.

Compound Dilutions

Compound "A" was titrated horizontally across the plate and Compound "B" was titrated vertically down the plate, creating a chequerboard. The 2 compounds were titrated at either ½-log or doubling dilutions either across (horizontally) or down the plate (vertically) in the presence of virus. Each compound dilution was set up in duplicates or triplicates. For triplicates 3 identical plates were set up. Duplicates were set up as dublicate wells on the same plate. The dilution range covered concentrations from just above the compound IC50 to below the compound IC50 and included a 0 µM control for each compound.

Compounds were made up in a separate microtitre plate at 8× strength in GM containing 2% DMSO (a final DMSO concentration in the assay of 0.5%). 12.5 µM (25 µl in Example 9c) of the Compound "A" dilution series and 12.5 µl (25 µl in Example 9c) of the Compound "B" dilution series were then transferred to the appropriate wells of the assay plate by multichannel pipette, according to the marked out chequerboard.

12.5 µl (25 µl in Example 9c) of GM (containing 2% DMSO) was added to wells receiving 0 µM Compound "A" or 0 µM Compound "B". 25 µl (50 µl in Example 9c) GM (containing 2% DMSO) was added to wells containing neither compound.

Virus infected, untreated wells served as the virus control (VC); Uninfected, untreated wells serve as the cell control (CC). The difference in absorbance between CC and VC wells constitutes the assay window.

Plates were incubated at 37° C., 5% $CO_2$ for 3 days.

ELISA Stage

Day 4

Media was tapped out from wells directly into Virkon (1% solution in water) and plates were washed by immersing in a plastic box containing PBS.

50 µl/well of 75%/25% vol/vol acetone/methanol fixative was added by multichannel pipette and left for 3mins.

Acetone/methanol was discarded from wells into Virkon and wells were washed with PBS as above.

Some 200 µl of blocking solution (2% Marvel in PBS containing 0.05% Tween) was added per well by multichannel pipette. Plates were incubated at 37° C. in a shaking incubator for 60 mins.

Block solution was discarded down the sink and diluted primary antibody was added directly to wells (ie. no washing required).

RSV mouse monoclonal antibody NCL-RSV3 (Novocastra ) was diluted 1/400 in PBS/2% Marvel/0.05% Tween and 50 µl was added per well. Plates were incubated at 37° C. in a shaking incubator for 90 mins.

Antibody was discarded down the sink and plates were washed 4 times by immersion in PBS/0.05% Tween.

DAKo rabbit anti-mouse HRP conjugate (DAKO catalogue number P0260) was diluted 1/1000 in PBS/2% Marvel/ 0.05% Tween and 50 µl was added per well. Plates were incubated at 37° C. in a shaking incubator for 60mins.

Antibody was discarded down the sink and plates were washed 6 times by immersion in PBS/0.05% Tween.

Substrate (SigmaFast OPD) was prepared in advance by dissolving 1 urea tablet in 20 mL water. 1 OPD tablet was added to the urea solution just prior to use (NB. OPD was light sensitive) and vortexed to mix. 50 µl of substrate was added per well.

The reaction was stopped by addition of 25 μl/well of 20% sulphuric acid, once sufficient colour had developed but while cell control background was still low (~5 minutes).

Plates were read on a SpectraMax (Molecular Devices) spectrophotometer at wavelength 490 nm and utilize the SOFTmax Pro software package.

The wells were emptied, washed in tap water and the monolayers stained with 50 μl/well of 2% crystal violet in 20% methanol/water for at least 1 hour. The wells were then washed and air-dried and the monolayers examined under the microscope for indications of cell toxicity.

Results

SOFTmax data files were exported to Excel. Data handling used Excel templates written in-house for plotting dose response curves graphically and calculating IC50 values from the curves obtained.

All replicate wells were meaned. The assay window was calculated by subtracting the meaned cell control (CC) from the meaned virus control (VC). For each compound, the meaned CC was subtracted from the meaned values for each concentration point. The % of control was then calculated for each concentration point as a percentage of the window. % of control was plotted against compound concentration. A straight line was fitted to the curve and the slope and intercept functions were used to calculate the IC50.

The IC50 for Compound "A" was calculated for each background concentration of Compound "B". Similarly, the IC50 for Compound "B" was calculated for each background concentration of Compound "A".

Example 9a (S)-1-(2-Fluoro-phenyl)-3-(2-oxo-5-phenyl-2,3dihydro-1H-benzo[e][1,4diazepin-3-yl)-urea (Compound B) in Combination with the 1-isopropenyl-3-(1-propyl-1H-benzoimidazol-2-ylmethyl)-1.3-dihydro-imidazo[4.5-c]pyridine-2-one (Compound A)

Compound B has an ELISA IC50 of 2 μM against the RSV RSS strain.

Compound A has an ELISA IC50 of 0.5 μM against the RSV RSS strain.

In combination, at concentrations of Compound A below its IC50 (1, 0.3, 0.1 μM) the IC50 of Compound B is reduced from 0.5 μM to at least 0.16 μM (3.2-fold decrease). At concentrations of Compound B below its IC50 (0.3, 0.1 μM) the IC50 of Compound A is reduced from 2 μM to at least 0.65 μM (3-fold decrease).

Example 9b (S)-1-(2-Fluoro-phenyl)-3-(2-oxo-5-phenyl-2,3-dihydro-1H-benzo[e][1,4]diazepin-3-yl)-urea (Compound B) in Combination with 1-cyclopropyl-3-[1-(4-hydroxy-butyl)-1H-benzoimidazol-2-ylmethyl]-1,3-dihydro-imidazo[4,5-c]pyridin-2-one (Compound A)

Compound B has an ELISA IC50 of 1.4 μM against the RSV RSS strain.

Compound A has an ELISA IC50 of 0.015 μM against the RSV RSS strain.

In combination, at concentrations of Compound B below its IC50 (1, 0.3, 0.1, 0.03 μM), the IC50 of Compound A is reduced from 0.015 μM to at least 0.0007 μM (21.4-fold decrease). At concentrations of Compound A below its IC50 (0.01, 0.003, 0.001, 0.0003 μM) the IC50 of compound B is reduced from 1.4 μM to at least 0.26 μM (5.4-fold decrease).

Example 9c (S)-4-Methanesulfonyl-2-methoxy-N-(2-oxo-5-phenyl-2,3-dihydro-1H-benzo[e][4]diazepin-3-yl)-benzamide (Compound A) in combination with 1-cyclopropyl-3-[1-(4-hydroxy-butyl)-1H-benzoimidazol-2-ylmethyl]-1,3-dihydro-imidazo[4.5-c]pyridin-2-one (Compound B)

Compound A has an ELISA IC50 of 1 μM against the RSV RSS strain.

Compound B has an ELISA IC50 of 0.08 μM against the RSV RSS strain.

In combination, at concentrations of Compound A below its IC50 the IC50 of Compound B is reduced from 0.08 μM to at least 0.03 μM (2.66fold decrease). At concentrations of Compound B below its IC50 the IC50 of Compound A is reduced from 1 μM to at least 0.3 μM (3.33-fold decrease).

The formula below can be used to identify a synergistic interaction.

FIC=Fractional Inhibitory concentration.

Compares the activity of a compound in combination (Compound A+Compound B) with the activity of the compound alone (Compound A or Compound B).

$$FIC = \frac{\text{Lowest } IC50 \text{ } Cpd \text{ } A^{COMBINATION}}{IC50 \text{ } Cpd \text{ } A^{ALONE}} + \frac{\text{Lowest } IC50 \text{ } Cpd \text{ } B^{COMBINATION}}{IC50 \text{ } Cpd \text{ } B^{ALONE}}$$

| where FIC value | <0.5 | SYNERGY |
| --- | --- | --- |
| | 0.5-1.0 | ADDITION |
| | 1.0-2.0 | INDIFFERENCE |
| | >2.0 | ANTAGONISM |

FIC for (S)-1-(2-Fluoro-phenyl)-3-(2-oxo-5-phenyl-2,3-dihydro-1H-benzo[e][1,4]diazepin-3-yl)-urea in combination with the 1-isopropenyl-3-(1-propyl-1H-benzoimidazol-2-ylmethyl)-1,3-dihydro-imidazo[4,5-c]pyridine-2-one: <0.25

FIC for (S)-1-(2-Fluoro-phenyl)-3-(2-oxo-5-phenyl-2,3-dihydro-1H-benzo[e][1,4]diazepin-3-yl)-urea (Compound B) in combination with 1-cyclopropyl-3-[1-(4-hydroxy-butyl)-1H-benzoimidazol-2-ylmethyl]-1,3-dihydro-imidazo[4,5-c]pyridin-2-one: <0.04

FIC for (S)-4-Methanesulfonyl-2-methoxy-N-(2-oxo-5-phenyl-2,3-dihydro-1H-benzo[e][1,4]diazepin-3-yl)-benzamide in combination with 1-cyclopropyl-3-[1-(4-hydroxy-butyl)-1H-benzoimidazol-2-ylmethyl]-1,3-dihydro-imidazo[4,5-c]pyridin-2-one: 0.0675

The invention claimed is:

1. A pharmaceutical composition which comprises a pharmaceutically acceptable carrier or diluent and:
   (a) an inhibitor of the RSV fusion protein; and
   (b) a benzodiazepine derivative capable of inhibiting RSV replication wherein component (a) is a compound of formula (I):

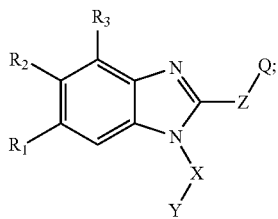

or a pharmaceutically acceptable salt thereof, wherein:
X is a direct link;
Y is;
Z is $CR_6R'$, where $R_6$ is H, or straight, branched or cyclic $C_{1-6}$ alkyl and R' is straight, branched or cyclic $C_{1-6}$ alkyl;
$R_1$ is H, $CONR_4R_5$, $CO_2R_4$ or $C_{1-6}$ alkyl, said $C_{1-6}$ alkyl can be optionally substituted with $OR_4$ or $NR_8R_9$;
$R_4$ and $R_5$ are H or $C_{1-6}$ alkyl;
$R_8$ and $R_9$ are each independently H, $C_{1-6}$ alkyl, $SO_2R_5$, $CO_2R_4$ or $COR_4$;
$R_2$ is selected from the group consisting of H, $NH_2$, $CONR_6R'$, heteroaryl, $C_{2-6}$ alkenyl, $CO_2R_4$, N=$CPh_2$, C(=NH)$NH_2$ and $C_{1-6}$ alkyl; said alkyl optionally substituted with a member selected from the group consisting of halogen, CN, $NR_{10}R_{11}$, $OSO_2R_4$ and $OR_4$;
$R_{10}$ and $R_{11}$ are each independently selected from the group consisting of H, $C_{1-6}$ alkyl, $C_{3-6}$ cycloalkyl, $CO_2R_4$, $COR_4$ and $SO_2R_4$;
$R_3$ is selected from the group consisting of (1) $CO_2R_9$; (2) $C_{1-6}$ alkyl optionally substituted with CN, $OR_4$ or $NR_6R'$; (3) H; and (4) $C_{2-6}$ alkenyl substituted with CN;
Q is

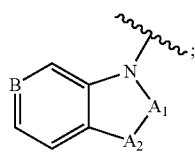

B is —CH— or —N—;
$A_1$ is —C(O)— or —NH—;
$A_2$ is —$CH_2$—, —CHR'— or —NR"—, wherein R' is a halogen atom and R" represents a hydrogen atom or a $C_1$—$C_4$ alkyl, $C_2$—$C_4$ alkenyl, $C_3$—$C_6$ cycloalkyl, $SO_2$-—($C_1$-$C_6$ alkyl), —$SO_2$—N($C_1$-$C_6$ alkyl)$_2$ or —(CONH)a($C_1$-$C_4$ alkyl)-phenyl group, wherein a is 0 or 1, which group is unsubstituted or is substituted with a hydroxyl or cyano substituent; and
wherein component (b) is a compound of formula (V)

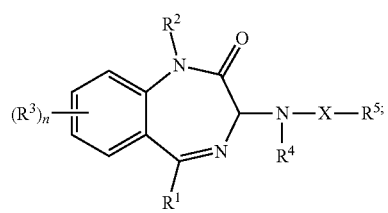

or a pharmaceutically acceptable salt thereof, wherein:

$R^1$ represents $C_{1-6}$ alkyl, aryl or heteroaryl;
$R^2$ represents hydrogen or $C_{1-6}$ alkyl;
each $R^3$ is the same or different and represents halogen, hydroxy, $C_{1-6}$ alkyl, $C_{1-6}$ alkoxy, $C_{1-6}$ alkylthio, $C_{1-6}$ haloalkyl, $C_{1-6}$ haloalkoxy, amino, mono($C_{1-6}$ alkyl)amino, di($C_{1-6}$ alkyl)amino, nitro, cyano, —$CO_2R'$, —CONR'R", —NH—CO—R', —S(O)R', —S(O)$_2$R', —NH—S(O)$_2$R', —S(O)NR'R" or —S(O)$_2$NR'R", wherein each R' and R" is the same or different and represents hydrogen or $C_{1-6}$ alkyl;
n is from 0 to 3;
$R^4$ represents hydrogen or $C_{1-6}$ alkyl;
$R^5$ represents $C_{1-6}$ alkyl, aryl, heteroaryl, carbocyclyl, heterocyclyl, aryl-($C_{1-6}$ alkyl)-, heteroaryl-($C_{1-6}$ alkyl)-, carbocyclyl-($C_{1-6}$ alkyl)-, heterocyclyl-($C_{1-6}$ alkyl)-, aryl-($C_{1-6}$ hydroxyalkyl)-, heteroaryl-($C_{1-6}$ hydroxyalkyl)-, carbocyclyl-($C_{1-6}$ hydroxyalkyl)-, heterocyclyl-($C_{1-6}$ hydroxyalkyl)-, aryl-C(O)—C(O)—, heteroaryl-C(O)—C(O)—, carbocyclyl-C(O)—C(O)—, heterocyclyl-C(O)—C(O)— or —$XR^6$;
X represents —CO—, —S(O)— or —S(O)$_2$—; and
$R^6$ represents $C_{1-6}$ alkyl, hydroxy, $C_{1-6}$ alkoxy, $C_{1-6}$ alkylthio, aryl, heteroaryl, carbocyclyl, heterocyclyl, aryl-($C_{1-6}$ alkyl)-, heteroaryl-($C_{1-6}$ alkyl)-, carbocyclyl-($C_{1-6}$ alkyl)-, heterocyclyl-($C_{1-6}$ alkyl)-, aryl-($C_{1-6}$ alkyl)—O—, heteroaryl-($C_{1-6}$ alkyl)-O—, carbocyclyl-($C_{1-6}$ alkyl)-O—, heterocyclyl-($C_{1-6}$ alkyl)-O— or —NR'R" wherein each R' and R" is the same or different and represents hydrogen, $C_{1-6}$ alkyl, carbocyclyl, heterocyclyl, aryl, heteroaryl, aryl-($C_{1-6}$ alkyl)-, heteroaryl-($C_{1-6}$ alkyl)-, carbocyclyl-($C_{1-6}$ alkyl)-, heterocyclyl-($C_{1-6}$ alkyl)-aryl-($C_{1-4}$ hydroxyalkyl)-, heteroaryl-($C_{1-4}$ hydroxyalkyl)-, carbocyclyl-($C_{1-4}$ hydroxyalkyl)-, or heterocycyl-($C_{1-4}$ hydroxyalkyl)-; wherein the carbocyclyl, heterocyclyl, aryl, or heteroaryl groups are optionally substituted.

2. A composition according to claim 1, wherein, in the compound of formula (V):
each $R^3$ is the same or different and represents halogen, hydroxy, $C_{1-6}$ alkyl, $C_{1-6}$ alkoxy, $C_{1-6}$ alkylthio, $C_{1-6}$ haloalkyl, $C_{1-6}$ haloalkoxy, amino, mono($C_{1-6}$ alkyl)amino, di($C_{1-6}$ alkyl)amino, nitro, cyano, —$CO_2R'$, —CONR'R", —NH—CO—R', —S(O)R', —S(O)$_2$R', —NH—S(O)$_2$R' or —S(O)NR'R", wherein each R' and R" is the same or different and represents hydrogen or $C_{1-6}$ alkyl;
"$R^5$ represents $C_{1-6}$ alkyl, aryl, heteroaryl, carbocyclyl, heterocyclyl, aryl-($C_{1-6}$ alkyl)-, heteroaryl-($C_{1-6}$ alkyl)-, carbocyclyl-($C_{1-6}$ alkyl)-, heterocyclyl-($C_{1-6}$ alkyl)- or —$XR^6$;
X represents —CO—, —S(O)— or —S(O)$_2$-; and
$R^6$ represents $C_{1-6}$ alkyl, hydroxy, $C_{1-6}$ alkoxy, $C_{1-6}$ alkylthio, aryl, heteroaryl, carbocyclyl, heterocyclyl, aryl-($C_{1-6}$ alkyl)-, heteroaryl-($C_{1-6}$ alkyl)-, carbocyclyl-($C_{1-6}$ alkyl)-, heterocyclyl-($C_{1-6}$ alkyl)- or —NR'R" wherein each R' and R" is the same or different and represents hydrogen, $C_{1-6}$ alkyl, carbocyclyl, heterocyclyl, aryl, heteroaryl, aryl-($C_{1-6}$ alkyl)- or heteroaryl-($C_{1-6}$ alkyl)-.

3. A composition according to claim 1, wherein, in the compound of formula (V), $R^1$ is $C_{1-2}$ alkyl or aryl.

4. A composition according to claim 1, wherein, in the compound of formula (V), $R^2$ is hydrogen.

5. A composition according to claim 1, wherein, in the compound of formula (V), $R^3$ is halogen, hydroxy, $C_{1-4}$ alkyl, $C_{1-4}$ alkoxy, $C_{1-4}$ alkylthio, $C_{1-4}$ haloalkyl, $C_{1-4}$ haloalkoxy, amino, mono($C_{1-4}$ alkyl)amino or di($C_{1-4}$ alkyl)amino.

6. A composition according to claim 5, wherein, in the compound of formula (V), $R^3$ is fluorine, chlorine, bromine, $C_{1-2}$ alkyl, $C_{1-2}$ alkoxy, $C_{1-2}$ alkylthio, $C_{1-2}$ haloalkyl, $C_{1-2}$ haloalkoxy, amino, mono($C_{1-2}$ alkyl)amino or di ($C_{1-2}$ alkyl) amino.

7. A composition according to claim 5, wherein, in the compound of formula (V), $R^4$ is hydrogen or $C_{1-2}$ alkyl.

8. A composition according to claim 1, wherein, in the compound of formula (V), $R^5$ is $C_{1-6}$ alkyl, aryl, heteroaryl, carbocyclyl, heterocyclyl, aryl-($C_{1-4}$ alkyl)-, heteroaryl-($C_{1-4}$ alkyl)-, carbocyclyl-($C_{1-4}$ alkyl)-, heterocyclyl- $C_{1-4}$ alkyl)-, aryl-C(O)—C(O)—, heteroaryl-C(O)—C(O)— or —$XR^6$.

9. A composition according to claim 8, wherein, in the compound of formula (V), $R^5$ is $C_{1-4}$ alkyl, aryl, heteroaryl, carbocyclyl, heterocyclyl, phenyl-($C_{1-2}$ alkyl)-, heteroaryl-($C_{1-2}$ alkyl)-, phenyl-C(O)—C(O)—, heteroaryl-C(O)—C(O)— or —$XR^6$.

10. A composition according to claim 9, wherein, in the compound of formula (V), $R^5$ is $C_{1-4}$ alkyl, phenyl, thienyl, furanyl, isoxazolyl, pyridyl, cyclopentyl, cyclohexyl, benzothienyl, dihydrobenzofuranyl, phenyl-$CH_2$-, furanyl-$CH_2$-, phenyl-C(O)—C(O)—, thienyl-C(O)—C(O)- or —$XR^6$.

11. A composition according to claim 1, wherein, in the compound of formula (V), X is —CO— or —$S(O)_2$-.

12. A composition according to claim 1, wherein, in the compound of formula (V), when $R^6$ is a group NR'R" wherein each R' and R" is the same or different and represents hydrogen, $C_{1-4}$ alkyl, aryl, carbocyclyl, heterocyclyl, aryl-($C_{1-4}$ alkyl)- or heteroaryl-($C_{1-4}$ alkyl)-.

13. A composition according to claim 12, wherein, in the compound of formula (V), when $R^6$ is a group —NR'R" each R' and R" is the same or different and represents hydrogen, $C_{1-4}$ alkyl, phenyl, thienyl, cyclohexyl, cyclopentyl or phenyl-$CH_2$-.

14. A composition according to claim 13, wherein, in the compound of formula (V), when $R^6$ is a group —NR'R" and one of R' and R" is hydrogen.

15. A composition according to claim 1, wherein, in the compound of formula (V), $R^6$ is $C_{1-6}$ alkyl, hydroxy, $C_{1-6}$ alkoxy, $C_{1-6}$ alkylthio, aryl, heteroaryl, carbocyclyl, heterocyclyl, aryl-($C_{1-4}$ alkyl)-, heteroaryl-($C_{1-4}$ alkyl)-, carbocyclyl-($C_{1-4}$alkyl)-, heterocyclyl-($C_{1-4}$ alkyl)-, aryl-($C_{1-4}$ hydroxyalkyl)-, heteroaryl-($C_{1-4}$ hydroxyalkyl)-, carbocyclyl-($C_{1-4}$ hydroxyalkyl)-, heterocyclyl-($C_{1-4}$ hydroxyalkyl)-, aryl-($C_{1-4}$ alkyl)-O—, heteroaryl-($C_{1-4}$ alkyl)-O—, carbocyclyl-($C_{1-4}$ alkyl)-O—, heterocyclyl-($C_{1-4}$ alkyl)-O— or —NR'R".

16. A composition according to claim 15, wherein, in the compound of formula (V), $R^6$ is $C_{1-6}$ alkyl, $C_{1-6}$ alkoxy, $C_{1-6}$ alkylthio, aryl, heteroaryl, carbocyclyl, heterocycly, phenyl-($C_{1-2}$ alkyl)-, phenyl-($C_{1-2}$ alkyl)—O —, heteroaryl-($C_{1-2}$ alkyl)-, phenyl-($C_{1-2}$ hydroxyalkyl)-, heteroaryl-($C_{1-2}$ hydroxyalkyl)- or —NR'R".

17. A composition according to claim 16, wherein, in the compound of formula (V), $R^6$ is $C_{1-4}$ alkyl, $C_{1-4}$ alkoxy, phenyl, naphthyl, dihydrobenzofuranyl, benzodioxinyl, 9H-fluoren-9-onyl, indolyl, thienyl, furanyl, oxazolyl, isoxazolyl, pyrazolyl, pyridyl, benzothienyl, benzofuranyl, cyclopentyl, cyclohexyl, piperazinyl, piperidinyl, morpholinyl, phenyl-($C_{1-2}$ alkyl)-, phenyl-$CH_2$—CH(OH)—, phenyl-CH(OH)—$CH_2$-, phenyl-($C_{1-2}$ alkyl)-O —, 1H-benzo[d]imidazol-2(3H)-onyl or —NR'R".

18. A composition according to claim 1, wherein, in the compound of formula (V), the benzodiazepine derivative of formula (V) is a benzodiazepine derivative of formula (Va):

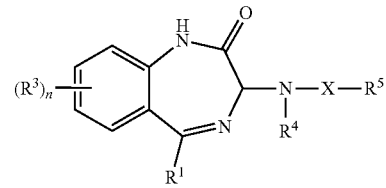

wherein:
$R^1$ is phenyl or methyl;
$R^3$ is methyl or chlorine;
n is 0 or 1;
$R^4$ is hydrogen or methyl;
$R^5$ is phenyl-$CH_2$-, furanyl-$CH_2$-, thienyl-C(O)—C(O)— or —$XR^6$;
X is —CO— or —$S(O)_2$-; and
$R^6$ is $C_{1-4}$ alkyl, $C_{1-4}$ alkoxy, phenyl, naphthyl, dihydrobenzofuranyl, benzodioxinyl, 9H—fluoren-9-onyl, indolyl, thienyl, furanyl, oxazolyl, isoxazolyl, pyrazolyl, pyridyl, benzothienyl, benzofuranyl, cyclopentyl, cyclohexyl, piperazinyl, piperidinyl, morpholinyl, phenyl-($C_{1-2}$ alkyl)-, phenyl-$CH_2$—CH(OH)-phenyl-CH(OH)—$CH_2$-, phenyl-($C_{1-2}$ alkyl)-O—, 1H-benzo[d]imidazol-2(3H)-onyl or —NR'R" wherein each R' and R" is the same or different and represents hydrogen, $C_{1-4}$ alkyl, phenyl, thienyl, cyclohexyl, cyclopentyl or phenyl-($CH_2$)-, the phenyl moiety in the group $R^1$ being unsubstituted or substituted by a single fluorine, chlorine, $C_{1-2}$ alkyl, $C_{1-2}$ alkoxy, $C_{1-2}$ alkylthio, $C_{1-2}$ haloalkyl or $C_{1-2}$ haloalkoxy substituent;
the aryl moieties in the groups $R^5$ and $R^6$ being unsubstituted or substituted by 1, 2 or 3 substituents selected from fluorine, chlorine, bromine, iodine, $C_{1-4}$ alkyl, $C_{2-4}$ acyl, hydroxy, $C_{1-4}$ alkoxy, $C_{1-4}$ alkylthio, $C_{1-4}$ haloalkyl, $C_{1-4}$ haloalkoxy, amino, mono($C_{1-4}$ alkyl) amino, di($C_{1-4}$ alkyl)amino, nitro, —$CO_2$R', —$S(O)_2$R' and —$S(O)_2NH_2$, wherein R' represents $C_{1-2}$ alkyl;
the heteroaryl moieties in the groups $R^5$ and $R^6$ being unsubstituted or substituted by 1 or 2 substituents selected from fluorine, chlorine, bromine, $C_{1-2}$ alkyl, $C_{1-2}$ haloalkyl and di($C_{1-2}$ alkyl)amino; and
the heterocyclyl and carbocyclyl moieties in the $R^6$ group being unsubstituted or substituted by 1 or 2 substituents selected from fluorine, chlorine, bromine, $C_{1-4}$ alkyl, $C_{1-4}$ alkoxy, $C_{1-4}$ haloalkyl and nitro.

19. A composition comprising a pharmaceutically acceptable carrier or diluent and:
(a) an inhibitor of the RSV fusion protein; and
(b) a benzodiazepine derivative capable of inhibiting RSV replication wherein component (a) is a compound of formula (I);

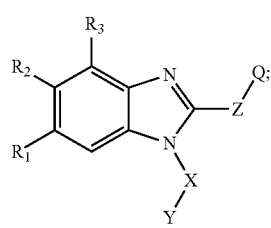

or a pharmaceutically acceptable salt thereof, wherein:

X is a direct link

Y is:

Z is $CR_6R'$, where $R_6$ is H, or straight, branched or cyclic $C_{1-6}$ alkyl and R' is straight, branched or cyclic $C_{1-6}$ alkyl;

$R_1$ is H, $CONR_4R_5$, $CO_2R_4$ or $C_{1-6}$ alkyl, said $C_{1-6}$ alkyl can be optionally substituted with $OR_4$ or $NR_8R_9$;

$R_4$ and $R_5$ are H or $C_{1-6}$ alkyl;

$R_8$ and $R_9$ are each independently H, $C_{1-6}$ alkyl, $SO_2R_5$, $CO_2R_4$ or $COR_4$;

$R_2$ is selected from the group consisting of H, $NH_2$, $CONR_6R'$, heteroaryl, $C_{2-6}$ alkenyl, $CO_2R_4$, $N=CPh_2$, $C(=NH)NH_2$ and $C_{1-6}$ alkyl; said alkyl optionally substituted with a member selected from the group consisting of halogen, CN, $_{NR10}R_{11}$, $OSO_2R_4$ and $OR_4$;

$R_{10}$ and $R_{11}$ are each independently selected from the group consisting of H, $C_{1-6}$ alkyl, $C_{3-6}$ cycloalkyl, $CO_2R_4$, $COR_4$ and $SO_2R_4$;

$R_3$ is selected from the group consisting of (1) $CO_2R_9$; (2) $C_{1-6}$ alkyl optionally substituted with CN, $OR_4$ or $NR_6R'$; (3) H; and (4) $C_{2-6}$ alkenyl substituted with CN;

Q is

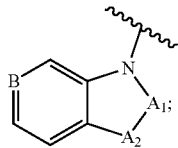

B is —CH— or —N—;

$A_1$ is —C(O)— or —NH—;

$A_2$ is —$CH_2$—, —CHR'— or —NR"—, wherein R' is a halogen atom and R" represents a hydrogen atom or a $C_{1-4}$ alkyl, $C_2$-$C_4$ alkenyl, $C_3$-$C_6$ cycloalkyl, $SO_2$,-($C_1$ -$C_6$ alkyl), —$SO_2$—$N(C_1$-$C_6$ alkyl$)_2$ or -(CONH)a($C_1$-$C_4$ alkyl)-phenyl group, wherein a is 0 or 1, which group is unsubstituted or is substituted with a hydroxyl or cyano substituent; and wherein component (b) is selected from:

Cyclohexanecarboxylic acid 2-oxo-5-phenyl-2,3-dihydro-1H-benzo[e][1,4]diazepin-3-yl)-amide;
3-Methoxy N-(2-oxo-5-phenyl-2,3-dihydro-1H-benzo[e][1,4]diazepin-3-yl)-benzamide;
4-Methoxy N-(2-oxo-5-phenyl-2,3-dihydro-1H-benzo[e][1,4]diazepin-3-yl)-benzamide;
2-Methoxy N-(2-oxo-5-phenyl-2,3-dihydro-1H-benzo[e][1,4]diazepin-3-yl)-benzamide;
N-(2-Oxo-5-phenyl-2,3-dihydro-1H-benzo[e][1,4]diazepin-3-yl)-3-trifluoromethyl-benzamide;
N-(2-Oxo-5-phenyl-2,3-dihydro-1H-benzo[e][1,4]diazepin-3-yl)-benzamide;
Thiophene-2-carboxylic acid (2-oxo-5-phenyl-2,3-dihydro-1H-benzo[e][1,4]diazepin-3-yl )-3-amide;
Furan-2-carboxylic acid (2-oxo-5-phenyl-2,3-dihydro-1H-benzo[e][1,4]diazepin-3-yl)-amide;
Piperidine-1-carboxylic acid (2-oxo-5-phenyl-2,3-dihydro-1H-benzo[e][1,4]diazepin-3yl )-amide;
Morpholine-4-carboxylic acid (2-oxo-5-phenyl-2,3-dihydro-1H-benzo[e][1,4]diazepin-3-yl)-amide;
4-Nitro-N-(2-oxo-5-phenyl-2,3-dihydro-1H-benzo[e][1,4]diazepin-3-yl)-benzamide;
3-Nitro-N-(2-oxo-5-phenyl-2,3-dihydro-1H-benzo[e][1,4]diazepin-3-yl)-benzamide;
4-Methyl-piperazine-l-carboxylic acid-(2-oxo-5-phenyl-2,3-dihydro-1H-benzo[e][1,4]diazepin-3-yl)-amide;
3,4-Dichloro-N-(2-oxo-5-phenyl-2,3-dihydro-1H-benzo[e][1,4]diazepin-3-yl)-benzamide;
N-(2-oxo-5-phenyl-2,3-dihydro-1H-benzo[e][1,4]diazepin-3-yl)-2-trifluoromethyl-benzamide;
4-Bromo-N-(2-oxo-5-phenyl-2,3-dihydro-1H-benzo[e][1,4]diazepin-3-yl)-benzamide;
2-Methyl-N-(2-oxo-5-phenyl-2,3-dihydro-1H-benzo[e][1,4]diazepin-3-yl)-benzamide;
2-Chloro-N-(2-oxo-5-phenyl-2,3-dihydro-1H-benzo[e][1,4]diazepin-3-yl)-benzamide;
2-Nitro-N-(2-oxo-5-phenyl-2,3-dihydro-1H-benzo[e][1,4]diazepin-3-yl)-benzamide;
2-Methoxy-4-nitro-N-(2-oxo-5-phenyl-2,3-dihydro-1H-benzo[e][1,4]diazepin-3-yl)-benzamide;
(S)-2-Methoxy-4-nitro-N-(2-oxo-5-phenyl-2,3-dihydro-1H-benzo[e][1,4]diazepin-3-yl)-benzamide;
Benzo[b]thiophene-3-carboxylic acid (2-oxo-5-phenyl-2,3-dihydro-1H-benzo[e] [1,4]diazepin-3-yl)-amide;
2,3-Dihydro-benzofuran-5-carboxylic acid (2-oxo-5-phenyl-2,3-dihydro-1H-benzo[e][1,4]diazepin-3-yl)-amide;
Isoxazole-5-carboxylic acid (2-oxo-5-phenyl-2,3-dihydro-1H-benzo[e][1,4]diazepin-3-yl )-amide;
Benzo[b]thiophene-2-carboxylic acid (2-oxo-5-phenyl-2,3-dihydro-1H-benzo[e][1,4]diazepin-3-yl)-amide;
Thiophen-3-carboxylic acid (2-oxo-5-phenyl-2,3-dihydro-1H-benzo[e][1,4]diazepin-3-yl )-amide;
N-(2-Oxo-5-phenyl-2,3-dihydro-1H-benzo[e][1,4]diazepin-3-yl)-isonicotinamide;
N-(2-Oxo-5-phenyl-2,3-dihydro-1H-benzo [e][1,4]diazepin-3-yl)-nicotinamide;
N-(2-Oxo-5-phenyl-2,3-dihydro-1H-benzo[e][1,4]diazepin-3-yl)-methanesulfonamide;
Propane-l-sulfonic acid-(2-oxo-5-phenyl-2,3-dihydro-1H-benzo[e][1,4]diazepin-3-yl)-amide;
Butane-l-sulfonic acid-(2-oxo-5-phenyl-2,3-dihydro-1H-benzo[e][1,4]diazepin-3-yl)-amide;
2-Bromo-N-(2-oxo-5-phenyl-2,3-dihydro-1H-benzo[e][1,4]diazepin-3-yl)-benzenesulfonamide;
3-Bromo-N-(2-oxo-5-phenyl-2,3-dihydro-1H-benzo[e][1,4]diazepin-3-yl)-benzenesulfonamide;
4-Bromo-N-(2-oxo-5-phenyl-2,3-dihydro-1H-benzo[e][1,4]diazepin-3-yl)-benzenesulfonamide;
2-Fluoro-N-(2-oxo-5-phenyl-2,3-dihydro-1H-benzo[e][1,4]diazepin-3-yl)-benzenesulfonamide;
3-(2-Nitro-benzylamino)-5-phenyl-1,3-dihydro-benzo[e][1,4]diazepin-2-one;
3-(3-Nitro-benzylamino)-5-phenyl-1,3-dihydro-benzo[e][1,4]diazepin-2-one;
3-(4-Nitro-benzylamino)-5-phenyl-1,3-dihydro-benzo[e][1,4]diazepin-2-one;
3-(2-Methoxy-benzylamino)-5-phenyl-1,3-dihydro-benzo[e][1,4]diazepin-2-one;
3-(3-Methoxy-benzylamino)-5-phenyl-1,3-dihydro-benzo[e][1,4]diazepin-2-one;
5-Phenyl-3-(2-trifluoromethyl-benzylamino)-1,3-dihydro-benzo[e][1,4]diazepin-2-one;
5-Phenyl-3-(3-trifluoromethyl-benzylamino)-1,3-dihydro-benzo[e][1,4]diazepin-2-one;
5-Phenyl-3-(4-trifluoromethyl-benzylamino)-1,3-dihydro-benzo[e][1,4]diazepin-2-one;
3-[(Furan-2-ylmethyl)-amino]-5-phenyl-1,3-dihydro-benzo[e][1,4]diazepin-2-one;
N-(7-Chloro-2-oxo-5-phenyl-2,3-dihydro-1H-benzo[e][1,4]diazepin-3-yl)-acetamide;

N-(7-Chloro-2-oxo-5-phenyl-2,3-dihydro-1H-benzo[e][1,4]diazepin-3-yl)-isobutyramide;
N-(7-Chloro-2-oxo-5-phenyl-2,3-dihydro-1H-benzo[e][1,4]diazepin-3-yl)-methanesulfonamide;
Furan-2-carboxylic acid (7-chloro-2-oxo-5-phenyl-2,3-dihydro-1H-benzo[e][1,4]diazepin-3-yl)-amide;
Thiophene-2-carboxylic acid (7-chloro-2-oxo-5-phenyl-2,3-dihydro-1H-benzo[e][1,4]diazepin-3-yl)-amide;
Cyclohexanecarboxylic acid (7-Chloro-2-oxo-5-phenyl-2,3-dihydro-1H-benzo[e][1,4]diazepin-3-yl)-amide;
N-(7-Chloro-2-oxo-5-phenyl-2,3-dihydro-1H-benzo[e][1,4]diazepin-3-yl)-2-methoxy-benzamide;
N-(7-Chloro-2-oxo-5-phenyl-2,3-dihydro-1H-benzo[e][1,4]diazepin-3-yl)-4-methoxy-benzamide;
N-(7-Chloro-2-oxo-5-phenyl-2,3-dihydro-1H-benzo[e][1,4]diazepin-3-yl)-2-nitro-benzamide;
2-(2-Methoxy-phenyl)N-(2-oxo-5-phenyl-2,3-dihydro-1H-benzo[e][1,4]diazepin-3-yl)-acetamide;
2-(3-Methoxy-phenyl)N-(2-oxo-5-phenyl-2,3-dihydro-1H-benzo[e][1,4]diazepin-3-yl)-acetamide;
2-(4-Methoxy-phenyl)N-(2-oxo-5-phenyl-2,3-dihydro-1H-benzo[e][1,4]diazepin-3-yl)-acetamide;
2-(4-Nitro-phenyl)N-(2-oxo-5-phenyl-2,3-dihydro-1H-benzo[e][1,4]diazepin-3-yl)-acetamide;
2-(3-Nitro-phenyl)N- (2-oxo-5-phenyl-2,3-dihydro-1H-benzo [e][1,4]diazepin-3-yl)-acetamide;
N-(2-Oxo-5-phenyl-2,3-dihydro-1H-benzo[e][1,4]diazepin-3-yl)-2- (2-trifluoromethyl-phenyl)-acetamide;
N-(2-Oxo-5-phenyl-2,3-dihydro-1H-benzo[e][1,4]diazepin-3-yl)-2- (3 -trifluoromethyl-phenyl)-acetamide;
N-(2-Oxo-5-phenyl-2,3-dihydro-1H-benzo[e][1,4]diazepin-3-yl)-2- (4-trifluoromethyl-phenyl)-acetamide;
1- (2-Methoxy-phenyl)-3- (2-oxo-5-phenyl-2,3-dihydro-1H-benzo[e][1,4]diazepin-3-yl)-urea;
1-(2-Nitro-phenyl)-3-(2-oxo-5-phenyl-2,3-dihydro-1H-benzo[e][1,4]diazepin-3-yl)-urea;
1-(2-Chloro-phenyl)-3-(2-oxo-5-phenyl-2,3-dihydro-1H-benzo[e][1,4]diazepin-3-yl)-urea;
1-(4-Chloro-phenyl)-3- (2-oxo-5-phenyl-2,3-dihydro-1H-benzo[e][1,4]diazepin-3-yl-urea;
1-(2-oxo-5-phenyl-2,3-dihydro- 1H-benzo[e][1,4]diazepin-3-yl)-3-p-tolyl-urea;
1-(2-Fluoro-phenyl)-3-(2-oxo-5-phenyl-2,3-dihydro-1H-benzo[e][1,4]diazepin-3-yl)-urea;
1-(4-Fluoro-phenyl)-3-(2-oxo-5-phenyl-2,3-dihydro-1H-benzo[e][1,4]diazepin-3-yl)-urea;
(S)-1-(2-Fluoro-phenyl)-3-(2-oxo-5-phenyl-2,3-dihydro-1H-benzo[e][1,4]diazepin-3-yl)-urea;
4-Methanesulfonyl-2-methoxy-N-(2-oxo-5-phenyl-2,3-dihydro-1H-benzo[e] [1,4]diazepin-3-yl)-benzamide;
(S)-4-Methanesulfonyl-2-methoxy-N-(2-oxo-5-phenyl-2,3-dihydro-1H-benzo[e][1,4]diazepin-3-yl)-benzamide;
5-Acetyl-2-ethoxy-N-(2-oxo-5-phenyl-2,3-dihydro-1H-benzo[e][1,4]diazepin-3-yl)-benzamide;
(S)-5-Acetyl-2-ethoxy-N-(2-oxo-5-phenyl-2,3-dihydro-1H-benzo[e][1,4]diazepin-3-yl)-benzamide;
6-Fluoro-4H-benzo[1,3]dioxine-8-carboxylic acid (2-oxo-5-phenyl-2,3-dihydro-1H-benzo[e][1,4]diazepin-3-yl)-amide;
(S)-6-Fluoro-4H-benzo[1,3]dioxine-8-carboxylic acid (2-oxo-5-phenyl-2,3-dihydro-1H-benzo[e][1,4]diazepin-3-yl)-amide;
(S)-2-Methoxy-N-(2-oxo-5-phenyl-2,3-dihydro-1H-benzo[e][1,4]diazepin-3-yl)-4-trifluoromethyl-benzamide;
2,4,5-Trifluoro-N-(2-oxo-5-phenyl-2,3-dihydro-1H-benzo[e][1,4]diazepin-3-yl)-benzamide;
(S)-2,4,5-Trifluoro-N-(2-oxo-5-phenyl-2,3-dihydro-1H-benzo[e][1,4]diazepin-3-yl)-benzamide;
2-Hydroxy-N-(2-oxo-5-phenyl-2,3-dihydro-1H-benzo[e][1,4]diazepin-3-yl)-benzamide;
(S)-2-Hydroxy-N-(2-oxo-5-phenyl-2,3-dihydro-1H-benzo[e][1,4]diazepin-3-yl)-benzamide;
1H-Indole-7-carboxylic acid (2-oxo-5-phenyl-2,3-dihydro-1H-benzo[e][1,4]diazepin-3-yl )-amide;
(S)-1H-Indole-7-carboxylic acid (2-oxo-5-phenyl-2,3-dihydro-1H-benzo[e][1,4]diazepin-3-yl)-amide;
3-Methoxy-naphthalene-2-carboxylic acid (2-oxo-5-phenyl-2,3-dihydro-1H—benzo[e][1,4]diazepin-3-yl)-amide;
(S)-3-Methoxy-naphthalene-2-carboxylic acid (2-oxo-5-phenyl-2,3-dihydro-1H—benzo[e][1,4]diazepin-3-yl)-amide;
N-[7-Chloro-5-(2-fluoro-phenyl)-2-oxo-2,3-dihydro-1H-benzo[e][1,4]diazepine-3-yl]-4-methoxoy-benzamide;
1-(2-Fluoro-benzyl)-3-(2-oxo-5-phenyl-2,3-dihydro-1H-benzo[e][1,4]diazepin-3-yl)-urea;
1-(4-Methoxy-benzyl)-3-(2-oxo-5-phenyl-2,3-dihydro-1H-benzo[e][1,4]diazepin-3-yl)-urea;
1-(3-Methyl-benzyl)-3-(2-oxo-5-phenyl-2,3-dihydro-1H-benzo[e][1,4]diazepin-3-yl)-urea;
1-(2-Oxo-5-phenyl-2,3-dihydro-1H-benzo[e][1,4]diazepin-3-yl)-3-(4-trifluoromethyl-phenyl)-urea;
4-Chloro-2-methoxy-N-(2-oxo-5-phenyl-2,3-dihydro-1H-benzo[e][1,4]diazepin-3-yl)-benzamide;
4-Methoxy-3-nitro-N-(2-oxo-5-phenyl-2,3-dihydro-1H-benzo[e][1,4]diazepin-3-yl)benzamide;
3-Methoxy-2-nitro-N-(2-oxo-5-phenyl-2,3-dihydro-1H-benzo[e][1,4]diazepin-3-yl)-benzamide;
5-Chloro-2-methoxy-N-(2-oxo-5-phenyl-2,3-dihydro-1H-benzo[e][1,4]diazepin-3-yl)benzamide;
5-Fluoro-2-methoxy-N-(2-oxo-5-phenyl-2,3-dihydro-1H-benzo[e][1,4]diazepin-3-yl)-benzamide;
2-Methoxy-4-nitro-N-(2-oxo-5-phenyl-2,3-dihydro-1H-benzo[e][1,4]diazepin-3-yl)-benzamide;
5-Methoxy-2-nitro-N-(2-oxo-5-phenyl-2,3-dihydro-1H-benzo[e][1,4]diazepin-3-yl)-benzamide;
3-Methoxy-4-nitro-N-(2-oxo-5-phenyl-2,3-dihydro-1H-benzo[e][1,4]diazepin-3-yl)-benzamide;
3-(2-Methoxy-phenyl)-N-(2-oxo-5-phenyl-2,3-dihydro-1H-benzo[e][1,4]diazepin-3-yl)propionamide;
3-(3-Methoxy-phenyl)-N-(2-oxo-5-phenyl-2,3-dihydro-1H-benzo[e][1,4]diazepin-3-yl)-propionamide;
3-(4-Methoxy-phenyl)-N-(2-oxo-5-phenyl-2,3-dihydro-1H-benzo[e][1,4]diazepin-3-yl)-propionamide;
N-[5-(3-Chloro-phenyl)-2-oxo-2,3-dihydro-1H-benzo[e][1,4]diazepin-3-yl]-2-methoxy-benzamide;
N-[5-(3-Chloro-phenyl)-2-oxo-5-phenyl-2,3-dihydro-1H-benzo[e][1,4]diazepin-3-yl]-4-methoxy-benzamide;
N-[5-(3-Chloro-phenyl)-2-oxo-5-phenyl-2,3-dihydro-1H-benzo[e][1,4]diazepin-3-yl]-2-nitro-benzamide;
N-[5-(3-Chloro-phenyl)-2-oxo-5-phenyl-2,3-dihydro-1H-benzo[e][1,4]diazepin-3-yl]-4-nitro-benzamide;
4-Methoxy-N-[2-oxo-5-(4-trifluoromethyl-phenyl)-2,3-dihydro-1H-benzo[e] [1,4]diazepin-3-yl]-benzamide;
2-Methoxy-N-[2-oxo-5-(3-trifluoromethyl-phenyl)-2,3-dihydro-1H-benzo[e] [1,4]diazepin-3-yl]-benzamide;
4-Methoxy-N- [2-oxo-5- (3-trifluoromethyl-phenyl)-2,3-dihydro-1H-benzo [e] [1,4]diazepin-3-yl]-benzamide;
2-Ethoxy-N- (2-oxo-5-phenyl-2,3-dihydro-1H-benzo [e] [1,4]diazepin-3-yl)-benzamide;
2,4-Dimethoxy-N-(2-oxo-5-phenyl-2,3-dihydro-1H-benzo[e][1,4]diazepin-3-yl)-benzamide;

2-Bromo-5-methoxy-N- (2-oxo-5-phenyl-2,3-dihydro-1H-benzo [e][1,4]diazepin-3-yl)-benzamide;
2-Methoxy-N- [5-(3-mehtoxy-phenyl)-2-oxo-2,3-dihydro-1H-benzo [e][1,4]diazepin-3-yl]-benzamide N-[5-(3-Methoxy-phenyl)-2-oxo-5-phenyl-2,3-dihydro-1H-benzo[e][1,4]diazepin-3-yl]4-nitro-benzamide;
2-Methoxy-N- (8-methyl-2-oxo-5-phenyl-2,3-dihydro-1H-benzo [e][1,4]diazepin-3-yl)-benzamide;
2-Chloro-4-methanesulfonyl-N- (2-oxo-5-phenyl-2,3-dihydro-1H-benzo [e][1,4]diazepin-3-yl )-benzamide;
2-Dimethylamino-N-(2-oxo-5-phenyl-2,3-dihydro-1H-benzo [e][1,4]diazepin-3-yl)-benzamide;
(2Oxo-5-phenyl-2,3-dihydro-1H-benzo[e][1,4]diazepin-3-yl)-carbamic acid benzyl ester;
1-(3,5-Dimethyl-phenyl)-3- (2-oxo-5-phenyl-2,3-dihydro-1H-benzo [e][1,4]diazepin-3-yl)-urea;
1-(2Oxo-5-phenyl-2,3-dihydro-1H-benzo[e][1,4]diazepin-3-yl)-3-(4-trifluoromethoxy-phenyl)-urea;
1-(4-Bromo-2-trifluoromethyl-phenyl)-3- (2-oxo-5-phenyl-2,3-dihydro-1H-benzo[e][1,4]diazepin-3-yl)-urea;
1-(4-Bromo-benzyl)-3-(2-oxo-5-phenyl-2,3-dihydro-1H-benzo [e][1,4]diazepin-3-yl)-urea;
1-(2,3-Dichloro-phenyl)-3-(2-oxo-5-phenyl-2,3-dihydro-1H-benzo [e][1,4]diazepin-3-yl)-urea;
1-(2,6-Dimethyl-phenyl)-3-(2-oxo-5-phenyl-2,3-dihydro-1H-benzo [e][1,4]diazepin-3-yl)-urea;
1-(2-Chloro-6-methyl-phenyl)-3-(2-oxo-5-phenyl-2,3-dihydro-1H-benzo[e][1,4]diazepin-3-yl)-urea;
1-(4-Nitro-phenyl)-3-(2-oxo-5-phenyl-2,3-dihydro-1H-benzo[e][1,4]diazepin-3-yl)-urea;
1-(2-Methylsulfanyl-phenyl)-3-(2-oxo-5-phenyl-2,3-dihydro-1H-benzo[e][1,4]diazepin-3-yl )-urea;
1-(2,6-Dichloro-phenyl)-3-(2-oxo-5-phenyl-2,3-dihydro-1H-benzo[e][1,4]diazepin-3-yl)-urea;
5-tert-Butyl-2-methoxy-N-(2-oxo-5-phenyl-2,3-dihydro-1H-benzo[e][1,4]diazepin-3-yl)-benzamide;
2,5-Dimethoxy-N-(2-oxo-5-phenyl-2,3-dihydro-1H-benzo[e][1,4]diazepin-3-yl)-benzamide;
1-(2,6-Difluoro-phenyl)-3-(2-oxo-5-phenyl-2,3-dihydro-1H-benzo[e][1,4]diazepin-3-yl)-urea;
1-(3-Fluoro-phenyl)-3-(2-oxo-5-phenyl-2,3-dihydro-1H-benzo[e][1,4]diazepin-3-yl)-urea;
1-(3-Methoxy-phenyl)-3-(2-oxo-5-phenyl-2,3-dihydro-1H-benzo[e][1,4]diazepin-3-yl)-urea;
1-(2-Oxo-5-phenyl-2,3-dihydro-1H-benzo[e][1,4]diazepin-3-yl)-3-(3-trifluoromethyl-phenyl)-urea;
1-(3-Chloro-phenyl)-3-(2-oxo-5-phenyl-2,3-dihydro-1H-benzo[e]1,4]diazepin-3-yl)-urea;
2-Methoxy-4-methylsulfanyl-N-(2-oxo-5-phenyl-2,3-dihydro-1H-benzo[e][1,4]diazepin-3-yl )-benzamide;
4-Methanesulfonyl-N-(2-oxo-5-phenyl-2,3-dihydro-1H-benzo[e][1,4]diazepin-3-yl)-benzamide;
N-(2Oxo-5-phenyl-2,3-dihydro-1H-benzo[e][1,4]diazepin-3-yl)terephthalamic acidmethyl ester;
2-Fluoro-N-(2-oxo-5-phenyl-2,3-dihydro-1H-benzo[e][1,4]diazepin-3-yl)-benzamide;
2,6-Difluoro-N-(2-oxo-5-phenyl-2,3-dihydro-1H-benzo [e][1,4]diazepin-3-yl)-benzamide;
N-(2-Oxo-5-phenyl-2, 3-dihydro-1H-benzo[e][1,4]diazepin-3-yl)-2-propoxy-benzamide;
2-Iodo-N-(2-oxo-5-phenyl-2,3-dihydro-1H-benzo[e][1,4] diazepin-3-yl)-benzamide;
3-Methoxy-N-(2-oxo-5-phenyl-2,3-dihydro-1H-benzo[e] [1,4]diazepin-3-yl)-terephthalamic acid methyl ester;
4-Amino-5-chloro-2-methoxy-N-(2-oxo-5-phenyl-2,3-dihydro-1H-benzo[e][1,4]diazepin-3-yl)-benzamide;

1-(2-Oxo-5-phenyl-2,3-dihydro-1H-benzo[e][1,4]diazepin-3-yl)-3-m-tolyl-urea;
2-Methylsulfanyl-N-(2-oxo-5-phenyl-2,3-dihydro-1H-benzo[e][1,4]diazepin-3-yl)-benzamide;
2-Methoxy-N-(2-oxo-5-phenyl-2,3-dihydro-1H-benzo[e][1,4]diazepin-3-yl)-5-sulfamoyl-benzamide;
2-Hydroxy-N-(2-oxo-5-phenyl-2,3-dihydro-1H-benzo[e][1,4]diazepin-3-yl)-3-phenyl-propionamide 3-Hydroxy-N-(2-oxo-5-phenyl-2,3-dihydro-1H-benzo[e][1,4]diazepin-3-yl)-3-phenyl-propionamide;
3-(2-Fluoro-phenyl)-1-methyl-1-(2-oxo-5-phenyl-2,3-dihydro-1H-benzo[e][1,4]diazepin3-yl)-urea;
2-Methoxy-N-methyl-4-nitro-N-(2-oxo-5-phenyl-2,3-dihydro-1H-benzo[e][1,4]diazepin3-yl)-benzamide;
1-tert-Butyl-3-(2-oxo-5-phenyl-2,3-dihydro-1H-benzo[e][1,4]diazepin-3-yl)-urea;
-1-Cyclohexyl-3-(2-oxo-5-phenyl-2,3-dihydro-1H-benzo [e][1,4]diazepin-3-yl)-urea;
1-Ethyl-3-(2-oxo-5-phenyl-2,3-dihydro-1H-benzo[e][1,4]diazepin-3-yl)-urea;
1-Butyl-3-(2-oxo-5-phenyl-2,3-dihydro-1H-benzo[e][1,4]diazepin-3-yl)-urea;
4,5-Dimethyl-furan-2-carboxylic acid (2-oxo-5-phenyl-2,3-dihydro-1H-benzo[e] [1,4]diazepin-3-yl)amide;
Piperidine-l-carboxylic acid (7-chloro-2-oxo-5-phenyl-2,3-dihydro-1H-benzo[e] [1,4]diazepin-3-yl)-amide;
N-[5-(3-Chloro-phenyl)-2-oxo-5-phenyl-2,3-dihydro-1H-benzo[e][1,4]diazepin-3-yl)acetamide;
N-[5-(3-Chloro-phenyl)-2-oxo-5-phenyl-2,3-dihydro-1H-benzo[e][1,4]diazepin-3-yl]-isobutyramide;
Furan-2-carboxylic acid [5-(3-chloro-phenyl)-2-oxo-5-phenyl-2,3-dihydro-1H-benzo[e][1,4]diazepin-3-yl]-amide;
Thiophene-2-carboxylic acid [5-(3-chloro-phenyl)-2-oxo-5-phenyl-2,3-dihydro-1H-benzo[e][1,4]diazepin-3-yl]-amide;
Cyclohexanecarboxylic acid [5-(3chloro-phenyl)-2-oxo-5-phenyl-2,3-dihydro-1Hbenzo[e][1,4]diazepin-3-yl]-amide;
Piperidine-l-carboxylic acid [5-(3-chloro-phenyl)-2-oxo-5-phenyl-2,3-dihydro-1H-benzo[e][1,4]diazepin-3-yl]-amide;
N-[5-(3-Chloro-phenyl)-2-oxo-5-phenyl-2,3-dihydro-1H-benzo [e][1,4]diazepin-3-yl]isonicotinamide;
5-Methyl-furan-2-carboxylic acid (2-oxo-5-phenyl-2,3-dihydro-1H-benzo[e][1,4]diazepin-3-yl)-amide;
Pyrazine-2-carboxylic acid (2-oxo-5-phenyl-2,3-dihydro-1H-benzo[e][1,4]diazepin-3-yl)-amide;
N-[5- (3-Methoxy-phenyl)-2-oxo-5-phenyl2,3-dihydro-1H-benzo[e][1,4]diazepin-3-yl]-is obutyramide;
Thiophene-2-carboxylic acid [5-(3-methoxy-phenyl)-2-oxo-5-phenyl-2,3-dihydro-1H-benzo[e][1,4]diazepin-3-yl]-amide;
Cyclohexanecarboxylic acid [5-(3-methoxy-phenyl)-2-oxo-5-phenyl-2,3-dihydro-1H-benzo[e][1,4]diazepin-3-yl]-amide;
Piperidine- 1 -carboxylic acid [5-(3-methoxy-phenyl)-2-oxo-5-phenyl-2,3-dihydro-1H-benzo[e][1,4]diazepin-3-yl]-amide;
Piperidine-4-carboxylic acid [5-(3-methoxy-phenyl)-2-oxo-5-phenyl-2,3-dihydro-1 H-benzo[e][1,4]diazepin-3-yl]-amide;
Cyclohexanecarboxylic acid (8-chloro-2-oxo-5-phenyl-2,3-dihydro-1H-benzo[e] [1,4]diazepin-3-yl)-amide;
Thiophene-2-carboxylic acid (8-methyl-2-oxo-5-phenyl-2,3-dihydro-1H-benzo[e][1,4]diazepin-3-yl)-amide;

1-(2-Oxo-5-phenyl-2,3-dihydro-1H-benzo[e][1,4]diazepin-3-yl)-3-thiophene-2-yl-urea;
1-(2-Oxo-5-phenyl-2,3-dihydro-1H-benzo[e][1,4]diazepin-3-yl)-3-thiophene-3-yl-urea;
Pyridine-2-carboxylic acid (2-oxo-5-phenyl-2,3-dihydro-1H-benzo[e][1,4]diazepin-3-yl)-amide;
1H-Pyrazole-4-carboxylic acid (2-oxo-5-phenyl-2,3-dihydro-1H-benzo[e][1,4]diazepin-3-yl)-amide;
6-Dimethylamino-N-(2-oxo-5-phenyl-2,3-dihydro-1H-benzo[e][1,4]diazepin-3-yl)-nicotinamide;
2-Ethoxy-naphthalene-1-carboxylic acid (2-oxo-5-phenyl-2,3-dihydro-1H-benzo[e][1,4]diazepin-3-yl)-amide;
9-Oxo-9H-fluorene-1-carboxylic acid (2-oxo-5-phenyl-2,3-dihydro-1H-benzo[e][1,4]diazepin-3-yl)-amide;
2-Oxo-2,3-dihydro-benzoimidazole-1-carboxylic acid (2-oxo-5-phenyl-2,3-dihydro-1H-benzo[e][1,4]diazepin-3-yl)-amide;
(2-Oxo-5-phenyl-2,3-dihydro-1H-benzo[e][1,4]diazepin-3-yl)carbamic acid tert-butyl ester;
(S)-4,5-Dibromo-furan-2-carboxylic acid (2-oxo-5-phenyl-2,3-dihydro-1H-benzo[e][1,4]diazepin-3-yl)-amide;
(S)-Benzofuran-2-carboxylic acid (2-oxo-5-phenyl-2,3-dihydro-1H-benzo[e][1,4]diazepin-3-yl)-amide;
(2-Oxo-5-phenyl-2,3-dihydro-1H-benzo[e][1,4]diazepin-3-yl)-carbamic acid methyl ester;
(2-Oxo-5-phenyl-2,3-dihydro-1H-benzo[e][1,4]diazepin-3-yl)-carbamic acid ethyl ester;
(2-Oxo-5-phenyl-2,3-dihydro-1H-benzo[e][1,4]diazepin-3-yl)-carbamic acid isobutyl ester; or 2-Oxo-N-(2-oxo-5-phenyl-2,3-dihydro-1H-benzo[e][1,4]diazepin-3-yl)-2-thiophene-2-yl-acetamide; or a pharmaceutically acceptable salt thereof.

20. A composition according to claim 19, wherein the benzodiazepine derivative of formula (V) is 1-(2-fluoro-phenyl)-3-(2-oxo-5-phenyl-2,3-dihydro-1H-benzo[e][1,4]diazepin-3-yl)-urea, 2-methoxy-4-nitro-N-(2-oxo-5-phenyl-2,3-dihydro-1H-benzo[e][1,4]diazepin-3-yl)-benzamide or 4-methanesulfonyl-2-methoxy-N-(2-oxo-5-phenyl-2,3-dihydro-1H-benzo[e][1,4]diazepin-3-yl)-benzamide.

21. A composition according to claim 19, wherein the benzodiazepine derivative of formula (V) is 1-(2-fluoro-phenyl)-3-(2-oxo-5-phenyl-2,3-dihydro-1H-benzo[e][1,4]diazepin-3-yl)-urea.

22. A composition comprising a pharmaceutically acceptable carrier or diluent and:
(a) an inhibitor of the RSV fusion protein; and
(b) a benzodiazepine derivative capable of inhibiting RSV replication, wherein component (a) is selected from:
1-Cyclopropyl-3-[1-(4-hydroxy-butyl)-1H-benzoimidazol-2-ylmethyl]-1,3-dihydro-imidazo[4,5-c]pyridin-2-one;
1-Isopropenyl-3-[1-(3-methyl-butyl)-1H-benzoimidazol-2-ylmethyl]-1,3-dihydro-benzoimidazol-2-one;
1-(4-Hydroxy-benzyl)-3-[1-(3-methyl-butyl)-1H-benzoimidazol-2-ylmethyl]-1,3-dihydro-benzoimidazol-2-one;
1-Isopropenyl-3-[1-(3-oxo-butyl)-1H-benzoimidazol-2-ylmethyl]-1,3-dihydro-benzoimidazol-2-one;
1-Ethyl-3-[1-(2-hydroxy-2-phenyl-ethyl)-1H-benzoimidazol-2-ylmethyl]-1,3-dihydro-benzoimidazol-2-one;
1-Ethyl-3-[1-(4-hydroxy-butyl)-1H-benzoimidazol-2-ylmethyl]-1,3-dihydro-benzoimidazol-2-one;
5-{3-[1-(3-Methanesulfonyl-propyl)-1H-benzoimidazol-2-ylmethyl]-2-oxo-2,3-dihydro-benzoimidazol-1-yl}-pentanenitrile;
3-[1-(3-Methyl-butyl)-1H-benzoimidazol-2-ylmethyl]-2-oxo-2,3-dihydro-benzoimidazol-1-carboxylic acid benzylamide;
1-Methanesulfonyl-3-[1-(3-methyl-butyl)-1H-benzoimidazol-2-ylmethyl]-1,3-dihydro-benzoimidazol-2-one;
3-[1-(3-Methyl-butyl)-1H-benzoimidazol-2-ylmethyl]-2-oxo-2,3-dihydro-benzoimidazol-1-sulfonic acid dimethylamide; or
1-Isopropenyl-3-(1-propyl-1H-benzoimidazol-2-ylmethyl)-1,3-dihydro-imidazo[4,5-c]pyridine-2-one;
or a pharmaceutically acceptable salt thereof; and
wherein component (b) is a compound of formula (V), or a pharmaceutically acceptable salt thereof,

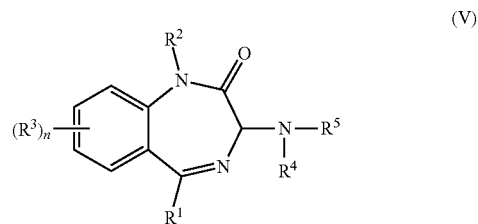

wherein:
$R^1$ represents $C_{1-6}$ alkyl, aryl or heteroaryl;
$R^2$ represents hydrogen or $C_{1-6}$ alkyl;
each $R^3$ is the same or different and represents halogen, hydroxy, $C_{1-6}$ alkyl, $C_{1-6}$ alkoxy, $C_{1-6}$ alkylthio, $C_{1-6}$ haloalkyl, $C_{1-6}$ haloalkoxy, amino, mono($C_{1-6}$ alkyl)amino, di($C_{1-6}$ alkyl)amino, nitro, cyano, —$CO_2R'$, —$CONR'R''$, —NH—CO—R', —S(O)R', —S(O)$_2$R', —NH—S(O)$_2$R', —S(O)NR'R'' or —S(O)$_2$NR'R'', wherein each R' and R'' is the same or different and represents hydrogen or $C_{1-6}$ alkyl;
n is from 0 to 3;
$R^4$ represents hydrogen or $C_{1-6}$ alkyl;
$R^5$ represents $C_{1-6}$ alkyl, aryl, heteroaryl, carbocyclyl, heterocyclyl, aryl-($C_{1-6}$ alkyl)-, heteroaryl-($C_{1-6}$ alkyl)-, carbocyclyl-($C_{1-6}$ alkyl)-, heterocyclyl-($C_{1-6}$ alkyl)-, aryl-($C_{1-6}$ hydroxyalkyl)-, heteroaryl-($C_{1-6}$ hydroxyalkyl)-, carbocyclyl-($C_{1-6}$ hydroxyalkyl)-, heterocyclyl-($C_{1-6}$ hydroxyalkyl)-, aryl-C(O)—C(O)-, heteroaryl-C(O)—C(O)-, carbocyclyl-C(O)—C(O)-, heterocyclyl-C(O)—C(O)- or —$XR^6$;
X represents —CO—, —S(O)- or —S(O)$_2$-; and
$R^6$ represents $C_{1-6}$ alkyl, hydroxy, $C_{1-6}$ alkoxy, $C_{1-6}$ alkylthio, aryl, heteroaryl, carbocyclyl, heterocyclyl, aryl-($C_{1-6}$ alkyl)-, heteroaryl-($C_{1-6}$ alkyl)-, carbocyclyl-($C_{1-6}$ alkyl)-, heterocyclyl-($C_{1-6}$ alkyl)-, aryl-($C_{1-6}$ alkyl)-O—, heteroaryl-($C_{1-6}$ alkyl)—O—, carbocyclyl-($C_{1-6}$ alkyl)—O—, heterocyclyl-($C_{1-6}$ alkyl)—O— or —NR'R'' wherein each R' and R'' is the same or different and represents hydrogen, $C_{1-6}$ alkyl, carbocyclyl, heterocyclyl, aryl, heteroaryl, aryl-($C_{1-6}$ alkyl)-, heteroaryl-($C_{1-6}$ alkyl)-, carbocyclyl-($C_{1-6}$ alkyl)- or heterocyclyl-($C_{1-6}$ alkyl)-.

23. A composition according to claim 22, wherein component (a) is 1-cyclopropyl-3-[1-(4-hydroxy-butyl)-1H-benzoimidazol-2-ylmethyl]-1,3-dihydro-imidazo[4,5-c]pyridin-2-one; or a pharmaceutically acceptable salt thereof.

24. A composition according to claim 22, wherein component (a) is 1-cyclopropyl-3-[1-(4-hydroxy-butyl)-1H-benzoimidazol-2-ylmethyl]-1,3-dihydro-imidazo[4,5-c]pyridin-2-one or 1-Isopropenyl-3-(1-propyl-1H-benzoimidazol-2- ylmethyl)-1,3-dihydro-imidazo[4,5-c]pyridine-2-one, or a pharmaceutically acceptable salt thereof.

25. A composition according to claim 1, wherein component (a) is present in an amount of from 0.025 wt % to 10 wt %.

26. A composition according to claim 1, wherein component (b) is present in an amount of 0.025 wt % to 10 wt %.

27. A composition according to claim 1, for use in the treatment of the human or animal body.

28. A method of treating an RSV infection in a patient, which method comprises the administration to said patient of:
(a) an RSV fusion protein inhibitor as defined in claim 1; and
(b) a benzodiazepine derivative as defined in claim 1.

\* \* \* \* \*